(12) United States Patent
Rivera et al.

(10) Patent No.: US 6,566,073 B1
(45) Date of Patent: May 20, 2003

(54) MATERIALS AND METHODS INVOLVING CONDITIONAL RETENTION DOMAINS

(75) Inventors: Victor Rivera, Arlington, MA (US); Timothy Clackson, Cambridge, MA (US); James Rothman, New York, NY (US)

(73) Assignee: Ariad Gene Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/420,819

(22) Filed: Oct. 19, 1999

Related U.S. Application Data

(63) Continuation of application No. 09/174,799, filed on Oct. 19, 1998, now abandoned.
(60) Provisional application No. 60/137,787, filed on Jun. 2, 1999, and provisional application No. 60/104,743, filed on Oct. 19, 1998.

(51) Int. Cl.[7] .................. G01N 33/53; C12P 21/04; C12N 5/02; C07K 17/00
(52) U.S. Cl. .................. 435/7.1; 435/69.7; 435/325; 530/350
(58) Field of Search .................. 435/7.1, 325, 375, 435/69.7, 69.1; 514/31; 536/6.5; 530/350; 424/93.21

(56) References Cited

U.S. PATENT DOCUMENTS

| | | | | |
|---|---|---|---|---|
| 5,830,462 A | * | 11/1998 | Crabtree et al. | 424/93.21 |
| 5,935,822 A | | 8/1999 | Staehelin et al. | 435/69.7 |
| 6,187,757 B1 | * | 2/2001 | Clackson et al. | 514/31 |

FOREIGN PATENT DOCUMENTS

| | | |
|---|---|---|
| WO | WO 96/06097 | 2/1996 |
| WO | WO 97/31898 | 9/1997 |

OTHER PUBLICATIONS

Pfeffer and Rothman, (1987) Ann. Rev. Biochem. 56:829–852.
Clackson, (1998) Current Opinion in Structural Biology 8:451–458.
Clackson et al., (1998) PNAS USA 95:10437–10442.
Rivera (1998) Methods: A companion to Methods in Enzymology 14:421–429.
Brands et al., (1985) J Cell Biol 101:1724–1732.
Melhus et al., (1992) J Biol Chem 267:12036–12041.
Ronne et al., (1983) J Cell Biol 96:907–910.
Hammond and Helenius, (1995) Current Opinion in Cell Biology 7:523–529.
Alberini et al., (1990) Nature 347:485–487.
Lomas et al., (1992) Nature 357:605–607.
Fan et al., (1999) Nature Medicine 5:112–115.
Keenan et al., (1998) Bioorg Med Chem 6(8):1309–1335.
Miesenbock and Rothman (1995) J. Cell Biol. 129:309–319.
Li et al., (1996) J. Cell Biol. 135:1043–1057.
Reddy and Corley (1998) Bioessays 20:546–554.
Von Figura (1991) Current Opinion in Cell Biology 3:642–646.
Nakayama (1997) Biochem J. 327:625–635.
Gong et al., (1996) Proc Natl Acad Sci USA 93:2219–2223.
Alberini et al., "Secretion of immunoglobulin M assemble intermediates in the presence of reducing agents", Nature, vol. 347, pp. 485–487 (1990).*

* cited by examiner

*Primary Examiner*—Kenneth R. Horlick
*Assistant Examiner*—Cynthia Wilder
(74) *Attorney, Agent, or Firm*—David L. Berstein

(57) ABSTRACT

Materials and methods involving conditional retention domains (CRDs) are disclosed. Also disclosed are fusion proteins containing CRDs and cells expressing such fusion proteins. In addition, the invention provides novel methods for producing target proteins in vivo using fusion proteins containing conditional retention domains and methods for identifying novel CRDs.

21 Claims, 12 Drawing Sheets

F(36M)-EGFP fusions

F(36M)-hGH fusions

EGFP-F(36M)-hGH fusion

F(36M)-insulin fusions

LNGFR-F(36M) fusions

MATERIALS AND METHODS INVOLVING CONDITIONAL RETENTION DOMAINS

The present application is related to provisional application 60/104,743 filed Oct. 19, 1998, which is a provisional of application 60/137,787 filed Jun. 2, 1999, which is a continuation of application Ser. No. 09/174,799 filed Oct. 19, 1998, now ABN.

Background of the Invention
Summary of the Invention
Brief Description of the Figures
Detailed Description
  Definitions:
  Capable of selectively hybridizing
  Cells", "host cells" or "recombinant host cells
  Cell line
  Composite", "fusion", and "recombinant
  coding sequence
  construct
  Derived from
  Domain
  Expression control element
  Gene
  Genetically engineered cells
  Heterologous
  Interact
  Nucleic acid
  polylinker
  Protein", "polypeptide" and "peptide
  recombinant virus
  secretory machinery
  Transfection
  Infection
  Transduction
  Transgene
  vector
  Conditional Retention Domains:
  Cleavage Enzymes:
  Secretory Signal Sequences:
  Target proteins:
  Disposal Targeting Sequences:
  Design and assembly of the DNA constructs
  Promoters
  Introduction of Constructs into Cells
  Introduction of Constructs into Animals
  Viral Vectors:
  Adenoviral vectors
  AAV Vectors
  Hybrid Adenovirus-AAV Vectors
  Retroviruses
  Other Viral Systems
  Administration of Viral Vectors
  Uses
  Methods for identifying CRDs
  Pharmaceutical Compositions & Their Administration to Subjects Containing
  Engineered Cells
  Administration
  Compositions
Examples
  Example 1: Generation of domains and vectors used for expression of F(36M) fusion proteins
  Example 2: Identification and synthesis of a ligand for the conditional retention domain F36M FKBP
  Example 3: The conditional retention domain F(36M) FKBP; studies with hGH
  Example 4: Localization/cleavage of fusion protein
  Example 5: Dose response and kinetics of hGH secretion
  Example 6: Regulated insulin secretion
  Example 7: Regulated expression of a membrane tethered protein
  Example 8: Construction and testing of a construct for conditional secretion of hGH using rat retinol binding protein as a CRD
  Example 9: Physiological effects of regulated insulin secretion in vivo
Claims
Abstract

BACKGROUND OF THE INVENTION

A number of important applications, including for example, gene therapy, production of biological materials and materials and methods for biological research, depend on the ability to induce cells to produce proteins of therapeutic, commercial, or experimental value. A variety of regulatable expression systems have been developed, including systems involving allostery-based switches triggered by tetracycline, RU486 or ecdysone, as well as dimerization-based switches triggered by dimerizing agents such as rapamycin, coumermycin, dimers of FK506, synthetic FKBP-binders and/or CsA, or analogs thereof. See e.g. Clackson, "Controlling mammalian gene expression with small molecules" Current Opinion in Chemical Biology, 1:210–218, 1997. In these expression systems, protein production is regulated at the transcriptional level. An inherent limitation of all such systems is the inability to achieve fine temporal control over secretion of the target protein. For example, secretion of maximal, therapeutic levels of the protein is delayed by many hours or even days until the transcribed mRNA accumulates to levels high enough to produce significant amounts of secreted protein. Likewise, secretion cannot return to low baseline levels following removal of the inducing drug until the mRNA is completely degraded, which may also take many hours or days. For many applications this level of control is not sufficient; in these instances, it would be desirable to induce protein production on a much more rapid time scale than that achievable using transcription-based methods.

SUMMARY OF THE INVENTION

This invention takes a unique approach to the regulated production of a target protein, based not on regulated transcription, but on regulated release or secretion of the target protein. Compositions and methods of this invention are useful in biological research and in gene therapy applications.

Key features of the invention include conditional retention domains ("CRDs"), fusion proteins containing them, ligands which bind to the CRDs and permit release or secretion of the fusion proteins, recombinant nucleic acids encoding such fusion proteins, vectors containing such recombinant nucleic acids, cells transduced with these vectors and other materials and important methods involving such. Key fusion proteins of the invention contain at least two mutually heterologous domains, one of which being a CRD.

More specifically, the fusion proteins of this invention are designed to contain at least one conditional retention domain (CRD) and at least one additional domain that is heterologous thereto, usually with a secretory signal sequence. Proteins containing a secretory signal sequence are translated in the endoplasmic reticulum (ER) and then pass through other secretory compartments such as the cis, medial and trans Golgi on their way to being secreted. However, proteins containing one or more CRDs are, as a rule, retained in the secretory machinery except in the presence of a ligand which binds to the protein. Illustrative examples of CRDs include retinol binding proteins and human FKBP 12 mutants such as F36M hFKBP12, as are discussed in detail below. Concatenation of multiple CRDs may allow the user to modulate the degree of aggregation or retention.

Typically the fusion protein also contains a secretory signal sequence to target the fusion protein to a secretory compartment such as the ER or any part of the Golgi apparatus. Many secretory signal sequences are known. Human growth hormone, for example, is the source of a secretory signal sequence suitable for use in this invention.

Additionally, it is preferred in many embodiments that the fusion protein further contain an enzymatic cleavage site such that a portion of the fusion protein containing the CRD can be cleaved from a portion of the fusion protein containing a peptide sequence heterologous to the CRD. Preferably the enzymatic cleavage site comprises a peptide sequence recognized by a trans-Golgi specific endoprotease such as furin. For instance, a cleavage site for furin is provided by the peptide sequence SARNRQKR (SEQ ID NO. 1).

The portion of the fusion protein which is heterologous to the CRD may comprise any protein or protein domain of interest to the practitioner. For instance, the heterologous portion may comprise a target protein such as insulin, parathyroid hormone or beta-endorphin.

To illustrate this further, one typical fusion protein of the invention comprises a signal sequence, a conditional retention domain, a furin cleavage site, and a polypeptide sequence comprising a selected target protein sequence. An example of such a fusion protein comprises, in N-terminal to C-terminal order, a signal sequence from human growth hormone, three F36M hFKBP 12 domains, a human stromelysin-3 furin cleavage site, and a selected target protein sequence. Fusion proteins may also contain several target proteins each separated by an enzymatic cleavage site. For example, such a fusion protein might contain a signal sequence from human growth hormone, one or more copies of a CRD such as F36M hFKBP 12, a furin cleavage site, a target protein, another furin cleavage site and another target protein. This type of construct allows for simultaneous release of more than one target protein.

In addition, the fusion proteins of this invention may optionally comprise a lysosomal targeting signal or other polypeptide sequence targeting it for degradation. By locating such a peptide sequence together with the CRD(s) on one side of the cleavage site and the selected target polypeptide on the other side of the cleavage site, one can help assure cellular removal of the CRD-containing portion of the fusion protein.

One object of the invention is thus the fusion proteins described herein.

Another object of the invention is the recombinant nucleic acids encoding such fusion proteins. Those recombinant nucleic acids may be operably linked to an expression control sequence permitting their expression in host cells into which they have been transduced, or which otherwise contain them. Any promoter may be used to drive expression of these fusion proteins, including strong promoters like the CMV enhancer, other viral promoters such as the RSV promoter or tissue specific promoters like the MCK enhancer.

Another object is a vector containing a recombinant nucleic acid of the invention, generally operably linked to an expression control sequence. Such vectors include "viral" vectors which contain part or all of a viral genome in addition to the recombinant nucleic acid encoding the fusion protein of this invention. Viral vectors can be designed and used for the production of recombinant viruses harboring a recombinant nucleic acid of this invention. A wide variety of such viral systems are known in the art and may be adapted to the practice of this invention, including e.g. adenovirus, AAV, retrovirus, hybrid adeno-AAV, lentivirus and others.

Recombinant nucleic acids of this invention may be transduced into host cells by any available means e.g. in order to render those cells capable of regulated secretion of a target protein. The cells are preferably eukaryotic cells, generally are animal cells, and in many embodiments are mammalian, whether human or non-human. The cells may be transduced in situ within their host organism, or they may be transduced while being maintained in vitro. The cells may be primary cells or may be from a cell line.

The invention thus provides methods for rendering a cell capable of regulated secretion of a target protein which involves introducing into the cell a recombinant nucleic acid of this invention to yield engineered cells which can express the encoded fusion protein. The recombinant nucleic acid may be introduced in viral or other form into cells maintained in vitro or into cells present within an organism. The resultant engineered cells and their progeny containing one or more of these recombinant nucleic acids may be used in a variety of important applications discussed elsewhere, including human gene therapy, analogous veterinary applications, the creation of cellular or animal models (including transgenic applications), assay applications, and the production of a desired protein in vitro, e.g. for recovery and use. Such cells are useful, for example, in methods involving the addition of a ligand, preferably a cell permeant ligand, to the cells (or administration of the ligand to an organism containing the cells) to regulate secretion of a target protein. Particularly important animal models include rodent (especially mouse and rat) and non-human primate models. In human gene therapy applications, the cells will generally be human and the peptide sequence of each of the various domains present in the fusion proteins will preferably be, or be derived from, a peptide sequence of human origin, to the extent possible.

The invention also provides methods for identifying novel CRDs. CRDs may be identified by two hybrid type methods, in which a genetically engineered host cell is provided which comprises (a) a reporter gene linked to a regulatable expression control element, and (b) a recombinant nucleic acid comprising a polylinker linked to two recombinant nucleic acid sequences, the first recombinant nucleic acid sequence encoding a DNA binding domain and the second recombinant nucleic acid sequence encoding a transcription activation domain, wherein association of the DNA binding domain with the transcription activation domain activates expression of the reporter gene. As described herein, the construct contains a single polylinker linked to two independent translational cassettes. This allows for expression of two fusion proteins, one with a DNA binding domain and the other with a transcription activation domain, each linked to an identical CRD candidate. In addition, genetically engineered host cells are provided which comprise (a) a reporter gene linked to a regulatable expression control element, (b) a first recombinant nucleic acid encoding a fusion protein comprising a transcription activation domain linked to a candidate conditional retention domain, (c) a second recombinant nucleic acid encoding a fusion protein containing a DNA binding domain linked to the candidate conditional retention domain wherein association of the fusion proteins activates expression of the reporter gene.

The invention further provides methods for identifying a ligand capable of binding to a conditional retention domain. See, "Methods for identifying CRDs", part 3, page 46 et seq, below. One such method uses cells genetically engineered to express a reporter gene when CRD-containing aggregates are disaggregated by an appropriate ligand. The method involves the following steps: (a) contact the genetically engineered cells with candidate ligands under suitable conditions permitting gene expression, (b) observe the presence and/or amount of expression of the reporter gene, and (c) correlate the presence and/or amount of reporter gene expression with contact of cells with one or more candidate ligands.

The invention also provides methods for screening directly for CRDs which enable ligand-dependent secretion of a target protein or ligand-dependent localization of a membrane protein. For these screening assays, fusion proteins are expressed which encode members of a library of candidate CRDs linked to a signal sequence and an enzymatic cleavage site. These domains are further linked to either a secreted target protein or the extracellular and membrane domain of a membrane protein. The fusion proteins are expressed under conditions permitting secretion of the target protein or localization of the membrane protein. Cells containing the fusion proteins are treated with a ligand that binds the CRD, and then the ligand-dependent presence of the secreted protein or membrane protein is assessed. Secretion of the target protein and/or localization of the membrane protein is then correlated with one or more individual members of the CRD library.

BRIEF DESCRIPTION OF THE FIGURES

FIG. 2: Constructs used to make CRD-containing fusion proteins.

FIG. 6: Kinetics of secretion in response to ligand.

DETAILED DESCRIPTION

Definitions

Figure 1:
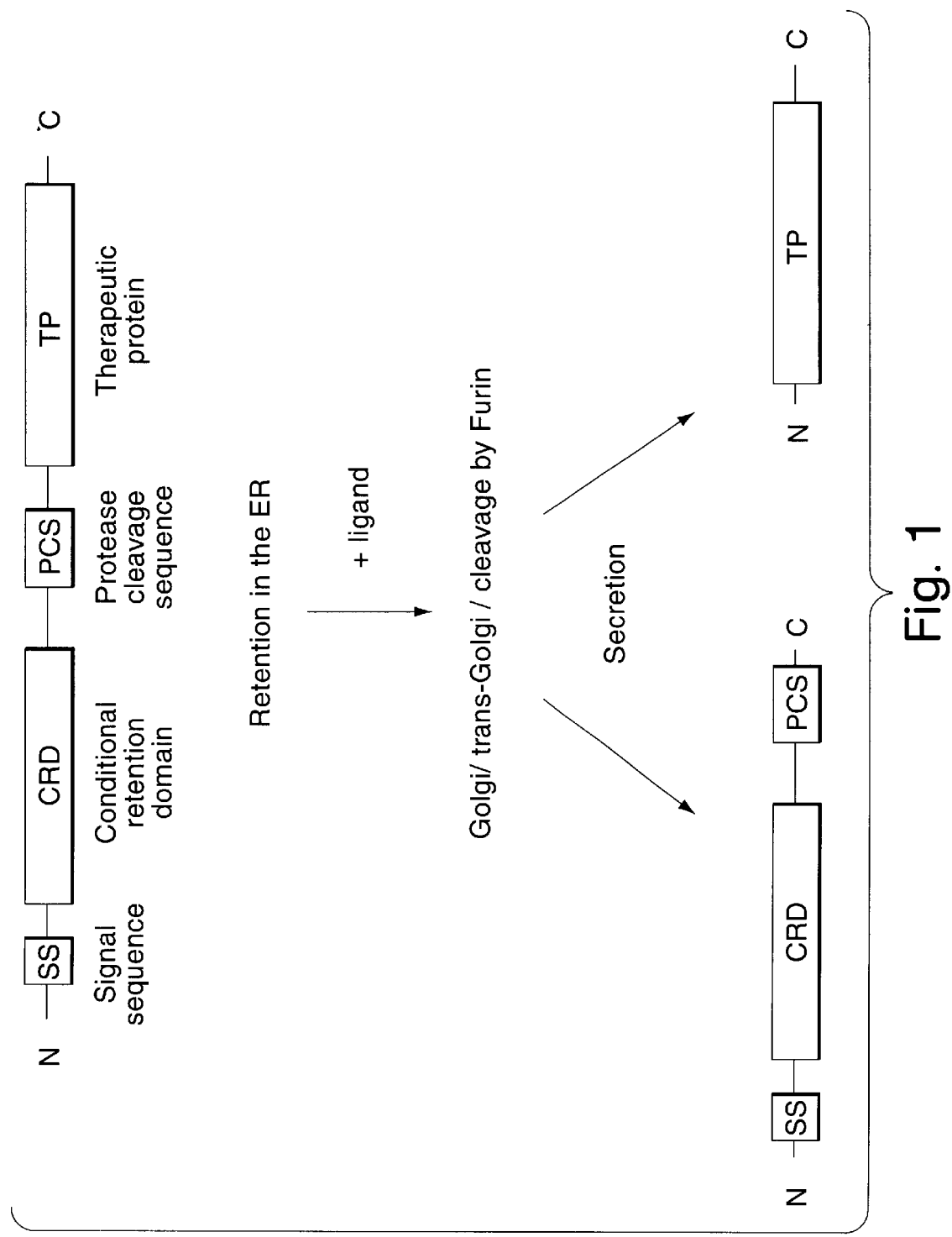
FIG. 1: General design of fusion proteins for use in this invention, containing, from amino- to carboxy-terminus, a secretion signal sequence, a "conditional retention domain", a protease cleavage site, and the secreted target protein of interest.

For convenience, the intended meaning of certain terms and phrases used herein are provided below.

"Capable of selectively hybridizing" means that two DNA molecules are susceptible to detectable hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65–75° C. See for example F. M. Ausubel et al., Eds, Short Protocols in Molecular Biology, Units 6.3 and 6.4 (John Wiley and Sons, New York, 3d Edition, 1995).

"Cells", "host cells" or "recombinant host cells" refer not only to the particular cells under discussion, but also to their progeny. Because certain modifications may occur in succeeding generations due to either mutation or environmental influences, such progeny may not, in fact, be identical to the parent cell, but are still included within the scope of the term as used herein.

"Cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from a given cell line may not be precisely identical to the ancestral cells or cultures, and the cell line referred to includes such variants.

"Composite", "fusion", and "recombinant" denote a material such as a nucleic acid, nucleic acid sequence or polypeptide which contains at least two constituent portions which are mutually heterologous in the sense that they are not otherwise found directly (covalently) linked in nature, i.e., are not found in the same continuous polypeptide or gene in nature, at least not in the same order or orientation or with the same spacing present in the composite, fusion or recombinant product. Typically, such materials contain components derived from at least two different proteins or genes or from at least two non-adjacent portions of the same protein or gene. In general, "composite" refers to portions of different proteins or nucleic acids which are joined together to form a single functional unit, while "fusion" generally refers to two or more functional units which are linked together. "Recombinant" is generally used in the context of nucleic acids or nucleic acid sequences.

A "coding sequence" or a sequence which "encodes" a particular polypeptide or RNA, is a nucleic acid sequence which is transcribed (in the case of DNA) and translated (in the case of mRNA) into a polypeptide in vitro or in vivo when placed under the control of an appropriate expression control sequence. The boundaries of the coding sequence are generally determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and synthetic DNA sequences. A transcription termination sequence will usually be located 3' to the coding sequence.

A "construct", e.g., a "nucleic acid construct" or "DNA construct", refers to a nucleic acid or nucleic acid sequence.

"Derived from" denotes a peptide or nucleotide sequence selected from within a given sequence. A peptide or nucleotide sequence derived from a named sequence may further contain a small number of modifications relative to the parent sequence, in most cases representing deletion, replacement or insertion of less than about 15%, preferably less than about 10%, and in many cases less than about 5%, of amino acid residues or bases present in the parent sequence. In the case of DNAs, one DNA molecule is also considered to be derived from another if the two are capable of selectively hybridizing to one another. Polypeptides or polypeptide sequences are also considered to be derived from a reference polypeptide or polypeptide sequence if any DNAs encoding the two polypeptides or sequences are capable of selectively hybridizing to one another. Typically, a derived peptide sequence will differ from a parent sequence by the replacement of up to 5 amino acids, in many cases up to 3 amino acids, and very often by 0 or 1 amino acids. A derived nucleic acid sequence will differ from a parent sequence by the replacement of up to 15 bases, in many cases up to 9 bases, and very often by 0–3 bases. In some cases the amino acid(s) or base(s) is/are added or deleted rather than replaced.

"Domain" refers to a portion of a protein or polypeptide. In the art, the term "domain" may refer to a portion of a protein having a discrete secondary structure. However, as will be apparent from the context used herein, the term "domain" as used in this document does not necessarily connote a given secondary structure. Rather, a peptide sequence is referred to herein as a "domain" simply to denote a polypeptide sequence from a defined source, or having or conferring an intended or observed activity. Domains can be derived from naturally occurring proteins or may comprise non-naturally-occurring sequence.

"Expression control element", or simply "control element", refers to DNA sequences, such as initiation signals, enhancers, promoters and silencers, which induce or control transcription of DNA sequences with which they are operably linked. Control elements of a gene may be located in introns, exons, coding regions, and 3' flanking sequences. Some control elements are "tissue specific", i.e., affect expression of the selected DNA sequence preferentially in specific cells (e.g., cells of a specific tissue), while others are active in many or most cell types. Gene expression occurs preferentially in a specific cell if expression in this cell type is observably higher than expression in other cell types. Control elements include so-called "leaky" promoters, which regulate expression of a selected DNA primarily in one tissue, but cause expression in other tissues as well. Furthermore, a control element can act constitutively or inducibly. An inducible promoter, for example, is demonstrably more active in response to a stimulus than in the absence of that stimulus. A stimulus can comprise a hormone, cytokine, heavy metal, phorbol ester, cyclic AMP (cAMP), retinoic acid or derivative thereof, etc. A nucleotide sequence containing one or more expression control elements may be referred to as an "expression control sequence".

"Gene" refers to a nucleic acid molecule or sequence comprising an open reading frame and including at least one exon and (optionally) one or more intron sequences.

"Genetically engineered cells" denotes cells which have been modified by the introduction of recombinant or heterologous nucleic acids (e.g. one or more DNA constructs or their RNA counterparts) and further includes the progeny of such cells which retain part or all of such genetic modification.

"Heterologous", as it relates to nucleic acid or peptide sequences, denotes sequences that are not normally joined together, and/or are not normally associated with a particular cell. Thus, a "heterologous" region of a nucleic acid construct is a segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, in the case of a cell transduced with a nucleic acid construct which is not normally present in the cell, the cell and the construct would be considered mutually heterologous for purposes of this invention.

"Interact" refers to directly or indirectly detectable interactions between molecules, such as can be detected using, for example, a yeast two hybrid assay or by immunoprecipitation. The term "interact" encompasses "binding" interactions between molecules. Interactions may be, for example, protein-protein, protein-nucleic acid, protein-small molecule or small molecule-nucleic acid in nature.

"Nucleic acid" refers to polynucleotides such as deoxyribonucleic acid (DNA), and, where appropriate, ribonucleic acid (RNA). The term should also be understood to include derivatives, variants and analogs of either RNA or DNA made from nucleotide analogs, and, as applicable to the embodiment being described, single (sense or antisense) and double-stranded polynucleotides.

A "polylinker", also sometimes referred to as a "multiple cloning site" is a region within a vector which contains multiple sites for restriction enzyme cleavage, thus rendering the vector suitable for cloning of exogenous genes.

"Protein", "polypeptide" and "peptide" are used interchangeably.

A "recombinant virus" is a virus particle in which the packaged nucleic acid contains a heterologous portion.

The "secretory machinery" (also called secretory apparatus) of the cell refers to the cellular compartments to which secreted and membrane proteins are targeted and processed. These compartments include the endoplasmic reticulum (ER) and the cis, medial and trans Golgi. In this document, the term ER is often used generically to mean "secretory compartment."

A "target protein" is a protein of interest, the secretion of which is modulated according to the methods of the invention. The target protein can be, for example, a hormone, an endorphin, etc.

"Transfection" means the introduction of a naked nucleic acid molecule into a recipient cell. "Infection" refers to the process wherein a nucleic acid is introduced into a cell by a virus containing that nucleic acid. A "productive infection" refers to the process wherein a virus enters the cell, is replicated, and is then released from the cell (sometimes referred to as a "lytic" infection). "Transduction" encompasses the introduction of nucleic acid into cells by any means.

"Transgene" refers to a nucleic acid sequence which has been introduced into a cell. Daughter cells deriving from a cell in which a transgene has been introduced are also said to contain the transgene (unless it has been deleted). The polypeptide or RNA encoded by a transgene may be partly or entirely heterologous, i.e., foreign, with respect to the animal or cell into which it is introduced. Alternatively, the transgene can be homologous to an endogenous gene of the transgenic animal or cell into which it is introduced, but is designed to be inserted, or is inserted, into the animal's genome in such a way as to alter the genome of the cell into which it is inserted (e.g., it is inserted at a location which differs from that of the natural gene). A transgene can also be present in an episome. A transgene can include one or more expression control elements and any other nucleic acid, (e.g. intron), that may be necessary or desirable for optimal expression of a selected coding sequence.

The term "vector" refers to a nucleic acid molecule capable of transporting another nucleic acid to which it has been linked. One type of vector is an episome, i.e., a nucleic acid capable of extra-chromosomal replication. Often vectors are used which are capable of autonomous replication and/or expression of nucleic acids to which they are linked. Vectors capable of directing the expression of an included gene operatively linked to an expression control sequence can be referred to as "expression vectors". Expression vectors are typically in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of vectors which serve equivalent functions and which are or become known in the art. Viral vectors are nucleic acid molecules containing viral sequences which can be packaged into viral particles.

Conditional Retention Domains

A conditional retention domain is any domain which is retained in the ER or other secretory compartment in the absence of ligand and is released from the secretory machinery when ligand is bound, i.e. in the presence of ligand. The use of CRDs is considered to take advantage of the phenomenon of ER "quality control", whereby proteins that are incorrectly folded or aggregated are retained in the ER rather than traveling to the Golgi. Eventually, most misfolded proteins are degraded, but others have been observed to accumulate in substantial steady-state amounts (eg. the VSV-G protein: A. M. de Silva et al. (1990) J. Cell Biol. 111, 857–866. See also, Kopito, R. R. (1997) Cell 88, 427–430). Several types of domains can function as conditional retention domains:

1) The CRD can be a natural example of a protein that is retained in the secretory machinery in the absence of a particular small molecule. An example of this type of conditional retention domain is or is derived from retinol binding protein (RBP). Retinol binding protein is a serum protein of approximately 20 kD that is a specific carrier for retinol (Vitamin A) (Melhus, H. et al. (1992) J Biol. Chem. 267, 12036–12041). It is retained in the ER in complex with another protein, transerythrin. Upon binding of retinol to RBP, the complex is released from its molecular chaperone and is free to enter the Golgi apparatus. Thus, the retinol binding protein acts as a CRD which is retained in the ER in the absence of ligand and secreted in its presence. Although retinol binding protein is expressed primarily in hepatocytes, it is generally useful as a CRD, since several groups have shown that retinol-mediated secretion of RBP is cell-type independent and requires no hepatocyte specific cofactors (see, e.g. Melhus et al., J. Biol. Chem. 267:12036–12041, 1992.)

Another example of a protein that is retained in the ER in the absence of a small molecule ligand is IgM. Retention of soluble $\mu$ chains in the ER is dependent on a single unpaired cysteine residue. Although secretion of IgM normally requires binding of light chains to the $\mu$ heavy chain, secretion of IgM intermediates can be induced by addition of 2-mercaptoethanol or other reducing agents (Alberini et al., Nature 347:485–487, 1990). Thus, soluble $\mu$ chains can function as CRDs which are secreted in the presence of a thiol-reactive small molecule.

2) The CRD can be an engineered mutant of a natural protein, chosen because it has the property of being selectively retained in the absence of a given small molecule. It is known that mutations that destabilize proteins can lead to ER retention. Without wishing to be bound to any one theory, including that theory, we have observed that some mutations at human FKBP Phe36 lead to proteins that are poorly expressed (eg. F36A), probably due to instability. Such proteins are thought to be retained to some extent in the secretory apparatus. Using a high affinity ligand that binds to the protein to permit ER exit.

3) The CRD can be a protein that self-aggregates in a small molecule-reversible manner. It is known that large protein aggregates are retained in the ER. In such cases, ER retention occurs because of formation of aggregates rather than due to misfolding of proteins. A naturally occurring example of aggregation-dependent ER retention is found in the Z mutation of $\alpha_1$-antitrypsin. In the secreted M form of this plasma protease, a glutamic acid residue is located at position 342 in the reactive center loop of the molecule. In the mutant Z form, this glutamic acid is substituted by lysine; this substitution allows the reactive loop to insert itself into the A-sheet of an adjacent $\alpha_1$-antitrypsin molecule, forming linear, transport-incompetent aggregates. The aggregates accumulate in the ER, but can be released by addition of a peptide which inserts into the A-sheet and prevents polymerization (Hammond and Helenius, Current Opinion in Cell Biology 7:523–529, 1995; Lomas et al., Nature 357:605–607, Jun. 18, 1992).

The mutant form of $\alpha$-galactosidase A that is found in Fabry lymphoblasts provides an additional example of small-molecule dependent release of aggregates from the ER. Whereas the wild-type form of the enzyme is efficiently routed through the secretory pathway, the mutant protein aggregates in the endoplasmic reticulum, contributing, at least in part, to enzyme deficiency in Fabry patients. Recently, Fan et al reported that addition of 1-deoxy-galactonojirimycin (DGJ), a competitive inhibitor of α-galactosidase A, enhances α-galactosidase A activity in Fabry lymphoblasts by acting as a "chemical chaperone", thus accelerating transport and processing of the mutant enzyme (Fan et al., Nature Medicine 5:112–115, 1999).

In a preferred embodiment, the CRD is derived from human FKBP12. In particular, the FKBP mutant F36M functions as a conditional retention domain when fused to a signal sequence and heterologous target sequence in mammalian cells. In the absence of ligand, fusion proteins containing FKBP F36M and a signal sequence self-aggregate and accumulate in the endoplasmic reticulum. Upon addition of ligand, the fusion protein disaggregates and transits through the ER, resulting in secretion of the fusion protein or cleavage products thereof. Another FKBP mutant which functions as a CRD is FKBP W59V.

Ligands for CRDs

A wide variety of ligands, including both naturally occurring and synthetic substances, can be used in this invention to effect disaggregation and/or secretion of the fusion protein molecules from the secretory machinery. Criteria for selecting a ligand are: (A) physiologic acceptability of the ligand (i.e., the ligand lacks undue toxicity towards the cell or animal for which it is to be used), (B) reasonable therapeutic dosage range, (C) suitability for oral administration (i.e., suitable stability in the gastrointestinal system and absorption into the vascular system), for applications in whole animals, including gene therapy applications, (D) ability to cross cellular and other membranes, as necessary, (E) reasonable binding affinity for the CRD (for the desired application), and (F) efficacy in stimulating transit of the fusion protein. Preferably the compound is relatively physiologically inert, but for its affinity for the CRD. The less the ligand binds to native proteins or other materials within the cells to be targeted, the better the response will normally be. Preferably the ligand will be other than a peptide or nucleic acid, and will preferably have a molecular weight of less than about 5000 Daltons, more preferably less than about 1200 Daltons.

In various embodiments where a ligand binding domain for a candidate ligand is endogenous to the cells to be engineered, it is often desirable to alter the peptide sequence of the ligand binding domain and to use a ligand which discriminates between the endogenous and engineered ligand binding domains. Such a ligand should bind preferentially to the engineered ligand binding domain relative to a naturally occurring peptide sequence, e.g., from which the modified domain was derived. This approach can avoid untoward intrinsic activities of the ligand. Significant guidance and illustrative examples toward that end are provided in the various references cited herein.

Substantial structural modification of a ligand for a ligand binding domain is permitted, so long as the modified compound still functions as a ligand for the ligand binding domain of interest, i.e., so long as the compound possesses sufficient binding affinity and specificity to function as disclosed herein. Some of the compounds will be macrocyclics, e.g. macrolides, although linear and branched compounds may be preferred in specific embodiments. Suitable binding affinities will be reflected in Kd values well below $10^{-4}$, preferably below $10^{-6}$, more preferably below about $10^{-7}$, although binding affinities below $10^{-9}$ or $10^{-10}$ are possible, and in some cases will be most desirable.

Illustrative examples of ligand binding domain/ligand pairs include retinol binding protein or variants thereof and retinol or derivatives thereof; cyclophilin or variants thereof and cyclosporin or analogs thereof; FKBP or variants thereof and FK506, FK520, rapamycin, analogs thereof or synthetic FKBP ligands. In the case of a ligand binding domain comprising or derived from an immunophilin or cyclophilin, the complex of the ligand with the ligand binding domain will desirably not bind specifically to calcineurin or FRAP. A wide variety of FK506 derivatives and synthetic FKBP ligands are known which do not have observable immunosuppressive activity. Likewise, a variety of rapamycin analogs are known which bind to FKBP but are not immunosuppressive. See e.g. WO 98/02441 for non-immunosuppressive rapalogs. Those and other ligands can be used as well, depending on the choice of CRD. Numerous assays are known in the art for identifying ligands which bind to CRDs that are identified through screening, as described below.

Ligand binding domain/ligand pairs are illustrated by FKBP domains, e.g. F36M FKBP, and FKBP ligands. In general, it is preferred that the ligand bind preferentially to a mutated (i.e., having a peptide sequence not naturally occurring in the cells to be engineered) FKBP relative to wild-type FKBP. Ligands for FKBP proteins, including F36M FKBP, can comprise or be derived from a naturally occurring FKBP ligand such as rapamycin, FK506 or FK520, or a synthetic FKBP ligand, e.g. as disclosed in PCT/US95/10559; Holt, et al., *J. Amer. Chem. Soc.*, 1993, 115, 9925–9938; Holt, et al., *Biomed. Chem. Lett.*, 1993, 4, 315–320; Luengo, et al., *Biomed. Chem. Lett.*, 1993, 4, 321–324; Yamashita, et al., *Biomed. Chem. Lett.*, 1993, 4, 325–328; PCT/US94/08008. See also EP 0 455 427 A1; EP 0 465 426 A1; U.S. Pat. No. 5,023,26; WO 92/00278; WO 94/18317; WO 97/31898; WO 96/41865; and Van Duyne et al (1991) *Science* 252, 839.

Illustrative types of ligands for FKBP-derived ligand binding domains include the following Genus I:

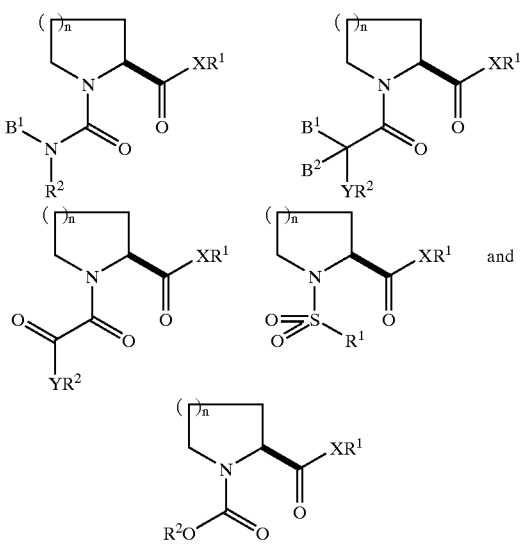

where
n=1 or 2;
X=O,S, NH or CH$_2$;
B$^1$ and B$^2$ are independently H or aliphatic, heteroaliphatic, aryl or heteroaryl as those terms are defined below, usually containing one to about 12 carbon atoms (not counting carbon atoms of optional substituents);

Y=O, S, NH, —NH(C=O)—, —NH(C=O)—O—, —NH(SO₂)— or NR³, or represents a direct, i.e. covalent, bond from R² to carbon 9;

R¹, R², and R³ are aliphatic, heteroaliphatic, aryl or heteroaryl, usually containing one to about 36 carbon atoms (not counting carbon atoms of optional substituents);

two or more of B¹, B² and R² may be covalently linked to form a C3–C7 cyclic or heterocyclic moiety; and, The term "aliphatic" as used herein includes both saturated and unsaturated straight chain, branched, cyclic, or polycyclic aliphatic hydrocarbons, which are optionally substituted with one or more substituents.

The term "substituents" includes aliphatic, aryl, heteroaryl and heterocyclic moieities, which may themselves be substituted, as well as functional groups such as R⁸, —OR⁸, —SR⁸, —CN, —CHO, =O, —COOH, —COR⁸, OS(O)₂R⁸, —SO₂—NHR⁸, —NHSO₂R⁸, sulfate, sulfonate, (or ester, carbamate, urea, oxime or carbonate thereof), —NH₂ (or substituted amine, amide, urea, carbamate or guanidino derivative therof), halo, trihaloalkyl, —SO₂—CF₃, and —OSO₂F, where R⁸ may be H, aliphatic, aryl, heteroaryl or heteroaliphatic. Aliphatic, heteraliphatic, aryl and heterocyclic substituents may themselves be substituted or unsubstituted (e.g. mono-, di- and tri-alkoxyphenyl; methylenedioxyphenyl or ethylenedioxyphenyl; halophenyl; or -phenyl-C(Me)₂—CH₂—O—CO—[C3–C6] alkyl or alkylamino). Additional examples of substituents are illustrated by he specific embodiments shown in the Examples which follow. (Unless otherwise specified, the lkyl, other aliphatic, alkoxy and acyl groups preferably contain 1–8, and in many cases 1–6, contiguous aliphatic carbon atoms).

The term "aliphatic" is thus intended to include alkyl, alkenyl, alkynyl, cycloalkyl, cycloalkenyl, and cycloalkynyl moieties.

As used herein, the term "alkyl" includes both straight and branched alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, butyl, isobutyl, sec-butyl, tert-butyl, pentyl, isopentyl tert-pentyl, hexyl, isohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers to groups having three to seven, preferably three to six carbon atoms. Suitable cycloalkyls include, but are not limited to cyclopropyl, cyclobutyl, cyclopentyl, cyclohexyl, cycloheptyl and the like.

The term "heteroaliphatic" as used herein refers to aliphatic moieties which contain one or more oxygen, sulfur, or nitrogen atoms, e.g., in place of carbon atoms.

The term "heterocycle" as used herein refers to cyclic aliphatic groups having one or more heteroatoms, and preferably three to seven ring atoms total, includes, but is not limited to oxetane, tetrahydrofuranyl, tetrahydropyranyl, aziridine, azetidine, pyrrolidine, piperidine, morpholine, piperazine and the like.

The terms "aryl" and "heteroaryl" as used herein refer to stable mono- or polycyclic, heterocyclic, polycyclic, and polyheterocyclic unsaturated moieties having 3–14 carbon atom which may be substituted or unsubstituted. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like(see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl.

A "halo" substituent according to the present invention may be a fluoro, chloro, bromo or iodo substituent.

As discussed above, R¹ may be aliphatic, heteroaliphatic, aryl or heteroaryl and usually comprises one to about 36 carbon atoms, exclusive of optional substituents.

In certain embodiments, R¹ is optionally be joined, i.e., covalently linked, to R², B¹ or B², forming a macrocyclic structure.

In certain embodiments —XR¹ is a moiety of the formula

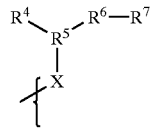

where

R⁴ is a H, aliphatic, heteroaliphatic, aryl or heteroaryl. The aliphatic moieties may be branched, unbranched, cyclic, saturated or unsaturated, substituted or unsubstituted and include, e.g, methyl, ethyl, isopropyl, t-butyl, cyclopentyl, cyclohexyl, etc. Heteroaliphatic moieties may be branched, unbranched or cyclic and include heterocycles such as morpholino, pyrrolidinyl, etc. Illustrative ortho-, meta- or para-, substitutents for a phenyl group at this position include one or more of the following: halo, e.g. chloro or flouro; hydroxyl, amino, —SO₂NH₂, —SO₂NH(aliphatic), —SO₂N(aliphatic)₂, —O—aliphatic-COOH, —O-aliphatic- NH$_2$ (which may contain one or two N-aliphatic or N-acyl substituents), C1–C6 alkyl, acyl, acyloxy, C1–C6 alkoxy, e.g. methoxy, ethoxy, methylenedioxy, ethylenedioxy, etc. Heteroaryl groups are as discussed previously, including indolyl, pyridyl, pyrrolyl, etc. Particular R$^4$ moieties include the following:

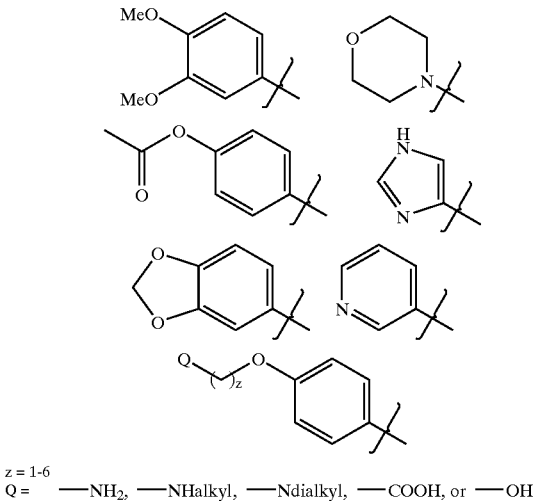

z = 1-6
Q = —NH$_2$, —NHalkyl, —Ndialkyl, —COOH, or —OH

R$^5$ is a branched, unbranched or cyclic aliphatic moiety of 1 to 8 carbon atoms, which may be optionally substituted, including for example, —CH—, —CHCH2—, —CH$_2$CH—, —CHCH$_2$CH$_2$—, —CH$_2$CHCH$_2$—, —CH(CH$_3$)—CH$_2$—CH, —CH(CH$_2$CH$_3$)—CH$_2$—CH, —CH$_2$CH$_2$CH—, —C(CH$_3$)CH$_2$—, and the like;

R$^6$ is an aliphatic, heteroaliphatic, heterocylic, aryl or heteroaryl moiety, which may be substituted or unsubstituted. Typical substituents for R$^6$ include branched, unbranched or to cyclic, C1–C8, aliphatic or heteroaliphatic groups, including unsaturated groups such as substitute or unsubstituted alkenes, heterocycles, phenyl, etc.

R$^7$ is H or a substituent such as, in certain embodiments, —(CH$_2$)$_z$—CH=CH$_2$, —(CH$_2$)$_z$—COOH, —(CH$_2$)$_z$—CHO, —(CH$_2$)$_z$—OH, —(CH$_2$)$_z$—NH$_2$, —(CH$_2$)$_z$—NH-alkyl, —(CH$_2$)$_z$—SH, or an amino group which may be substituted or unsubstituted (preferably a tertiary amine), etc. In embodiments where R$^6$ is aryl, R$^7$ may be present in the o, m, or p position z is an integer from 0 through 4.

As discussed above, B$^1$, B$^2$ and R$^2$ may be aliphatic, heteroaliphatic, aryl or heteroaryl. Typical groups include a branched, unbranched or cyclic, saturated or unsaturated, aliphatic moiety, preferably of 1 to about 12 carbon atoms (including for example methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl and the like), which aliphatic moiety may optionally be substituted with an —OH, —C=O, —COOH, CHO, allyl, NH$_2$ (or substituted amine, amide, urea or carbamate), ether (or thio-ether, in either case, aliphatic or aromatic), aryl, or heteroaryl moiety, and may optionally contain a heteroatom in place of one or more CH$_2$ or CH units; or a substituted or unsubstituted aryl (e.g. mono-, di- and tri-alkoxyphenyl; methylenedioxyphenyl or ethylene- dioxyphenyl; halophenyl; or -phenyl-C(Me)$_2$—CH$_2$—O—CO—[C3–C6] alkyl or alkylamino) or heteroaromatic moiety. In such embodiments, where YR$^2$ is —OPhenyl and B$^1$ is H, B$^2$ is preferably not cyclopentyl. In other embodiments, Y is NH and the moiety —(C=O)—CH(B$^1$)NHR$^2$ comprises among other groups, D- or L-forms of naturally occurring or synthetic alpha amino acids as well as N-alkyl, N-acyl, N-aryl and N-aroyl derivatives thereof. Particular XR$^1$, G, B$^1$, B$^2$ and YR$^2$ groups for the various foregoing structures further include those illustrated in compounds described in the examples, tables of monomers and dimers and other disclosure in WO 96/06097, WO 97/31899 and WO 97/31898.

One preferred class of compounds are those compounds of Genus I in which n is 2.

Another preferred class of compounds are those compounds of Genus I in which B$^1$ is H; B$^2$ is branched, unbranched or cyclic, saturated or unsaturated, aliphatic moiety, preferably of 1 to 8, more preferably 1 to 6, carbon atoms (including for example methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl and the like), which aliphatic moiety may optionally be substituted, e.g. with an —OH, —C=O, —COOH, CHO, allyl, NH$_2$ (or substituted amine, amide, urea or carbamate), or ether (or thio-ether, in either case, aliphatic or aromatic), and may optionally contain a heteroatom in place of one or more CH$_2$ or CH units; and YR$^2$ is aryl, heteroaryl and may be optionally substituted (YR$^2$, for instance, includes moieties such as o-, m-, or p-alkoxyphenyl; 3,5-, 2,3-, 2,4-, 2,5-, 3,4- or 3,5-dialkoxyphenyl, or 3,4,5-trialkoxyphenyl, e.g. where the alkoxy groups are independently selected from methoxy and ethoxy (one or more of which may bear a hydroxy or amino moiety).

Another preferred class of compounds are those compounds of Genus I in which B$^1$, B$^2$ and YR$^2$ are the same or different lower aliphatic moieties.

Another preferred class of compounds are those compounds of Genus I which contain a moiety —NB$^1$R$^2$ in which B$^1$ is H and R$^2$ is lower aliphatic.

Another preferred class of compound are those compounds of Genus I in which G is an alicyclic or heterocyclic group bearing optional substituents.

Another preferred class of compounds are those compounds of Genus I in which X is oxygen and R$^1$ comprises R$^4$R$^5$R$^6$R$^7$ where R$^4$ is aliphatic, alicyclic, aryl, heteroaryl, or heterocyclic, optionally substituted; R$^5$ is a branched or unbranched lower aliphatic group; R$^6$ is aliphatic, alicyclic, heteroaliphatic, heterocyclic, aryl or heteroaryl, optionally substituted.

Another preferred class of compounds are those compounds of Genus I in which R1 comprises R$^4$R$^5$R$^6$R$^7$ as described in the immediately preceding paragraph and YR$^2$ comprises a substituted or unsubstituted aryl or heteroaryl, including phenyl; o-, m- or p- substituted phenyl where the substituent is halo such as chloro, lower alkyl, or alkoxy, such as methoxy or ethoxy; disubstituted phenyl, e.g. dialkoxyphenyl such as 2,4-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4chlorophenyl, etc.).

In addition, such compounds may comprise a substituted proline and pipecolic acid derivative, numerous examples of which have been described in the literature. Using synthetic procedures similar to those described in the patent documents and scientific literature cited herein, substituted prolines and pipecolates can be utilized to prepare ligands with substituents at positions C-2 to C-6 (with reference to the FK506 numbering of most of the references cited below), as exemplified in the patent applications cited herein.

For representative examples of substituted prolines and pipecolic acids see: Chung, et al., *J. Org. Chem.,* 1990, 55, 270; Shuman, et al., *J. Org. Chem.,* 1990, 55, 738; Hanson, et al., *Tetrahedron Lett.,* 1989, 30, 5751; Bailey, et al., *Tetrahedron Lett.,* 1989, 30, 6781.

For a variety of guidance on chemical transformations, synthesis, formulation and delivery of a variety of compounds, including additional information relating to FKBP ligands and/or to ligands for other ligand binding domains, see e.g., WO 94/18317 and Belshaw et al, 1996, PNAS 93:4604–4607) (for methods and materials based on ligands for an immunophilin such as FKBP, a cyclophilin, and/or FRB domain); WO 96/06097 and WO 97/31898 (more ligands for FKBP and variants thereof); WO 93/33052, WO 96/41865 and Rivera et al, "A humanized system for pharmacologic control of gene expression", Nature Medicine 2(9):1028–1032 (1997)) (rapamycin analogs); WO 94/18317 (cyclophilin/cyclosporin); Licitra et al, 1996, Proc. Natl. Acad. Sci. USA 93:12817–12821 (DHFR/methotrexate); and Farrar et al, 1996, Nature 383:178–181 (DNA gyrase/coumermycin). Numerous variations and modifications to ligands and ligand binding domains, as well as methodologies for designing, selecting and/or characterizing them, which may be adapted to the present invention are disclosed in the cited references.

Cleavage Enzymes

It is often preferable in the design of fusion proteins of this invention to have an enzymatic cleavage site located between the CRD and the target protein. When the fusion protein exits the ER following addition of ligand, the enzymatic cleavage site allows the target protein to be released from the CRD and secreted. Ideally, the cleavage site should be specific to an enzyme which resides in a cellular compartment between the ER and the plasma membrane, e.g. the Golgi apparatus. An exemplary cleavage enzyme is furin, also known as PACE. Furin is a member of the KEX2/subtilisin family of pro-protein convertases, which convert pro-proteins and pro-hormones to their active forms (Kazuhisa Nakayama, Biochem J. (1997) 327:625–635). It is a protein which resides in the trans-golgi, although like many golgi proteins such as TGN38, it constitutively cycles between the cell surface and the TGN (trans-golgi network). Furin has a ubiquitous tissue distribution and its substrates are numerous and varied. However, nearly all share the consensus cleavage sequence RX(K/R)R. Proteins which are substrates for furin include: human pro-neurotrophin-3 (MSMRVRR), human pro-insulin like growth factor I (KPAKSAR), human pro-parathyroid hormone (KSVKKR), human stromelysin-3 (ARNRQKR). Furin is also capable of cleaving membrane bound substrates, such as human insulin pro-receptor (RPSRKRR) and human hepatocyte growth factor pro-receptor (TEKRKKR). A cleavage site from any furin substrate can be used in the fusion proteins of the invention. In some cases, the site will be be a non-naturally occurring peptide sequence containing the consensus furin cleavage sequence. One particular advantage of having furin as the cleavage enzyme is that its recognition sequence is located exclusively N-terminal to the cleavage site. This allows the portion of the protein that encodes the target protein to be released from the cell unaltered by the presence of additional amino acids.

The furin family contains other members which may also be useful in the practice of this invention. Many of these proteins have a unique tissue distribution. For example, PC1/PC3 and PC2 are only found in neuroendocrine tissues like pancreatic islets, pituitary and brain and PC4 is expressed primarily within testicular-germ cells. PACE4, as well as PC5/PC6 and LPC/PC7/PC8/SPC7 are expressed ubiquitously (Nakayama, 1997). Cleavage sites for these enzymes may also be used in the practice of this invention, provided the fusion proteins are expressed in the appropriate cell type.

In addition, any mammalian protease with a specific cleavage sequence, such as subtilisin, could be used to cleave the fusion proteins of this invention, if it were targeted to the desired location in the cell. For example, subtilisin could be targeted to the TGN by fusing it to a localization sequence from a resident golgi protein such as TGN38. Alternatively, the motifs which are known to target furin to the TGN, including YKGL and the Ser-containing cluster SDSEEDE, may suffice to target a cytoplasmic protease to the Golgi. Cells may also be engineered to express an enzyme tailored to cut a sequence found only in the CRD containing fusion protein. For example, Ballinger et al. describe mutant forms of subtilisin in which the enzyme has been engineered to acquire the specificity of furin (Ballinger M D, et al. Biochemistry. Oct. 22, 1996;35 (42):13579–85. Ballinger MD, et al. Biochemistry. Oct. 17, 1995;34(41):13312–9.)

Secretory Signal Sequences

When secretory proteins are translated on the ribosome, an amino acid sequence of 16–30 residues, known as the signal sequence, directs the ribosome to the ER membrane, This sequence then initiates a signal which transports the nascent chain into the ER, across the ER membrane. Generally, such sequences are found at the N-terminus of a protein and contain one or more positively charged amino acids followed by a stretch of 6–12 hydrophobic residues. Numerous signal sequences are known, and any signal sequence which normally directs the translocation of a secretory or transmembrane protein to the ER may be used in the fusion proteins of this invention. Exemplary signal sequences are those from preproalbumin, prelysozyme, human growth hormone, proinsulin, acetylcholine receptor or IgG light chain. For use m this invention, a signal sequence is encoded at the N-terminus of the protein to be regulatably secreted. This signal sequence then directs the ribosome to the ER, where the translated protein containing the CRD aggregates until ligand is added to the cell.

Target Proteins

Fusion proteins of this invention may contain any target protein which one may want to secrete or translocate rapidly and efficiently. Preferably, the target protein will be a therapeutic protein. The target protein can provide a desired phenotype. It can be a membrane-bound or membrane-spanning protein, a secreted protein, or a cytoplasmic protein. The proteins which are expressed, singly or in combination, can involve homing, cytotoxicity, proliferation, differentiation, immune response, inflammatory response, clotting, thrombolysis, hormonal regulation, angiogenesis, etc. The polypeptide may be of naturally occurring or non-naturally occurring peptide sequence.

Various secreted products include hormones, such as insulin, human growth hormone, glucagon, pituitary releasing factor, ACTH, melanotropin, relaxin, leptin, etc.; growth factors, such as EGF, IGF-1, TGF-alpha, -beta, PDGF, G-CSF, M-CSF, GM-CSF, members of the FGF family, erythropoietin, thrombopoietin, megakaryocytic growth factors, nerve growth factors, etc.; proteins which stimulate or inhibit angiogenesis such as angiostatin, endostatin and VEGF and variants thereof; interleukins, such as IL-1 to -15; TNF-alpha and -beta; interferons -alpha, -beta and -gamma; and enzymes and other factors, such as tissue plasminogen activator, members of the complement cascade, perforins, superoxide dismutase; coagulation-related factors such as antithrombin-III, Factor V, Factor VII, Factor VIIIc, vWF, Factor IX, alpha-anti-trypsin, protein C, and protein S; endorphins, dynorphin, bone morphogenetic protein, CFTR, etc.

The protein may be a naturally-occurring surface membrane protein or a protein made so by introduction of an appropriate signal peptide and transmembrane sequence. Various such proteins include homing receptors, e.g. L-selectin (Mel-14), hematopoietic cell markers, e.g. CD3, CD4, CD8, B cell receptor, TCR subunits alpha, beta, gamma or delta, CD10, CD19, CD28, CD33, CD38, CD41, etc., receptors, such as the interleukin receptors IL-2R, IL-4R, etc.; receptors for other ligands including the various hormones, growth factors, etc.; receptor antagonists for such receptors and soluble forms of such receptors; channel proteins, for influx or efflux of ions, e.g. $H^+$, $Ca^{+2}$, $K^{+1}$, $Na^+$, $Cl^-$, etc., and the like; CFTR, tyrosine activation motif, zap-70, etc.

The target protein can be an intracellular protein such as a protein involved in a metabolic pathway, or a regulatory protein, steroid receptor, transcription factor, etc., By way of further illustration, in T-cells, one may wish to introduce genes encoding one or both chains of a T-cell receptor. For B-cells, one could provide the heavy and light chains for an immunoglobulin for secretion. For cutaneous cells, e.g. keratinocytes, particularly keratinocyte stem cells, one could provide for protection against infection, by secreting alpha, beta or gamma interferon, antichemotactic factors, proteases specific for bacterial cell wall proteins, various anti-viral proteins,etc.

In various situations, one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. Regulated expression of a membrane protein which recognizes or binds to the particular site of interest, for example, provides a method for directing the engineered cells to that site. Thus one can achieve a localized concentration of a secreted product or effect cell-based healing, scavenging, protection from infection, anti-tumor activity, etc. Proteins of interest include homing receptors, e.g. L-selectin, GMP140, CLAM-1, etc., or addressins, e.g. ELAM-1, PNAd, LNAd, etc., clot binding proteins, or cell surface proteins that respond to localized gradients of chemotactic factors.

In one embodiment of this invention, binding of a ligand to a CRD regulates transcription of a target gene. In this embodiment, the target gene may encode any protein, including those described above.

Disposal Targeting Sequences:

In many embodiments of the invention, it would be desirable to dispose of the CRD following its cleavage from the target protein. Disposal of the CRD would prevent its secretion from the cell and its accumulation in the bloodstream. One way to achieve this goal is to target the CRD to a lysosomal compartment, where it would be degraded. During normal cellular trafficking, lysosomal proteins are sorted from the trans-golgi network, where they are directed to the endosomal pathway, and subsequently, to lysosomes.

Resident soluble lysosomal enzymes such as cathepsin D are marked for targeting to the lysosomal pathway by attachment of a phosphate group on carbon 6 of one or more mannose residues on a particular N-linked oligosaccharide, which are then recognized by the mannose-6-phosphate receptor in the lysozyme. The phosphotransferase recognition sequence of cathepsin D consists of two discontinuous sequences: amino acids 188–230, including a critical lysine residue at position 203, and amino acids 265–292 (Baranski et al., Cell 1990, 63:281–291.) Baranski et al. have demonstrated that splicing of these sequences into the appropriate location on pepsinogen, a secretory protein, resulted in phosphorylation of the sugars on the chimeric molecule (Baranski et al., supra). Other groups have shown that fusion of the entire cathepsin B sequence onto MyoD resulted in targeting of the complex to the lysosome (Li et al., J. Cell Biol., 135:1043–1057, November 1996.) Similarly, chimeric proteins consisting of soluble CD4, procathepsin D and the C-terminal tails of three lysosomal membrane proteins were able to direct the HIV glycoprotein gp160 to the lysosome for degradation (Lin et al., FASEB J., 7:1070–1080, August 1993.) Lysosomal membrane proteins such as lamp-1 and LAP are directed to the lysosome via a tyrosine-based targeting motif in their C-terminal tails (Williams et al., J. Cell Biol., 111:955–966, 1990; Klionsky et al., J. Biol. Chem., 265:5349–5352, 1990.) Fusion of these tails onto the extracellular and transmembrane domains of resident plasma membrane proteins is sufficient to target those proteins to the lysosome.

Either of the aforementioned lysosomal targeting signals may be used to target CRDs of this invention for disposal. For soluble proteins, the preferred method is to fuse a resident lysosomal protein containing a mannose-6-phosphate signal to the CRD. Examples of such proteins are the cysteine proteases of the cathepsin family: cathepsins B, D, H, L, S, C and K. Other lysosomal enzymes which may be used include the carboxypeptidases prolylcarboxypeptidase and deamidase (cathepsin A). For membrane bound CRDs, the preferred targeting sequence would be one found in lysosomal membrane proteins, e.g. a tyrosine-based internalization motif. These motifs are short, linear stretches of amino acids within the cytoplasmic region of the protein to be targeted. Tyrosine-based motifs center on a critical tyrosine residue within the sequence NPXY or YXXØ, where X is any amino acid and Ø is an amino acid with a bulky hydrophobic group. In many proteins, a glycine preceding the tyrosine in a YXXØ-type signal enhances targeting of these proteins to the lysosome. Sequences for use in some applications of this invention may be derived from proteins such as Lamp-1, LAP (lysosomal acid phosphatase), CD63, Lamp-2 or CD3-gamma, all of which are normally targeted to the lysosome. For additional information on tyrosine-based sorting motifs, see, for example the review by Marks et al., Trends in Cell Biology, 7:124–128, 1997.

Design and Assembly of the DNA Constructs

Constructs may be designed in accordance with the principles, illustrative examples and materials and methods disclosed in the patent documents and scientific literature cited herein, with modifications and further exemplification as described. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. In the case of DNA constructs encoding fusion proteins, DNA sequences encoding individual domains and sub-domains are joined such that they constitute a single open reading frame encoding a fusion protein capable of being translated in cells or cell lysates into a single polypeptide harboring all component domains. The DNA construct encoding the fusion protein may then be placed into a vector for transducing host cells and permitting the expression of the protein. For biochemical analysis of the encoded chimera, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

Promoters

The fusion proteins described herein may be used in combination with any promoter that ill direct their expression in mammalian cells. The promoter may be a strong promoter, such as the human CMV promoter, or a weaker promoter, such as a promoter for an endogenous human gene. Other promoters which may be used include, but are not limited to, the Rous Sarcoma Virus (RSV) promoter, the retroviral LTR from Murine Moloney Leukemia Virus (MMLV), the muscle creatine kinase (MCK) enhancer, the SV40 promoter, and the CMV enhancer from the major immediate early gene. Genbank accession numbers for the above promoters are given in the table below.

| Promoter | Genbank Accession Number |
|---|---|
| CMV | AF067197 |
| RSV | M83237 |
| MMLV LTR | M77239 |
| SV40 | U47120 |
| CMV enhancer for MIE gene | K03104 |
| MCK enhancer | X67536 |

In many cases, the selection of promoter will depend upon the configuration of the fusion protein used in a particular application. Thus, if the practitioner desired the CRD-containing fusion protein to be expressed at high levels, a stronger promoter, such as CMV, would be used. Alternatively, for tissue specific expression, a tissue specific promoter like the MCK enhancer (for expression in muscle) would be selected.

Introduction of Constructs into Cells

This invention is particularly useful for the engineering of animal cells and in applications involving the use of such engineered animal cells. The animal cells may be, among others, insect, worm or mammalian cells. While various mammalian cells may be used, including, by way of example, equine, bovine, ovine, canine, feline, murine, and non-human primate cells, human and mouse cells are of particular interest. Across the various species, various types of cells may be used, such as hematopoietic, neural, glial, mesenchymal, cutaneous, mucosal, stromal, muscle (including smooth muscle cells), spleen, reticuloendothelial, epithelial, endothelial, hepatic, kidney, gastrointestinal, pulmonary, fibroblast, and other cell types. Of particular interest are muscle cells (including skeletal, cardiac and other muscle cells), cells of the central and peripheral nervous systems, and hematopoietic cells, which may include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells The cells may be autologous cells, syngeneic cells, allogeneic cells and even in some cases, xenogeneic cells with respect to an intended host organism. The cells may be modified by changing the major histocompatibility complex ("MHC") profile, by inactivating β2-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, and the like.

In some instances specific clones or oligoclonal cells may be of interest, where the cells have a particular specificity, such as T cells and B cells having a specific antigen specificity or homing target site specificity.

Constructs encoding the fusion proteins and comprising target genes of this invention can be introduced into the cells as one or more nucleic acid molecules or constructs, in many cases in association with one or more markers to allow for selection of host cells which contain the construct(s). The constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional domain may be isolated, where one or more mutations may be introduced using "primer repair", ligation, in vitro mutagenesis, etc. as appropriate.

The construct(s) once completed and demonstrated to have the appropriate sequences may then be introduced into a host cell by any convenient means. The constructs may be incorporated into vectors capable of episomal replication (e.g. BPV or EBV vectors) or into vectors designed for integration into the host cells' chromosomes. The constructs may be integrated and packaged into non-replicating, defective viral genomes like Adenovirus, Adeno-associated virus (AAV), or Herpes simplex virus (HSV) or others, including retroviral vectors, for infection or transduction into cells. Alternatively, the construct may be introduced by protoplast fusion, electroporation, biolistics, calcium phosphate transfection, lipofection, microinjection of DNA or the like. The host cells will in some cases be grown and expanded in culture before introduction of the construct(s), followed by the appropriate treatment for introduction of the construct(s) and integration of the construct(s). The cells may then be expanded and/or screened by virtue of a marker present in the constructs. Various markers which may be used successfully include hprt, neomycin resistance, thymidine kinase, hygromycin resistance, etc., and various cell-surface markers such as Tac, CD8, CD3, Thy1 and the NGF receptor.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, *Cell* (1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in prokaryotes or eukaryotes, and mammalian expression control elements, etc. which may be used to prepare stocks of construct DNAs and for carrying out transfections are well known in the art, and many are commercially available.

Introduction of Constructs into Animals

Any means for the introduction of genetically engineered cells or heterologous DNA into animals, preferably mammals, human or non-human, may be adapted to the practice of this invention for the delivery of the various DNA constructs into the intended recipient. For the purpose of this discussion, the various DNA constructs described herein may together be referred to as the transgene.

By ex vivo Genetic Engineering

Cells which have been transduced ex vivo or in vitro with the DNA constructs may be grown in culture under selective conditions and cells which are selected as having the desired construct(s) may then be expanded and further analyzed, using, for example, the polymerase chain reaction for determining the presence of the construct in the host cells and/or assays for the production of the desired gene product(s). After being transduced with the heterologous genetic constructs, the modified host cells may be identified, selected, grown, characterized, etc. as desired, and then may be used as planned, e.g. grown in culture or introduced into a host organism.

Depending upon the nature of the cells, the cells may be introduced into a host organism, e.g. a mammal, in a wide variety of ways, generally by injection or implantation into the desired tissue or compartment, or a tissue or compartment permitting migration of the cells to their intended destination. Illustrative sites for injection or implantation include the vascular system, bone marrow, muscle, liver, cranium or spinal cord, peritoneum, and skin. Hematopoietic cells, for example, may be administered by injection into the vascular system, there being usually at least about $10^4$ cells and generally not more than about $10^{10}$ cells. The number of cells which are employed will depend upon the circumstances, the purpose for the introduction, the lifetime of the cells, the protocol to be used, for example, the number of administrations, the ability of the cells to multiply, the stability of the therapeutic agent, the physiologic need for the therapeutic agent, and the like. Generally, for myoblasts or fibroblasts for example, the number of cells will be at least about $10^4$ and not more than about $10^9$ and may be applied as a dispersion, generally being injected at or near the site of interest. The cells will usually be in a physiologically-acceptable medium.

Cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10):1213–24 (HepG2 cells/hydroxyethyl methacrylate-methyl methacrylate membranes); Chang et al, 1993, Hum Gene Ther 4(4):433–40 (mouse Ltk-cells expressing hGH/immunoprotective perm-selective alginate microcapsules; Reddy et al, 1993, J Infect Dis 168(4):1082–3 (alginate); Tai and Sun, 1993, FASEB J 7(11):1061–9 (mouse fibroblasts expressing hGH/alginate-poly-L-lysine-alginate membrane); Ao et al, 1995, Transplantation Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37–47 (polymer-encapsulated PC12 cells); Sagen et al, 1993, J Neurosci 13(6):2415–23 (bovine chromaffin cells encapsulated in semipermeable polymer membrane and implanted into rat spinal subarachnoid space); Aebischer et al, 1994, Exp Neurol 126(2):151–8 (polymer-encapsulated rat PC12 cells implanted into monkeys; see also Aebischer, WO 92/19595); Savelkoul et al, 1994, J Immunol Methods 170(2):185–96 (encapsulated hybridomas producing antibodies; encapsulated transfected cell lines expressing various cytokines); Winn et al, 1994, PNAS USA 91(6):2324–8 (engineered BHK cells expressing human nerve growth factor encapsulated in an immunoisolation polymeric device and transplanted into rats); Emerich et al, 1994, Prog Neuropsychopharmacol Biol Psychiatry 18(5):935–46 (polymer-encapsulated PC12 cells implanted into rats); Kordower et al, 1994, PNAS USA 91(23):10898–902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more fusion proteins containing component domains derived from proteins of the host species and/or from viral proteins or proteins from species other than the host species. The cells may be derived from one or more individuals other than the recipient and may be derived from a species other than that of the recipient organism or patient.

By in vivo Genetic Engineering

Instead of ex vivo modification of the cells, in many situations one may wish to modify cells in vivo. A variety of techniques have been developed for genetic engineering of target tissue and cells in vivo, including viral and non-viral systems.

In one approach, the DNA constructs are delivered to cells by transfection, i.e., by delivery to cells of "naked DNA", lipid-complexed or liposome-formulated DNA, or otherwise formulated DNA. Prior to formulation of DNA, e.g., with lipid, or as in other approaches, prior to incorporation in a final expression vector, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal. See, e.g., Canonico et al, Am J Respir Cell Mol Biol 10:24–29, 1994 (in vivo transfer of an aerosolized recombinant human alphal-antitrypsin gene complexed to cationic liposomes to the lungs of rabbits); Tsan et al, Am J Physiol 268 (Lung Cell Mol Physiol 12): L1052–L1056, 1995 (transfer of genes to rat lungs via tracheal insufflation of plasmid DNA alone or complexed with cationic liposomes);

Alton et al., Nat Genet. 5:135–142, 1993 (gene transfer to mouse airways by nebulized delivery of cDNA-liposome complexes). In either case, delivery of vectors or naked or formulated DNA can be carried out by instillation via bronchoscopy, after transfer of viral particles to Ringer's, phosphate buffered saline, or other similar vehicle, or by nebulization.

Viral systems include those based on viruses such as adenovirus, adeno-associated virus, hybrid adeno-AAV, lentivirus and retroviruses, which allow for transduction by infection, and in some cases, integration of the virus or transgene into the host genome. See, for example, Dubensky et al. (1984) Proc. Natl. Acad. Sci. USA 81, 7529–7533; Kaneda et al., (1989) Science 243,375–378; Hiebert et al. (1989) Proc. Natl. Acad. Sci. USA 86, 3594–3598; Hatzoglu et al. (1990) J. Biol. Chem. 265, 17285–17293 and Ferry, et al. (1991) Proc. Natl. Acad. Sci. USA 88, 8377–8381. The virus may be administered by injection (e.g. intravascularly or intramuscularly), inhalation, or other parenteral mode. Non-viral delivery methods such as administration of the DNA via complexes with liposomes or by injection, catheter or biolistics may also be used. See e.g. WO 96/41865, PCT/US97/22454 and U.S. Ser. No. 60/084819, for example, for additional guidance on formulation and delivery of recombinant nucleic acids to cells and to organisms.

By employing an attenuated or modified retrovirus carrying a target transcriptional initiation region, if desired, one can activate the virus using one of the subject transcription factor constructs, so that the virus may be produced and transduce adjacent cells.

The use of recombinant viruses to deliver the nucleic acid constructs are of particular interest. The transgene(s) may be incorporated into any of a variety of viruses useful in gene therapy.

In clinical settings, the gene delivery systems (i.e., the recombinant nucleic acids in vectors, virus, lipid formulation or other form) can be introduced into a patient, e.g., by any of a number of known methods. For instance, a pharmaceutical preparation of the gene delivery system can be introduced systemically, e.g. by intravenous injection, inhalation, etc. In some systems, the means of delivery provides for specific or selective transduction of the construct into desired target cells. This can be achieved by regional or local administration (see U.S. Pat. No. 5,328,470) or by stereotactic injection, e.g. Chen et al., (1994) PNAS USA 91: 3054–3057 or by determinants of the delivery means. For instance, some viral systems have a tissue or cell-type specificity for infection. In some systems cell-type or tissue-type expression is achieved by the use of cell-type or tissue-specific expression control elements controlling expression of the gene.

In preferred embodiments of the invention, the subject expression constructs are derived by incorporation of the genetic construct(s) of interest into viral delivery systems including a recombinant retrovirus, adenovirus, adeno-associated virus (AAV), hybrid adenovirus/AAV, herpes virus or lentivirus (although other applications may be carried out using recombinant bacterial or eukaryotic plasmids). While various viral vectors may be used in the practice of this invention, AAV- and adenovirus-based approaches are of particular interest for the transfer of exogenous genes in vivo, particularly into humans and other mammals. The following additional guidance on the choice and use of viral vectors may be helpful to the practitioner, especially with respect to applications involving whole animals (including both human gene therapy and the development and use of animal model systems), whether ex vivo or in vivo.

Viral Vectors
Adenoviral Vectors

A viral gene delivery system useful in the present invention utilizes adenovirus-derived vectors. Knowledge of the genetic organization of adenovirus, a 36 kb, linear and double-stranded DNA virus, allows substitution of a large piece of adenoviral DNA with foreign sequences up to 8 kb. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), which are cis elements necessary for viral DNA replication and packaging. The early (E) and late (L) regions of the genome contain different transcription domains that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan (1990) Radiotherap. Oncol. 19:197). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431–434; and Rosenfeld et al., (1992) Cell 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482–6486), hepatocytes (Herz and Gerard, (1993) PNAS USA 90:2812–2816) and muscle cells (Quantin et al., (1992) PNAS USA 89:2581–2584). Adenovirus vectors have also been used in vaccine development (Grunhaus and Horwitz (1992) Seminar in Virology 3:237; Graham and Prevec (1992) Biotechnology 20:363). Experiments in administering recombinant adenovirus to different tissues include trachea instillation (Rosenfeld et al. (1991); Rosenfeld et al. (1992) Cell 68:143), muscle injection (Ragot et al. (1993) Nature 361:647), peripheral intravenous injection (Herz and Gerard (1993) Proc. Natl. Acad. Sci. U.S.A. 90:2812), and stereotactic inoculation into the brain (Le Gal La Salle et al. (1993) Science 254:988).

Furthermore, the virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109–127). Expression of the inserted gene can be under control of, for example, the E1A promoter, the major late promoter (MLP) and associated leader sequences, the viral E3 promoter, or exogenously added promoter sequences.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector. As stated above, the typical vector according to the present invention is replication defective and will not have an adenovirus E1 region. Thus, it will be most convenient to introduce the nucleic acid of interest at the position from which the E1 coding sequences have been removed. However, the position of insertion of the nucleic acid of interest in a region within the adenovirus sequences is not critical to the present invention. For example, the nucleic acid of interest may also be inserted in lieu of the deleted E3 region in E3 replacement vectors as described previously by Karlsson et. al. (1986) or in the E4 region where a helper cell line or helper virus complements the E4 defect.

A preferred helper cell line is 293 (ATCC Accession No. CRL1573). This helper cell line, also termed a "packaging cell line" was developed by Frank Graham (Graham et al. (1987) J. Gen. Virol. 36:59–72 and Graham (1977) J.General Virology 68:937–940) and provides E1A and E1B in trans. However, helper cell lines may also be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells.

Various adenovirus vectors have been shown to be of use in the transfer of genes to mammals, including humans. Replication-deficient adenovirus vectors have been used to express marker proteins and CFTR in the pulmonary epithelium. Because of their ability to efficiently infect dividing cells, their tropism for the lung, and the relative ease of generation of high titer stocks, adenoviral vectors have been the subject of much research in the last few years, and various vectors have been used to deliver genes to the lungs of human subjects (Zabner et al., Cell 75:207–216, 1993; Crystal, et al., Nat Genet. 8:42–51, 1994; Boucher, et al., Hum Gene Ther 5:615–639, 1994). The first generation E1a deleted adenovirus vectors have been improved upon with a second generation that includes a temperature-sensitive E2a viral protein, designed to express less viral protein and thereby make the virally infected cell less of a target for the immune system (Goldman et al., Human Gene Therapy 6:839–851,1995). More recently, a viral vector deleted of all viral open reading frames has been reported (Fisher et al., Virology 217:11–22, 1996). Moreover, it has been shown that expression of viral IL-10 inhibits the immune response to adenoviral antigen (Qin et al., Human Gene Therapy 8:1365–1374, 1997).

Adenoviruses can also be cell type specific, i.e., infect only restricted types of cells and/or express a transgene only in restricted types of cells. For example, the viruses comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has GenBank Accession No.M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by the same methods (restriction digest, linker ligation or filling in of ends, and ligation) used to insert the CFTR or other genes into the vectors.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/346671) by Kovesdi et al.; PCT/FR94/00624 (WO94/28152) by Imler et al.; PCT/FR94/00851 (WO 95/02697) by Perrocaudet et al., PCT/US95/14793 (WO96/14061) by Wang et al.

AAV Vectors

Another viral vector system useful for delivery of DNA is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97–129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells or muscle cells, and exhibits a high frequency of stable integration (see for example Flotte et al., (1992) Am. J. Respir. Cell. Mol. Biol. 7:349–356; Samulski et al., (1989) J. Virol. 63:3822–3828; and McLaughlin et al., (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251–3260 can be used to introduce DNA into cells. A variety of nucleic acids have been introduced into different cell types using AAV vectors (see for example Hermonat et al., (1984) PNAS USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (Kotin, R. M., Human Gene Therapy 5:793–801, 1994, Table I). A transgene incorporating the various DNA constructs of this invention can similarly be included in an AAV-based vector. As an alternative to inclusion of a constitutive promoter such as CMV to drive expression of the recombinant DNA encoding the fusion protein(s), e.g. fusion proteins comprising an activation domain or DNA-binding domain, an AAV promoter can be used (ITR itself or AAV p5 (Flotte, et al. J. Biol.Chem. 268:3781–3790, 1993)).

Such a vector can be packaged into AAV virions by reported methods. For example, a human cell line such as 293 can be co-transfected with the AAV-based expression vector and another plasmid containing open reading frames encoding AAV rep and cap (which are obligatory for replication and packaging of the recombinant viral construct) under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, B. J., Current Opinion in Biotechnology 3:533–539, 1992; Kotin, R. M, Human Gene Therapy 5:793–801, 1994)). Typically, three days after transfection, recombinant AAV is harvested from the cells along with adenovirus and the contaminating adenovirus is then inactivated by heat treatment.

Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Alternatively, a cell can be transformed with a first AAV vector including a 5' ITR, a 3' ITR flanking a heterologous gene, and a second AAV vector which includes an inducible origin of replication, e.g., SV40 origin of replication, which is capable of being induced by an agent, such as the SV40 T antigen and which includes DNA sequences encoding the AAV rep and cap proteins. Upon induction by an agent, the second AAV vector may replicate to a high copy number, and thereby increased numbers of infectious AAV particles may be generated (see, e.g, U.S. Pat. No. 5,693,531 by Chiorini et al., issued Dec. 2, 1997. In yet another method for producing large amounts of recombinant AAV, a plasmid is used which incorporate the Epstein Barr Nuclear Antigen (EBNA) gene, the latent origin of replication of Epstein Barr virus (oriP) and an AAV genome. These plasmids are maintained as a multicopy extra-chromosomal elements in cells, such as in 293 cells. Upon addition of wild-type helper functions, these cells will produce high amounts of recombinant AAV (U.S. Pat. No. 5,691,176 by Lebkowski et al., issued Nov. 25, 1997). In another system, an AAV packaging plasmid is provided that allows expression of the rep gene, wherein the p5 promoter, which normally controls rep expression, is replaced with a heterologous promoter (U.S. Pat. No. 5,658,776, by Flotte et al., issued Aug. 19, 1997). Additionally, one may increase the efficiency of AAV transduction by treating the cells with an agent that facilitates the conversion of the single stranded form to the double stranded form, as described in Wilson et al., WO96/39530.

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J.Biol. Chem. 268:3781–3790, 1993) or chromatographic purification, as described in O'Riordan et al., WO97/08298.

Methods for in vitro packaging AAV vectors are also available and have the advantage that there is no size limitation of the DNA packaged into the particles (see, U.S. Pat. No. 5,688,676, by Zhou et al., issued Nov. 18, 1997). This procedure involves the preparation of cell free packaging extracts.

For additional detailed guidance on AAV technology which may be useful in the practice of the subject invention, including methods and materials for the incorporation of a transgene, the propagation and purification of the recombinant AAV vector containing the transgene, and its use in transfecting cells and mammals, see e.g. Carter et al, U.S. Pat. No. 4,797,368 (Jan. 10, 1989); Muzyczka et al, U.S. Pat. No. 5,139,941 (Aug. 18, 1992); Lebkowski et al, U.S. Pat. No. 5,173,414 (Dec. 22, 1992); Srivastava, U.S. Pat. No. 5,252,479 (Oct. 12, 1993); Lebkowski et al, U.S. Pat. No. 5,354,678 (Oct. 11, 1994); Shenk et al, U.S. Pat. No. 5,436,146(Jul. 25, 1995); Chatterjee et al, U.S. Pat. No. 5,454,935 (Dec. 12, 1995), Carter et al WO 93/24641 (published Dec. 9, 1993), and Natsoulis, U.S. Pat. No. 5,622,856 (Apr. 22, 1997). Further information regarding AAVs and the adenovirus or herpes helper functions required can be found in the following articles.Berns and Bohensky (1987), "Adeno-Associated Viruses: An Update", Advanced in Virus Research, Academic Press, 33:243–306.

The genome of AAV is described in Laughlin et al. (1983) "Cloning of infectious adeno-associated virus genomes in bacterial plasmids", Gene, 23: 65–73. Expression of AAV is described in Beaton et al. (1989) "Expression from the Adeno-associated virus p5 and p19 promoters is negatively regulated in trans by the rep protein", J. Virol., 63:4450–4454. Construction of rAAV is described in a number of publications: Tratschin et al. (1984) "Adeno-associated virus vector for high frequency integration, expression and rescue of genes in mammalian cells", Mol. Cell. Biol., 4:2072–2081; Hermonat and Muzyczka (1984) "Use of adeno-associated virus as a mammalian DNA cloning vector: Transduction of neomycin resistance into mammalian tissue culture cells", Proc. Natl. Acad. Sci. USA, 81:6466–6470; McLaughlin et al. (1988) "Adeno-associated virus general transduction vectors: Analysis of Proviral Structures", J. Virol., 62:1963–1973; and Samulski et al. (1989) "Helper-free stocks of recombinant adeno-associated viruses: normal integration does require viral gene expression", J. Virol., 63:3822–3828. Cell lines that can be transformed by rAAV are those described in Lebkowski et al. (1988) "Adeno-associated virus: a vector system for efficient introduction and integration of DNA into a variety of mammalian cell types", Mol. Cell. Biol., 8:3988–3996. "Producer" or "packaging" cell lines used in manufacturing recombinant retroviruses are described in Dougherty et al. (1989) J. Virol., 63:3209–3212; and Markowitz et al. (1988) J. Virol., 62:1120–1124.

Hybrid Adenovirus-AAV Vectors

Hybrid Adenovirus-AAV vectors represented by an adenovirus capsid containing a nucleic acid comprising a portion of an adenovirus, and 5' and 3' ITR sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in the this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0–1) and includes the 5' ITR and the packaging/enhancer domain. The 3' adenovirus sequences of the hybrid virus include the right terminal 3' ITR sequence which is about 580 nucinyleotides (about bp 35,353—end of the adenovirus, referred to as about map units 98.4–100.

The AAV sequences useful in the hybrid vector are viral sequences from which the rep and cap polypeptide encoding sequences are deleted and are usually the cis acting 5' and 3' ITR sequences. Thus, the AAV ITR sequences are flanked by the selected adenovirus sequences and the AAV ITR sequences themselves flank a selected transgene. The preparation of the hybrid vector is further described in detail in published PCT application entitled "Hybrid Adenovirus-AAV Virus and Method of Use Thereof", WO 96/13598 by Wilson et al.

For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

Retroviruses

The retroviruses are a group of single-stranded RNA viruses characterized by an ability to convert their RNA to double-stranded DNA in infected cells by a process of reverse-transcription (Coffin (1990) Retroviridae and their Replication" In Fields, Knipe ed. Virology. New York: Raven Press). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsidal proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin (1990), supra).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types. However, integration and stable expression require the division of host cells (Paskind et al. (1975) Virology 67:242).

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(XbaI) (Sawyers et al. (1995) J. Exp. Med. 181:307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395–1398; Danos and Mulligan, (1988) PNAS USA 85:6460–6464; Wilson et al., (1988) PNAS USA 85:3014–3018; Armentano et al., (1990) PNAS USA 87:6141–6145; Huber et al., (1991) PNAS USA 88:8039–8043; Ferry et al., (1991) PNAS USA 88:8377–8381; Chowdhury et al., (1991) Science 254:1802–1805; van Beusechem et al., (1992) PNAS USA 89:7640–7644; Kay et al., (1992) Human Gene Therapy 3:641–647; Dai et al., (1992) PNAS USA 89:10892–10895; Hwu et al., (1993) J. Immunol. 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral env proteins (Neda et al., (1991) J. Biol. Chem. 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Other Viral Systems

Other viral vector systems that may have application in gene therapy have been derived from herpes virus, e.g., Herpes Simplex Virus (U.S. Pat. No. 5,631,236 by Woo et al., issued May 20, 1997), vaccinia virus (Ridgeway (1988) Ridgeway, "Manunalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1–10), and several RNA viruses. Preferred viruses include an alphavirus, a poxvirus, an arena virus, a vaccinia virus, a polio virus, and the like. In particular, herpes virus vectors may provide a unique strategy for persistence of the recombinant gene in cells of the central nervous system and ocular tissue (Pepose et al., (1994) Invest Ophthalmol Vis Sci 35:2662–2666). They offer several attractive features for various mammalian cells (Friedmann (1989) Science, 244:1275–1281; Ridgeway, 1988, supra; Baichwal and Sugden, 1986, supra; Coupar et al., 1988; Horwich et al.(1990) J. Virol., 64:642–650).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990, supra). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al. (1991) Hepatology, 14:124A).

Administration of Viral Vectors

Generally the viral particles are transferred to a biologically compatible solution or pharmaceutically acceptable delivery vehicle, such as sterile saline, or other aqueous or non-aqueous isotonic sterile injection solutions or suspensions, numerous examples of which are well known in the art, including Ringer's, phosphate buffered saline, or other similar vehicles. Delivery of the recombinant viral vector can be carried out via any of several routes of administration, including intramuscular injection, intravenous administration, subcutaneous injection, intrahepatic administration, catheterization (including cardiac catheterization), intracranial injection, nebulization/inhalation or by instillation via bronchoscopy.

Preferably, the DNA or recombinant virus is administered in sufficient amounts to transfect cells within the recipient's target cells, including without limitation, muscle cells, liver cells, various airway epithelial cells and smooth muscle cells, neurons, cardiac muscle cells, etc. and provide sufficient levels of transgene expression to provide for observable ligand-responsive secretion of a target protein, preferably at a level providing therapeutic benefit without undue adverse effects.

Optimal dosages of DNA or virus depends on a variety of factors, as discussed previously, and may thus vary somewhat from patient to patient. Again, therapeutically effective doses of viruses are considered to be in the range of about 20 to about 50 ml of saline solution containing concentrations of from about $1\times10^7$ to about $1\times10^{10}$ pfu of virus/ml, e.g. from $1\times10^8$ to $1\times10^9$ pfu of virus/ml.

Uses

In one application, cells engineered in accordance with the invention are used to produce a target protein in vitro. In such applications, the cells are cultured or otherwise maintained until production of the target protein is desired. At that time, the appropriate ligand is added to the culture medium, in an amount sufficient to cause the desired level of target protein production. The protein so produced may be recovered from the medium or from the cells, and may be purified from other components of the cells or medium as desired.

Proteins for commercial and investigational purposes are often produced using mammalian cell lines engineered to express the protein. The use of mammalian cells, rather than bacteria, insect or yeast cells, is indicated where the proper function of the protein requires post-translational modifications not generally performed by non-mammalian cells. Examples of proteins produced commercially this way include, among others, erythropoietin, BMP-2, tissue plasminogen activator, Factor VIII:c, Factor IX, and antibodies.

In other applications, cells within an animal host or human subject are engineered in accordance with the invention, or cells so engineered are introduced into the animal or human subject, in either case, to prepare the recipient for ligand-mediated regulation of secretion of a therapeutic protein. In the case of non-human animals, this can be done as part of veterinary treatment of the animal or to create an animal model for a variety of research purposes. In the case of human subjects, this can be done as part of a therapeutic or prophylactic treatment program.

This invention is applicable to a variety of treatment approaches. For example, the target protein, e.g. a therapeutic protein, to be regulated can be an endogenous protein or a heterologous protein, and its secretion may be activated by addition of ligand.

In some cases the target protein is a factor necessary for the proliferation and/or differentiation of one or more cell types of interest. For example, it may be desirable to stimulate the secretion of growth factors and lymphokines in a subject in which at least some of the blood cells have been destroyed, e.g., by radiotherapy or chemotherapy. For example, secretion of erythropoietin stimulates the production of red blood cells, secretion of G-CSF stimulates the production of granulocytes, secretion of GM-CSF stimulates the production of various white blood cells, etc. Similarly in diseases or conditions in which one or more specific cell types are destroyed by the disease process, e.g., in autoimmune diseases, the specific cells can be replenished by stimulating secretion of one or more factors stimulating proliferation of these cells. The method of the invention can also be used to increase the number of lymphocytes in a subject having AIDS, such as by stimulating secretion of lymphokines, e.g., IL-4, which stimulates proliferation of certain T helper (Th) cells.

In other cases, the target protein is a hormone or endorphin which must be delivered rapidly and efficiently to its site of action. For example, patients with insulin-dependent diabetes mellitus (IDDM) must artificially maintain physiological levels of insulin in the bloodstream. It would be highly desirable to replace frequent insulin injections with a regulated expression system in which the patient could rapidly produce his/her own insulin when needed. Current regulated expression systems rely on transcriptional mechanisms, in which protein levels increase about 12–16 hours after addition of ligand. In contrast, the present invention would allow delivery of insulin to the appropriate site within 20–30 minutes after ligand binding. As in the case of insulin, the invention described herein could be used to treat any condition which would benefit from rapid delivery of a therapeutic protein. For example, this invention would be useful for delivery of any protein whose biology requires pulsatile or diurnal delivery. Such proteins include, among others, parathyroid hormone or growth hormone. Other uses include delivery of proteins for inflammatory, flaring-type diseases, such as rheumatoid arthritis, inflammatory bowel disease, etc. Examples of such therapeutics would be antibodies to TNF, soluble TNFR, and IL-1RA. More generally, patients would benefit from regulated secretion of any "on-demand" or self-medicating scenario, like insulin (see above) or other agents for managing blood glucose; anti-pain peptides; inflammation (see above); leptin; contraception e.g., antibodies to LHRH.

Methods for Identifying CRDs

Methods are disclosed below for the identification, validation and improvement of CRD candidates of each in each of the three classes described earlier.

1. CRDs Comprising Natural Examples of Proteins Retained in Secretory Compartments in a Small-molecule Reversible Manner Candidate CRDs of this class include any naturally secreted protein or subdomain thereof. Such proteins can typically be identified by the presence of a secretion signal sequence at the start of their coding sequence. The characteristics of such signal sequences are well known and computational algorithms are available to assist in their identification. Using these methods, secreted proteins can be identified from searches of sequence databases. A preferred subset of secreted proteins are those that are known to bind small molecules, or are predicted to do so by their homology to other small molecule-binding proteins. The small molecule may be a ligand or substrate that is transiently bound to the protein during its normal function, or it may be a cofactor that normally remains permanently bound. In either case, these small molecules provides a starting point for identifying ligands for the candidate CRD. In some cases (an example is rat RBP), small molecule-mediated release of the protein from secretory compartments may already be documented in the scientific literature.

Figure 10A:
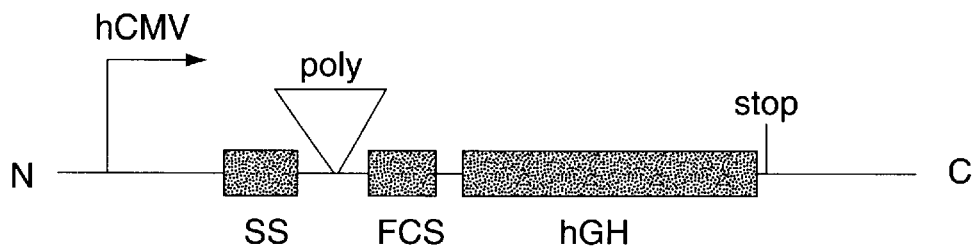
FIG. 10: Constructs useful for screening for novel CRDs. A. Candidate DNA sequences may be cloned into the polylinker for identifying CRDs that induce ligand-dependent secretion of hGH. B. Candidate DNA sequences may be cloned into the polylinker for identifying CRDs that induced ligand-dependent localization of p75. C. Construct used for "two hybrid" style assay, in which fusion proteins containing CRDs cause association of the DNA binding domain and transcription activation domain to induce transcription.

To test whether a candidate protein can function as a CRD, DNA encoding the candidate polypeptide is amplified by PCR or RT-PCR using standard methods from an appropriate source, such as genomic DNA or total or poly A+ RNA isolated from an appropriate cellular source, or a cDNA or genomic DNA library. PCR primers are engineered to include restriction sites allowing insertion into a vector for expression in mammalian cells, or other eukaryotic cells of interest. Alternatively the sequence of interest can be isolated as a restriction fragment. The PCR or restriction fragment is then cloned in frame into the polylinker of an expression vector. A preferred vector is of the form shown in FIG. 10A, where hCMV indicates the human CMV immediate early promoter and enhancer, SS indicates a signal sequence, poly is a polylinker region, FCS is a furin cleavage site, and hGH is a cDNA for human growth hormone. Components of this vector can be substituted as appropriate: for example, FCS can be replaced with alternative TGN protease cleavage sites, and hGH can be replaced with other secreted proteins that can be easily detected and are therefore useful as reporter proteins, such as secreted alkaline phosphatase (SEAP) or erythropoietin (EPO). Optionally, an epitope tag allowing immunochemical detection of the protein (for example the FLAG sequence: IBI/Kodak) can be included in the vector sequence or incorporated via either PCR primer.

To determine whether the candidate polypeptide acts as a CRD, the expression vector is introduced into cells in culture using standard techniques, for example lipofection. After 24 hours, an aliquot of culture medium is removed and assayed for presence of hGH using standard techniques (Rivera et al., 1996). Then, new medium containing various concentrations of candidate CRD ligand are added. After a further period of 2–24 hours, medium is again sampled for presence of hGH. CRD-like activity of the candidate polypeptide is indicated by a low level of hGH in the culture medium in the absence of compound, and increased amounts in the presence of compound. Suitable candidate CRD ligands to investigate include compounds that are known ligands of the protein under study (for example retinol for RBP), and chemically related molecules that may have usefully different properties, such as cell permeability or effects on ER retention of the protein (for example diverse retinoids for RBP). Suitable concentrations of these ligands to investigate are in the range 1 pM to 1 mM.

An important approach for optimizing the effectiveness of CRD candidates is the reiteration of those domains in multiple copies, to attempt to amplify any conditional retention effect. It is anticipated, for example, that some proteins will be 'retarded' in the secretory pathway in the absence of ligand, but not completely retained—that is, retention will be "leaky". In some applications of the invention this will be desirable; in others, tightly repressed protein production in the absence of drug will be needed. In these cases, reiterating the CRD may augment the ability to cause retention of the heterologous protein. Thus, the experiments described above will optionally be repeated on constructs that harbor different numbers of concatenated candidate CRDs: typically between one and eight.

Additional controls that can be performed to verify the activity of a CRD discovered through the above methods include immunochemical detection of the CRD and hGH domains inside cells treated or not treated with the CRD ligand, to confirm that the proteins are retained inside the secretory apparatus. These experiments use standard cell fixing procedures followed by immunofluorescence. Also, the secreted hGH can be checked for correct processing from the fusion protein by size analysis using SDS-PAGE followed by immunoblot with anti-hGH antibodies. For a more exact check, the hGH can be purified (eg. on an hGH binding protein affinity column), and then analyzed for molecular weight by mass spectrometry and for correct processing by immobilization on PVDF followed by N-terminal sequence analysis.

Although the search for CRDs will typically focus on those proteins that are naturally secreted, and further on that subset of secreted proteins with known small molecule-binding activities, any polypeptide can be tested using the methods described above. Thus a protein that is not naturally secreted, but that has a known small molecule binding activity, can be cloned into the FCS-hGH expression vector and tested for CRD behavior that can be reversed by that small molecule (or related molecules). Most generally, any polypeptide—including one that is apparently not normally secreted, and that has no known small molecule binding activity—can be tested. In these cases, the candidate CRD-FCS-hGH expression construct can be first tested for retention of hGH. If retention is observed, cells containing the construct can be challenged in separate experiments with a diverse set of candidate small molecules in order to identify a molecule that can promote secretion of the retained fusion proteins. Suitable sets of molecules include collections of natural products, and the members of synthetic or semi-synthetic combinatorial libraries. Screening may be expedited by arraying cells in 96- or 384-well plates to enable robotic high-throughput set-up and analysis of experiments.

2. CRDs that are Mutants of a Natural Protein, Chosen for the Property of Being Selectively Retained in the Absence of a Given Small Molecule Screening methods for such CRDs follow on naturally from the methods described above. A polypeptide of interest is cloned into the FCS-hGH fusion expression vector described above. Again, preferred polypeptides are those with known small molecule-binding activities. Individual mutants of the candidate CRD are engineered by standard methods. These mutant constructs are then iteratively assayed for (i) the retention of hGH and (ii) the secretion of hGH upon addition of a small molecule. Choice of small molecules to test, and their concentrations, are as described above. Assays on many mutants can be performed simultaneously by using multi-well plate assays.

Mutations can be chosen to optimize the likelihood of inducing a change in the properties of the protein that results in conditional retention. Mutations of particular interest are those anticipated to disrupt the efficient folding of the protein: such proteins might be subject to retention via the ER quality control system. Example mutations include gain-of-size mutations of side chains that constitute the hydrophobic core of the protein; and alterations of other residues of critical importance in secondary or tertiary structural features, such as glycine residues at beta-turn motifs. Other amino acids of interest are those that form, or are close to, the small molecule binding site. Mutants with reduced folding efficiency are preferred because such changes are most likely to be stabilized by binding of a small molecule, providing a mechanism for selective small molecule-mediated release of retained proteins. Thus, knowledge of the three-dimensional structure of a candidate CRD can be of great use in focusing mutagenesis to key positions.

Figure 10B:
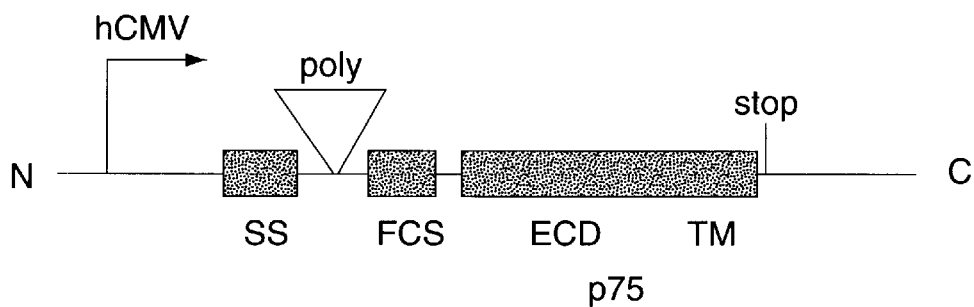
Figure 10C:
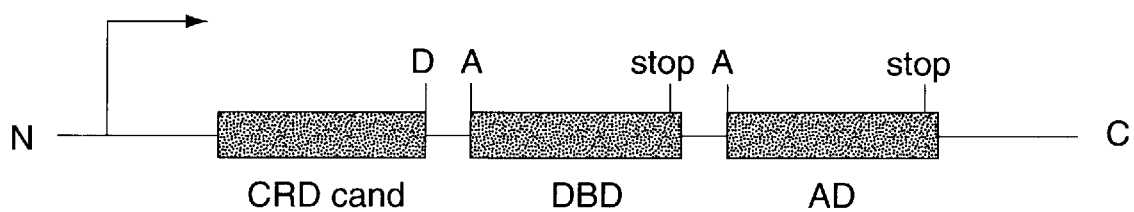

Both singly and multiply mutated proteins can be engineered and tested. Often, the best variant protein will be altered at several positions. Identifying the best combination of changes at multiple residues by iterative screening of mutants can be tedious and time-consuming. An alternative is the use of selection procedures, in which a large set of mutants is created and then subjected en masse to a selection step to identify the best mutants directly. See Clackson and Wells (Trends Biotech 1994 12: 173). To provide a means to directly select for proteins that act as CRDs, the expression vector described above is altered by exchanging the hGH coding sequence for DNA encoding a cell surface marker, such as CD2 or the p75 low affinity nerve growth factor receptor. The extracellular and transmembrane domains of cell surface marker are included, but most of the intracellular domain is preferably deleted to remove the potential for signaling through the receptor. A suitable expression vector using p75 is shown in FIG. 10B, where ECD and TM are respectively the extracellular and transmembrane domains of p75.

To select CRDs from a large set of candidates, genes encoding the candidates are ligated into the polylinker to create a library. The library is introduced into mammalian cells by established methods. Methods should ideally be chosen that (i) lead to a low number of ariants being introduced into each cell, so that the properties of variants can be tested individually, and (ii) provide stable introduction of the vector so that cells can be propogated and selected through multiple rounds. A preferred approach is therefore to construct the library in a retroviral vector followed by retroviral infection of cells, since this results single- or low-copy stable integration of the vector.

Selection of CRDs can be performed directly or indirectly. Direct screening is performed using a fluorescence-activated cell sorter, in two stages. In the first stage, cells harboring the library of CRD candidates are grown in culture and then incubated with a fluorescently-labeled antibody to the p75 ECD. Cells containing a clone for an active CRD will not bind, as p75 will be retained in the secretory apparatus.

However cells harboring ineffective CRDs will bind as the protein will not be retained. The labeled cells are sorted by FACS and cells that are not stained are gated and retrieved, and allowed to grow again in culture. The sort can optionally be repeated several times with a progressively higher gate, in order to isolate the cells expressing lowest levels of p75. In the second stage, a candidate CRD ligand (chosen as described above) is added and then the labeling process repeated. Now the cells with effective CRDs will be labeled, since the retained p75 will be released by the CRD ligand. The cells are sorted by FACS and the labeled cells are isolated. Again, the selection step can be repeated if desired. Once a suitable population of cells has been isolated, the variants that are conferring the CRD activity can be identified by isolating the genomic DNA of the cells followed by PCR amplification with primers located each side of the vector polylinker. The PCR products can then be cloned and sequenced. The ability of the identified variants to act as CRDs can be confirmed by cloning them individually into the hGH expression vector followed by testing as described earlier. Indirect screening may be accomplished by determining whether the CRD directs surface localization of a membrane protein which can then activate a signaling pathway.

The mutants introduced can be targeted to the residues of interest indicated earlier, or can randomly incorporated. Several suitable methods for engineering sets of multiple mutants have been described, including alanine-scanning mutagenesis (Cunningham and Wells (1989) Science 244 1081–1085), degenerate primer-mediated 'Kunkel' mutagenesis (See eg. Lowman and Wells 1993 J Mol Biol 234: 563–578), PCR misincorporation mutagenesis (see eg. Cadwell and Joyce (1992) PCR Meth. Applic. 2, 28–33), and DNA shuffling (Stemmer (1994) Nature 370 389–391).

3. CRDs that are Proteins that Self-aggregate in a Small Molecule-reversible Manner Methods to identify proteins that interact with one another are well known. A commonly used technique is the two-hybrid system, in which one partner is fused to a DNA binding domain and the other to an transcriptional activation domain. Interaction of the partners reconstitutes thae transcription factor, activating transcription of a reporter gene that can be identified by screening (eg. production of beta-galactosidase or SEAP) and/or that leads to cell survival and therefore provides a means for selecting for interacting partners (eg. his gene transcription in a his-strain of yeast). Two-hybrid assays can be performed in yeast or mammalian cells and methods are well known in the art.

A preferred embodiment is based on the vectors and cells described by Rivera et al. (Nature Med 1996 2, 1028–1032). Two expression vectors are constructed for chimeric transcription factors in which the candidate CRD is fused to the hybrid DNA domain ZFHD1 (in one case) and to an activiation domain of NF-kB p65 subunit, such as amino acids 361–550 (in the other). These vectors are transiently or stably transfected into mammalian cells, for example HT1080 cells, together with a SEAP reporter gene under the control of ZFHD1 binding sites. Aggregation of the candidate CRDs results in reconstitution of an active transcription factor and therefore prodiction of SEAP. Once a self-aggregating protein has been identified in this way, addition of candidate CRD ligand can be used to examine whether the aggregates can be dissociated with ligand. Reduction in the production of SEAP upon addition of ligand would indicate this activity. Any polypeptide can be chosen for testing in this way for CRD activity, but preferred proteins to try are those that already have known small molecule binding activity. In these cases the known binding ligands provide a starting point for choosing compounds that might disaggregate bound protein.

As before, an important additional configuration to explore is the concatenation of candidate CRDs. Presence of more than one aggregating domain may increase the apparent affinity of the aggregative interaction by virtue of the avidity effect.

Either natural or mutated proteins can be tested for CRD activity. Mutants of natural proteins are likely to provide good sources of CRDs as examples are known on the literature of aggregative activity induced by point mutations: for example sickle-cell hemoglobin, or alpha-1 antitrypsin as described earlier. Thus, large sets of mutants of a candidate protein can be cloned into two-hybrid vectors as described above, and tested for aggregative activity that can be reduced by addition of a small molecule. The criteria that dictate choice of positions to mutate will largely be the same as those described above for screening for CRDs directly in a secretion system (2 above); in addition, mutants that aggregate might be provided by converting polar surface residues to less polar amino ones. Single or multiple mutants can be engineered, using methods as described above.

Selection schemes for CRDs can also be devised. In these cases, libraries of mutant proteins are cloned into two hybrid vectors and analyzed en masse for CRD activity. These experiments are most easily performed in yeast and methods for two-hybrid selections are well known in the art. For example, expression vectors for mutants of candidate CRDs, fused to GAL4 DNA binding domain or activation domain vectors, and transformed into a his-deficient yeast reporter strain harboring a his gene under the control of GAL4 binding sites. Plating the library on his-deficient medium will result in growth only of cells that contain interacting CRDs on the two chimeric transcription factors. These positives can then be replica plated onto plates containing increasing amounts of candidate CRD ligands, to identify those CRDs whose interactions can be disrupted by small molecules. Such proteins are candidates for use as CRDs.

A complication with the above selection scheme is the desire to have the same mutant fused to both the DNA binding and activation domains, in order to identify proteins that self-aggregate. To achieve this, the expression vector for the chimeric proteins can be modified to allow a mutant gene to be joined to both transcription domains at the level of splicing. The domains of interest are encoded in separate exons. An outline of a suitable vector is shown in FIG. 10C. CRD cand is the candidate CRD: a library of candidates (eg mutant proteins) is inserted here. DBD and AD are the DNA binding and activation domains of a transcription factor. A and D indicate donor and acceptor splice sites. stop indicates a translational stop codon. By equipping the DBD with a suboptimal splice acceptor site, the CRD exon will be spliced to both DBD and AD exons. Thus, in each cell fusion proteins will be expressed in which the AD and DBD are both fused to an identical CRD candidate.

An alternative format for selection of self-aggregating proteins is the lambda repressor fusion system in *E.coli* (Hu et al. 1990 Science 250:1400–1403; for review see Hu 1995 Structure 3: 431–433). This strategy utilizes the fact that bacteriophage lambda repressor cI binds to DNA as a homodimer and that binding of such homodimers to operator DNA prevents transcription of phage genes involved in the lytic pathway of the phage life cycle. Thus, bacterial cells expressing functional lambda repressor are immune to lysis by superinfecting lambda bacteriophage. Repressor protein comprises an amino terminal DNA binding domain (amino acids 1–92) joined by a 40 amino acid flexible linker to a C-terminal dimerization domain. The isolated N-terminal domain binds very weakly to DNA sue to inefficient dimer formation. High affinity DNA binding can be restored by fusing the domain to a heterlogous dimerization domain, such as the GCN4 leucine zipper. A selection system is therefore possible in which phage immunity is used as a selection for interacting proteins.

For example, to select CRDs from a library of candidates, the candidates are cloned in frame with the repressor N-terminus and the library transformed into E.coli. Genes for proteins that aggregate are isolated from colonies that survive on plates containing high titers of lambda phage. These colonies can then be restreaked on to plates containing both lambda phage and candidate CRD ligand. If the ligand dissociates the aggregates, the E.coli will now no longer grow on these plates. Lambda repressor selection has several advantages for identifying CRDs, including the fact that the system is suitable for screening homodimers, and the large library sizes that can be obtained through the use of E.coli.

Another way to directly test whether a protein can act as a CRD in living cells is to fuse its coding sequence to green fluorescent protein (GFP) or variants thereof. Cells expressing such a fusion protein can then be examined directly by fluorescent microscopy to examine whether the CRD candidate appears to cause aggregates of the GFP. Candidate CRD ligands can then be added to determine whether the aggregates then dissociate. Once a CRD candidate has been identified by any of these methods, it can be tested for activity as a CRD by use of the methods outlined in section 1.

Pharmaceutical Compositions & Their Administration to Subjects Containing Engineered Cells Administration The ligand may be administered to a human or non-human subject using pharmaceutically acceptable materials and methods of administration. Various formulations, routes of administration, dose and dosing schedule may be used for the administration of ligand, depending upon factors such as the condition and circumstances of the recipient, the response desired, the biological half-life and bioavailability of the ligand, the biological half-life and specific activity of the target protein product, the number and location of engineered cells present, etc. The drug may be administered parenterally, or more preferably orally. For use in this invention, the most preferable route of administration are those in which a rapid onset of response occurs; such methods include, for example, sublingual, buccal, skin patch and inhalation. Dosage and frequency of administration will depend upon factors such as described above. The drug may be taken orally as a pill, powder, or dispersion; buccally; sublingually; injected intravascularly, intraperitoneally, subcutaneously; or the like. The drug may be formulated using conventional methods and materials well known in the art for the various routes of administration. The precise dose and particular method of administration will depend upon the above factors and be determined by the attending physician or healthcare provider.

The particular dosage of the drug for any application may be determined in accordance with conventional approaches and procedures for therapeutic dosage monitoring. A dose of the drug within a predetermined range is given and the patient's response is monitored so that the level of therapeutic response and the relationship of protein secretion over time may be determined. Depending on the expression levels observed during the time period and the therapeutic response, one may adjust the level of subsequent dosing to alter the resultant expression level over time or to otherwise improve the therapeutic response. This process may be iteratively repeated until the dosage is optimized for therapeutic response. Where the drug is to be administered chronically, once a maintenance dosage of the drug has been determined, one may conduct periodic follow-up monitoring to assure that the overall therapeutic response continues to be achieved.

In the event that the activation by the drug is to be reversed, administration of drug may be suspended so that cells return to a basal rate of secretion. To effect a more active reversal of therapy, an antagonist of the drug may be administered. An antagonist is a compound which binds to the drug or drug-binding domain to inhibit interaction of the drug with the fusion protein(s) and thus inhibit the downstream biological event. Thus, in the case of an adverse reaction or the desire to terminate the therapeutic effect, an antagonist can be administered in any convenient way, particularly intravascularly or by inhalation/nebulization, if a rapid reversal is desired.

Compositions

Drugs (i.e., the ligands) for use in this invention can exist in free form or, where appropriate, in salt form. The preparation of a wide variety of pharmaceutically acceptable salts is well-known to those of skill in the art. Pharmaceutically acceptable salts of various compounds include the conventional non-toxic salts or the quaternary ammonium salts of such compounds which are formed, for example, from inorganic or organic acids of bases. The drugs may form hydrates or solvates. It is known to those of skill in the art that charged compounds form hydrated species when lyophilized with water, or form solvated species when concentrated in a solution with an appropriate organic solvent.

The drugs can also be administered as pharmaceutical compositions comprising a therapeutically (or prophylactically) effective amount of the drug, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation. The pharmaceutical carrier employed may be, for example, either a solid or liquid.

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The drugs can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) may be used as an oral formulation for a variety of drugs for use in the practice of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the drug may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the drugs, or the various formulations thereof, including tablets, capsules, injectable solutions, encapsulation in liposomes, microparticles, microcapsules, etc. Preferred routes of administration to a patient are oral, sublingual, transdermal (patch), intranasal, pulmonary or bucal. Methods of introduction also could include but are not limited to dermal, intradermal, intramuscular, intraperitoneal, intravenous, subcutaneous, epidural, ocular and (as is usually preferred) oral routes. The drug may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For ex vivo applications, the drug will be delivered as a liquid solution to the cellular composition.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; rapamycin formulation for IV administration) and 0 648 494 (published Apr. 19, 1995; rapamycin formulation for oral ad iistration).

The effective dose of the drug will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. In embodiments in which the compound is rapamycin or an analog thereof with some residual immunosuppressive effects, it is preferred that the dose administered be below that associated with undue immunosuppressive effects.

The amount of a given drug which will be effective in the treatment or prevention of a particular disorder or condition will depend in part on the severity of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The drugs can also be provided in a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceutical or biological products, which notice reflects approval by the agency of manufacture, use or sale for human administration.

The full contents of all references cited in this document, including references from the scientific literature, issued patents and published patent applications, are hereby expressly incorporated by reference.

The following examples contain important additional information, exemplification and guidance which can be adapted to the practice of this invention in its various embodiments and the equivalents thereof. The examples are offered by way of illustration only and should not be construed as limiting in any way. As noted throughout this document, the invention is broadly applicable and permits a wide range of design choices by the practitioner.

The practice of this invention will employ, unless otherwise indicated, conventional techniques of cell biology, cell culture, molecular biology, transgenic biology, microbiology, recombinant DNA, immunology, virology, pharmacology, chemistry, and pharmaceutical formulation and administration which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells . H. Miller and M. P. Calos eds., 1987, Cold Spring Harbor Laboratory); Methods In Enzymology, Vols. 154 and 155 (Wu et al. eds.), Immunochernical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Generation of Domains and Vectors Used for Expression of F(36M) Fusion Proteins

A. Expression Vectors

Vectors for driving expression of fusion proteins were derived from the mammalian expression vector pCGNN (Attar and Gilman, MCB 12:2432–2443,1992). Inserts cloned as XbaI-BamHI fragments into pCGNN are transcribed under the control of the human CMV promoter and enhancer sequences (nucleotides −522 to +72 relative to the cap site), and are expressed with an N-terminal nuclear localization sequence (NLS; from SV40 T antigen) and epitope tag (a 16 amino acid portion of the *H. influenzae* hemaglutinin gene).

pCGNN was modified by site directed mutagenesis with oligonucleotides VR65, VR119, and VR120 to create pC$_4$EN. The resulting plasmid has unique restriction sites upstream of the CMV enhancer/promoter region (MluI) and between the promoter and protein coding region (EcoRI).

VR65: TCCCGCACCTCTTCGGCCAGCGaaTTc-cAGAAGCGCGTAT (SEQ ID NO. 2)

VR119: GACTCACTATAGGaCGcgTTC-GAGCTCGCCCC (SEQ ID NO. 3)

VR120: CATCATTTTGGCAAAGgATTCACTCCTCAGG (SEQ ID NO. 4)

Individual components of fusion proteins were generally produced as fragments containing an XbaI site immediately upstream of the first codon and a SpeI site, an in-frame stop codon, and a BamHI site immediately downstream of the last codon. Chimeric proteins comprising multiple components were assembled by stepwise insertion of XbaI-BamHI fragments into SpeI-BamHI-opened vectors or by insertion of XbaI-SpeI fragments into XbaI or SpeI-opened vectors.

B. F(36M) Domain

F(36M), in which the phenylalanine at amino acid 36 was changed to methionine, was created by mutagenizing a single FKBP domain, cloned into pCGNN with upstream XbaI and downstream SpeI and BamHI sites (Rivera et al., Nat. Med 2:1028–1032, 1996) with oligo VR1 to create pCGNN-F(36M). Two, 3, 4 and 6 tandem copies of F(36M) were created by the stepwise insertion of XbaI-BamHI fragments into SpeI-BamHI-opened vectors.

VR1: GATGGAAAGAAAatgGATTCCTCCCGG (SEQ ID NO. 5)

C. F(36M) Fusion Proteins: (FIG. 3)

(a) EGFP Fusions

EGFP coding sequence was amplified from pEGFP-1 (Clontech) with oligos VR2 and VR3. The resulting fragment, with upstream XbaI and downstream SpeI sites was inserted into pCGN, a derivative of pCGNN that lacks the SV40 nuclear localization sequence, to create pCGN-EGFP.

VR2: tctagaGTGAGCAAGGGCGAGGAG (SEQ ID NO. 6)

VR3: ggatccttaTTAACTAGTCTTGTA-CAGCTCGTCCATG (SEQ ID NO. 7)

F(36M)-EGFP fusions were created by inserting XbaI-SpeI fragments containing 3, 4 or 6 copies of F(36M) into the XbaI site of pCGN-EGFP to create pCGN-F(36M)3-EGFP, pCGN-F(36M)4-EGFP, and pCGN-F(36M)6-EGFP.

(b) hGH Gusions

An hGH cDNA (506–81) was obtained by RT-PCR amplification of RNA expressed from a cell line containing a genomic hGH gene (Rivera et al., Nat. Med 2:1028–1032, 1996) using oligos VR109 and VR110 to amplify the region from 40 bp upstream of the ATG to 60 bp after the stop codon. The resulting Hindll to EcoRI fragment was cloned into Z$_{12}$I-PL-2, a derivative of ZHWTx12-IL2-SEAP (Rivera et al., Nat. Med 2:1028–1032, 1996) in which the SEAP gene and SV40 early intron and polyadenylation signal were replaced by a polylinker and the SV40 late polyadenylation signal.

VR109: aagcttACCACTCAGGGTCCTGTGG (SEQ ID NO. 8)

VR110: gaattcGTGGCAACTTCCA (SEQ ID NO. 9)

To construct hGH fusion proteins, Z$_{12}$I-hGH-2 was mutagenized with oligos VR185, VR186, and VR187 to create i) an EcoRI site 32 bp upstream of the ATG, ii) an XbaI site immediately after the last amino acid of the signal sequence and iii) a Spe I site immediately after the last amino acid of hGH.

VR185: cacaggaccctGAATTCtaagcttgtggc (SEQ ID NO. 10)

VR186: ATAAGGGAATGGTtctagaGGCACTGCCCT (SEQ ID NO. 11)

VR187: atgccacccgggactagtGAAGCCACAGCTG (SEQ ID NO. 12)

Cloning the resulting EcoRI-SpeI fragment into pC$_4$EN produced pC$_4$S$_1$-hGH which expresses hGH from the CMV enhancer. The XbaI-BamHI fragment of pC$_4$S$_1$-hGH was then replaced by XbaI-SpeI fragments containing 2, 3, 4, or 6 copies of F(36M) and a SpeI-BamHI fragment encoding the furin cleavage site-hGH fusion to generate pC$_4$S$_1$-F(36M)-FCS-hGH fusions.

A SpeI-BamHI fragment encoding an FCS-hGH fusion protein was generated by amplification of the hGH cDNA with oligos VR4 and VR5.

VR4:actagtGCTAGAAACCGTCAGAAGAGATTCCCA ACCATTCCCTTAAGC (SEQ ID NO. 13)

VR5: ggatcccgggCTAGAAGCCACAGCTGCCCTC (SEQ ID NO. 14)

An XbaI-BamHI fragment containing the neo resistance gene downstream of the encephalomyocarditis virus internal ribosome entry sequence (IRES/Neo; Amara et al PNAS 94:10618–23, 1997) was inserted into appropriate SpeI-BamHI-opened vectors to generate pC$_4$S$_1$-F(36M)-FCS-hGH/neo and pC$_4$S$_1$-hGH/neo vectors.

(c) Insulin Fusions

A human insulin cDNA was obtained by RT-PCR amplification of human pancreas polyA+ RNA (Clontech) using oligos VR220 and VR221 to amplify the region from 9 bp upstream of ATG (EcoRI) to 13 bp after stop codon (BamHI). The resulting EcoRI-BamHI fragment was cloned into pC$_4$EN to generate pC$_4$-hIn.

VR220: cGAATTCttctgccATGGCCCTGTGGATGCGC (SEQ ID NO. 15)

VR221: cGGATCCgcaggctgcgtCTAGTTGCAGTAG (SEQ ID NO. 16)

A SpeI-BamHI fragnent encoding an furin cleavage sequence-insulin fusion protein was generated by RT-PCR amplification with oligos VR222 and VR221.

VR222: cACTAGTGCTAGAAACCGTCAGAA-GAGATTTGTGAACCAACACCTGTGCGGC (SEQ ID NO. 17)

VR221: cGGATCCgcaggctgcgtCTAGTTGCAGTAG (SEQ ID NO. 18)

The wild type insulin gene and FCSinsulin fusion were mutagenized to i) alter amino acid B10 to Asp, ii) create a FCS at the B-C junction, and iii) create a FCS at the C-A junction, using oligos VR223, VR224, VR225, respectively.

VR223: CCTGTGCGGCTCAgACCTGGTGGAAGC (SEQ ID NO. 19)

VR224: CTTCTACACACCCAgGACCaagCGGGAG-GCAGAGG (SEQ ID NO. 20)

VR225: CCCTGGAGGGGTCCCgCAGAAGCGTGGC (SEQ ID NO. 21)

Mutation of pC$_4$-hIn produced pC$_4$-hIn-m3. The mutated FCS-insulin fusions were used to replace the FCS-hGH portion of the pC$_4$S$_1$-F(36M)-FCS-hGH fusions to create pC$_4$S$_1$-F(36M)-FCS-hIn-m3 fusions.

(d) LNGFR Fusions

EcoRI-SpeI fragments containing amino acids 1–274 of the human low affinity nerve growth factor receptor (LNGFR; Clackson et al., PNAS 95:10437–42, 1998) and SpeI-BamHI fragments containing 3, 4, or 6 copies of F(36M) were cloned into pC$_4$EN to generate pC$_4$LNGFR-F(36M) fusions.

(c) Transcription Factor Fusions pCGNN-ZFHD1-F(36M) and pCGNN-F(36M)-p65 fusion proteins were generated as described for wild type FKBP fusions (Amara et al PNAS 94:10618–23, 1997).

An XbaI-SpeI fragment containing 6 copies of F(36M) was inserted into the XbaI or SpeI site of pCGNN-ZFHD1-p65 to generate pCGNN-F(36M)6-ZFHD1-p65 and pCGNN-ZFHD1-p65-F(36M)6.

pCGNNZFHD1

An expression vector for directing the expression of ZFHD1 coding sequence in mammalian cells was prepared as follows. Zif268 sequences were amplified from a cDNA clone by PCR using primers 5'Xba/Zif and 3'Zif+G. Oct1 homeodomain sequences were amplified from a cDNA clone by PCR using primers 5'Not Oct HD and Spe/Bam 3'Oct. The Zif268 PCR fragment was cut with XbaI and NotI. The OctI PCR fragment was cut with NotI and BamHI. Both fragments were ligated in a 3-way ligation between the XbaI and BamHI sites of pCGNN (Attar and Gilman, 1992) to make pCGNNZFHD1 in which the cDNA insert is under the transcriptional control of human CMV promoter and enhancer sequences and is linked to the nuclear localization sequence from SV40 T antigen. The plasmid pCGNN also contains a gene for ampicillin resistance which canserve as a selectable marker.

pCGNNZFHD1-p65

An expression vector for directing the expression in mammalian cells of a chimeric transcription factor containing the composite DNA-binding domain, ZFHD1, and a transcription activation domain from p65 (human) was prepared as follows. The sequence encoding the C-terminal region of p65 containing the activation domain (amino acid residues 450–550) was amplified from pCGN-p65 using primers p65 5' Xba and p65 3' Spe/Bam. The PCR fragment was digested with Xba1 and BamH1 and ligated between the the Spe1 and BamH1 sites of pCGNN ZFHD1 to form pCGNN ZFHD-p65AD.

The P65 transcription activation sequence contains the following linear sequence:
CTGGGGGCCTTGCTTGGCAACAGCACA-
GACCCAGCTGTGTTCACAGACCTG-
GCATCCGTCGACAACTCCGAGTTTCAG-
CAGCTGCTGAACCAGGGCATACCTGTGGCCCCC
CACACAACTGAGCCCATGCTGATGGAG-
TACCCTGAGGCTATAACTCGCCTAGTGA-
CAGGGGCCCAGAGGCCCCCCGAC-
CCAGCTCCTGCTCCACTGGGGGCCCGGGGCT
CCCCAATGGCCTCCTTTCAGGAGATGAA-
GACTTCTCCTCCATTGCGGACATGGACT-
TCTCAGCCCTGCTGAGTCAGATCAGCTCC (SEQ ID NO. 22)

Example 2

Identification and Synthesis of a Ligand for the Conditional Retention Domain F36M FKBP AP21998 and AP22542 are ligands of FKBP that have particular utility for CAD applications, because they bind with high affinity to F36M-FKBP but poorly to the wild-type protein, and are thus anticipated to lead to minimal interactions with the endogenous proteins during in vivo applications. The design and assay of such "bumped" ligands that target a hole created by truncating FKBP residue Phe36 have been described (Clackson et al., Proc. Natl. Acad. Sci. USA 95:10437–10442, 1998).

AP 21998 was prepared via DCC/DMAP-mediated coupling of the previously described acid AP 1867 (compound 5S in Clackson et al., Proc. Natl. Acad. Sci. USA 95:10437–10442, 1998) with commercially available N,N-dimethyl-1,3-propanediamine (Scheme 1). AP 22542 was also synthesized by a DCC/DMAP-mediated coupling of acid AP 17362 with alcohol 3 (Scheme 2). Carbinol 3 itself was prepared via a three step sequence as outlined in Schene 2. The Claisen-Schmidt condensation of 3,4- dimethoxybenzaldehyde and 3-acetylpyridine provided unsaturated ketone 1 as a crystalline solid in 68% yield. Transfer hydrogenation of 1 utilizing ammonium formate as a hydrogen source provided the propanone adduct 2 as a crystalline solid in 50% isolated yield. Finally, the enantioselective reduction of the aryl ketone moiety of 2 to the desired R-configured carbinol 3 was achieved in 86% by reduction of 2 with (+)-b-chlorodiisopinocamphenylborane (DIP-Chloride™) (Chandrasekharan et al. J. Org. Chem. 50:5446, 1985). The synthesis of the acid component, AP 17362, was prepared as described in Scheme 3. The commercially available 3,4,5-trimethoxyphenylacetic acid was converted to the racemic 2-arylbutane derivative 4 in 83% yield by alkylation with iodoethane of the NaHMDS-generated dianion of 3,4,5-trimethoxyphenylacetic acid in THF at 0° C. Resolution of the acid by repetitive crystallization of the (−)-cinchonidine salt afforded optically enhanced 4S in 24% yield (48% theoretical) and of 91% ce. This resolved acid was then coupled with methyl-L-pipecolate hydrochloride by use of 2-chloro-1-methylpyridinium iodide (Mukaiyama's Reagent). The resulting coupled product was not isolated, but subjected to hydrolysis to afford the desired crystalline acid, AP 17362, in 42% overall yield and >99% de. X-ray structural analysis confirmed the absolute stereochemistry of the resolved 2-arylbutane center as the S configuration.

SCHEME 1

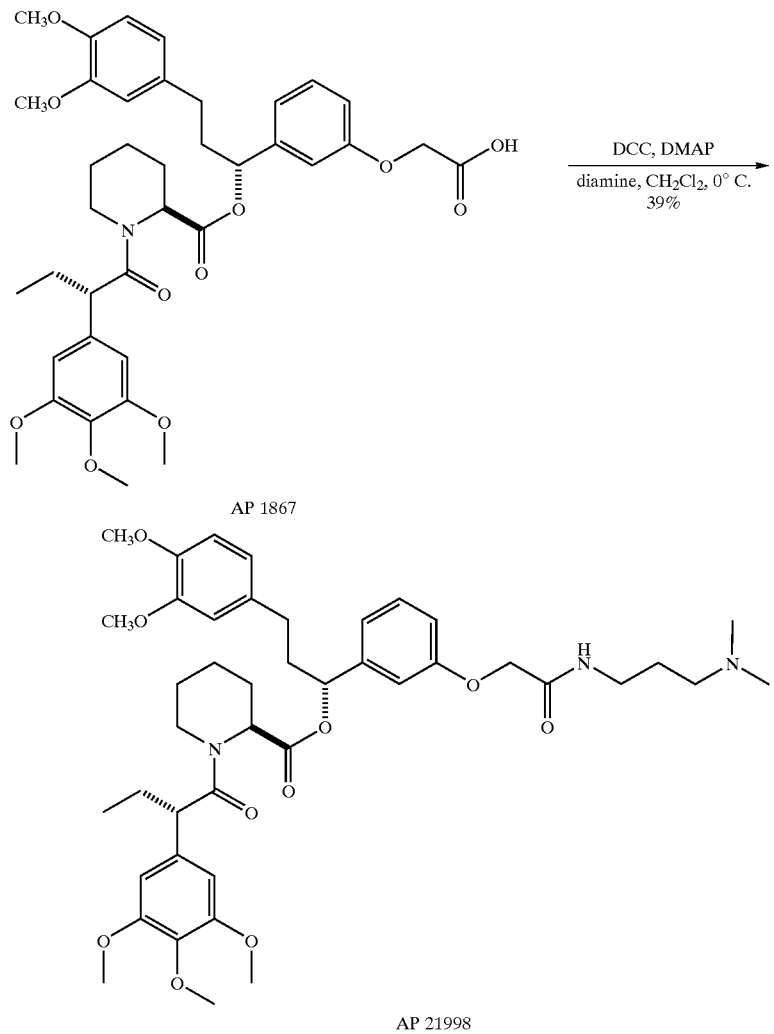

AP 1867

AP 21998

AP 21998: A solution of AP 1867 (5.0 g, 7.21 mmol) in CH2Cl2 (5.0 mL) at 0° C. was treated with DCC (178 mg, 0.79 mmol) followed 30 min later by N,N-dimethyl-1,3-propanediamine (880 mg, 8.65 mmol) and DMAP (5 mg). The reaction mixture was allowed to warm to room temperature and stir for 5 h, after which time the reaction mixture was diluted with EtOAc (50 mL), filtered, and the filtrate extracted with a 5% aqueous citric acid solution (3×20 ml). The acid extract was then made basic by the addition of solid NaHCO3 and extracted with EtOAc (3×50 mL). The organic extract was dried over Na2SO4, filtered, and evaporated to afford a crude material which was flash chromatographed on silica gel (5% then 15% MeOH/CH2Cl2) to afford product (2.2 g, 39%) as a colorless foam: IR (neat) 2940, 1735, 1650, 1510, 1460, 1240, 1130 cm$^{-1}$; $^1$H NMR (CDCl3, 300 MHz) 7.78 (br t, J=5.1 Hz, 1 H), 7.19 (t, J=8.6 Hz, 1 H), 6.92–6.65 (m, 6 H), 6.42 (s, 2 H), 5.63 (dd, J=8.0, 5.5 Hz, 1 H), 5.45 (d, J=4.1 Hz, 1 H), 4.49 (s, 2 H), 3.86–3.70 (m, 16 H), 3.60 (t, J=7.0 Hz, 1 H), 3.47–3.41

(m, 2 H), 2.82 (td, J=13.2, 2.4 Hz, 1 H), 2.62–2.29 (m, 12 H), 2.16–1.23 (m, 10 H), 0.90 (t, J=7.3 Hz, 3 H); $^{13}$C NMR (CDCl3, 75 MHz) 172.7, 170.6, 168.5, 157.5, 153.2, 148.9, 147.4, 142.3, 136.7, 135.3, 133.4, 129.8, 120.2, 119.6, 113.9, 112.8, 111.8, 111.4, 105.1, 75.7, 67.3, 60.8, 56.3, 56.0, 52.1, 50.7, 44.3, 43.5, 38.3, 37.4, 31.3, 28.3, 26.8, 25.5, 25.4, 20.9, 12.5; LRMS (ES+): (M+H)$^+$ 778; HRMS (FAB): (M+H)$^+$ calcd: 778.4278, meas: 778.4299.

SCHEME 2

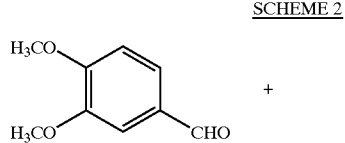

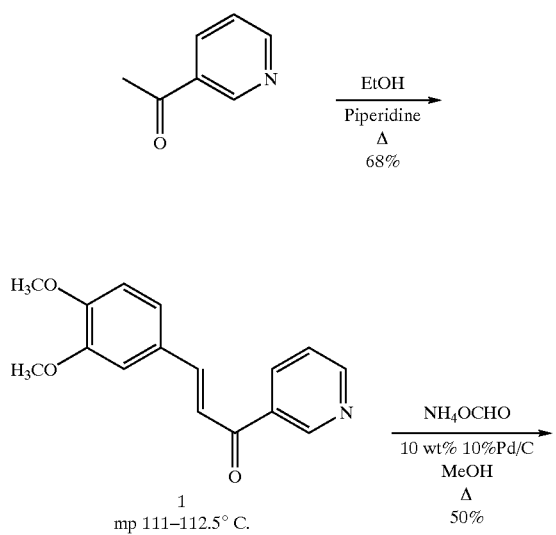

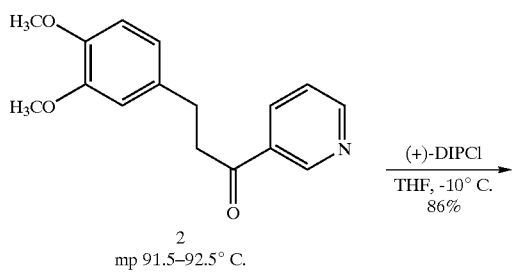

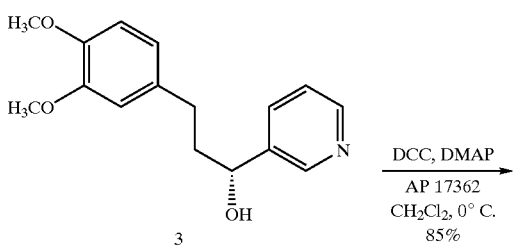

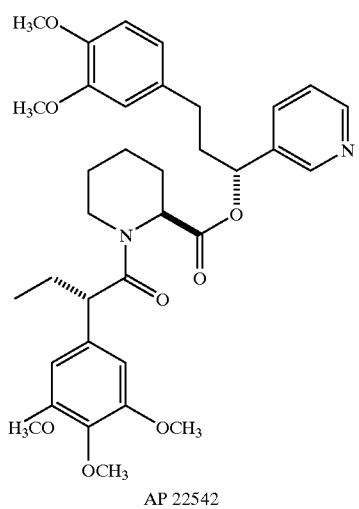

AP 22542

(E)-3-(3,4-Dimethoxyphenyl)-1-pyridin-3-yl-propenone (1): A solution of 3,4-dimethoxybenzaldehyde (53.7 g, 323 mmol) and 3-acetylpyridine (39.1 g, 323 mmol) in EtOH (400 mL) was treated with piperdine (4.75 mL, 48 mmol) and heated at reflux for 4 days. The reaction was then evaporated to a slurry and treated with water (400 mL). The resulting solids were filtered, air dried, and recrystallized from EtOAc/hexane to afford product (59.2 g, 68%) as a yellow colored solid: mp 111–112.5° C.; TLC (EtOAc) Rf=0.30; 1H NMR (CDCl3, 300 MHz) 9.23 (d, J=1.8 Hz, 1 H), 8.79 (dd, J=4.8, 1.7 Hz, 1 H), 8.28 (dt, J=7.9, 1.9 Hz, 1 H), 7.79 (d, J=15.6 Hz, 1 H), 7.46–7.42 (m, 1 H), 7.35 (d, J=15.6 Hz, 1 H), 7.24 (dd, J=8.3, 1.9 Hz, 1 H), 7.68 (d, J=1.9 Hz, 1 H), 6.91 (d, J=8.3 Hz, 1 H), 3.95 (s, 3 H), 3.93 (s, 3 H); 13C NMR (CDCl3, 75 MHz) 189.0, 152.9, 151.9, 149.7, 149.4, 146.1, 135.8, 133.8, 127.5, 123.6, 119.4, 111.2, 110.2, 56.0; LRMS (ES+) (M+H)+ 270; Anal. Calcd for C16H15NO3: C, 71.36; H, 5.61; N, 5.20. Found: C, 71.13; H, 5.70; N, 4.95.

3-(3,4-Dimethoxyphenyl)-1-pyridin-3-yl-propan-1-one (2): A solution of olefin 1 (20.0 g, 74.2 mmol), wet 10% Pd/C (2.0 g), and ammonium formate (14.0 g, 222 mmol) in MeOH (400 mL) was heated at reflux for 30 min and filtered, while hot, through a pad of Celite. The filtrate was allowed to slowly cool and the resulting solids were filtered and air dried to afford product (10.0 g, 50%) as a colorless solid: mp 91.5–92.5° C.; TLC (EtOAc) Rf=0.55; 1H NMR (CDCl3, 300 MHz) 9.16 (d, J=2.0 Hz, 1 H), 8.76 (dd, J=4.8, 1.7 Hz, 1 H), 8.21 (dt, J=8.0, 1.9 Hz, 1 H), 7.40 (dd, J=7.9, 4.8 Hz, 1 H), 6.83–6.77 (m, 3 H), 3.87 (s, 3 H), 3.85 (s, 3 H), 3.30 (d, J=7.3 Hz, 2 H), 3.03 (d, J=7.7 Hz, 2 H); 13C NMR (CDCl3, 75 MHz) 198.2, 153.5, 149.6, 149.0, 147.6, 135.3, 133.4, 132.1, 123.6, 120.2, 111.9, 111.5, 56.0 (2), 40.9, 29.5;

Anal. Calcd for C16H17NO3: C, 70.83; H, 6.32; N, 5.16. Found: C, 70.63; H, 6.42; N, 5.05.

(R)-3-(3,4-Dimethoxyphenyl)-1-pyridin-3-yl-propan-1-ol (3): A solution of (+)-DIP-Chloride™ (7.09 g, 22.1 mmol) in THF (10 mL) at −25° C. was treated with ketone 2 (2.0 g, 7.37 mmol). The resulting mixture was allowed to stand in at −20° C. for 2 h then placed in a −10° C. freezer for 48 h, after which time the mixture was concentrated and treated with diethyl ether (50 mL) followed by diethanolamine (4.24 mL, 44.2 mmol). The viscous mixture was allowed to stir at room temperature for 6 h after which time it was filtered through a pad of Celite with the aid of diethyl ether. The filtrate was concentrated and the crude material flash chromatographed (EtOAc then 10% MeOH/EtOAc) to afford product. The product was redissolved in diethyl ether (50 mL) and again treated once again with diethanolamine (2.12 mL, 22.1 mmol) as described above to afford product (1.74 g, 86%) as a clear colorless oil (96% ee by Chiralpak AD HPLC, 15% EtOH/hexane, retention time 6.1 min for the S-enantiomer and 19.4 min for the desired R-enantiomer): TLC (EtOAc) Rf=0.25; IR (neat) 3210, 2935, 1590, 1515, 1465, 1420, 1260, 1155, 1070, 1030, 1030 cm−1; 1H NMR (CDCl3, 300 MHz) 8.50 (d, J=1.7 Hz, 1 H), 8.44 (dd, J=4.7, 1.5 Hz, 1 H), 7.71 (dt, J=7.8, 1.7 Hz, 1 H), 7.28–7.24 (m, 1 H), 6.80–6.70 (m, 1 H), 4.72 (dd, J=7.9, 5.2 Hz, 1 H), 3.85 (s, 6 H), 3.21 (br s, 1 H), 2.77–2.9 (m, 2 H), 2.18–1.96 (m, 2 H); 13C NMR (CDCl3, 75 MHz) 149.0, 148.6, 147.7, 147.4, 140.3, 134.0, 133.8, 123.6, 120.2, 111.8, 111.4, 71.3, 56.0, 55.8, 40.7, 31.5; LRMS (ES+) (M+H)+ 274; HRMS (ES+): (M+H)+ calcd: 274.1462, meas: 274.1443.

1-[2(S)-(3,4,5-trimethoxyphenyl)-butyryl]-piperdine-2(S)-carboxylic acid, 3-(3,4-Dimethoxyphenyl)-1-pyridin-3-yl-propan-1(R)-ol ester (AP22542): A solution of alcohol 3

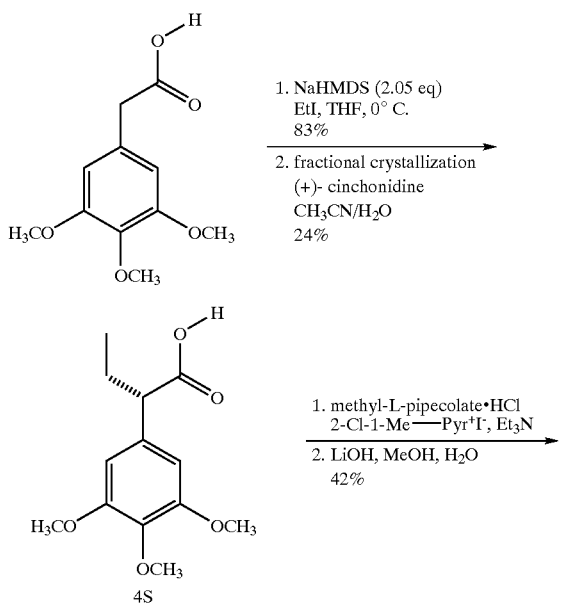

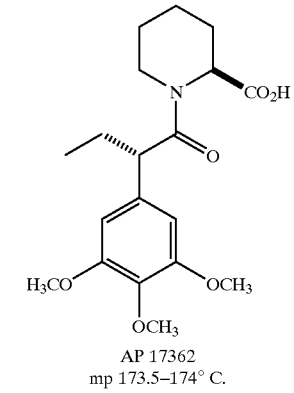

AP 17362
mp 173.5–174° C.

(600 mg, 2020 mmol), acid AP17362 (882 mg, 2.42 mmol), and DMAP (2.41 mg, 1.98 mmol) in CH2Cl2 (2.5 mL) at −10° C., was treated with DCC (498 mg, 2.42 mmol). The mixture was allowed to warm to 5° C. over a 1 h period and then placed in a 5° C. refrigerator for an additional 16 h. The reaction mixture was then diluted with EtOAc (3 mL), filtered, evaporated, and the crude material flash chromatographed (75% then 100% EtOAc/hexane) to afford product (1.15 g, 85%) as a colorless foam: TLC (EtOAc) Rf=0.40; IR (neat) 2940, 1740, 1645, 1590, 1515, 1455, 1420, 1240, 1130, 1030 cm−1; 1H NMR (CDCl3, 300 MHz) 8.50 (dd, J=4.6, 1.5 Hz, 1 H), 8.42 (d, J=1.7 Hz, 1 H), 7.27 (d, J=8.6 Hz, 1 H), 7.19 (dd, J=7.7, 4.7 Hz, 1 H), 6.78 (d, J=7.7 Hz, 1 H), 6.66–6.64 (m, 2 H), 6.46 (s, 2 H), 5.69 (dd, J=7.7, 6.0 Hz, 1 H), 5.47 (d, J=4.3 Hz, 1 H), 3.86–3.73 (m, 16 H), 3.59 (t, J=7.1 Hz, 1 H), 2.72 (td, J=13.2, 2.6 Hz, 1 H), 2.60–2.38 (m, 2 H), 2.30 (d, J=12.4 Hz, 1 H), 2.16–2.02 (m, 2 H), 1.99–1.90 (m, 1 H), 1.79–1.57 (m, 4 H), 1.46–1.37 (m, 1 H), 1.32–1.19 (m, 1 H), 0.90 (t, J=7.3 Hz, 3 H); 13C NMR (CDCl3, 75 MHz) 172.6, 170.5, 153.3, 149.5, 149.0, 148.3, 147.5, 136.9, 135.6, 135.3, 133.8, 1323.0, 123.6, 120.2, 111.7, 111.5, 105.1, 73.6, 60.9, 56.1, 56.0, 52.0, 50.7, 43.5, 37.9, 31.1, 28.3, 26.7, 25.3, 20.9, 12.5; LRMS (ES+) (M+H)+ 621; HRMS (FAB): (M+H)+ calcd: 621.3176, meas: 621.3178.

Scheme 3

(R/S)-2-(3,4,5-Trimethoxyphenyl)butyric acid: A solution of of 3,4,5-trimethoxyphenylacetic acid (40.0 g, 176.8 mmol) in THF (125 mL) at 0° C. was treated dropwise with a 2N THF solution of sodium bis(trimethylsilyl)amide (181 mL, 362 mmol, Lancaster) over a 1 h period keeping the internal reaction temperature below 8° C. After 15 min, iodoethane (14.9 mL, 185.7 mmol) was added slowly over a 30 min period keeping the internal reaction temperature below 6–8° C. and the solution allowed to warm to room temperature. After 2 h, the mixture was poured onto EtOAc (700 mL) and acidified by slow addition of a 2.0 N HCl solution (325 mL). The organic component was further washed with a saturated sodium bisulfite solution (50 mL) followed by brine (2×50 mL), then dried over anhydrous Na2SO4, and concentrated to a waxy residue (43.8 g). The crude product was recrystallized from hot EtOAc/hexane (30 mL/30 mL) to afford product (37.1 g, 83%): mp 103–104° C.; TLC (AcOH/EtOAc/hexane, 2:49:49) Rf=0.50.

(S)-2-(3,4,5-Trimethoxyphenyl)butyric acid (4S): A solution of 4 (3.09 g, 12.15 mmol) in CH3CN (130 mL) was treated with (−)-cinchonidine (3.58 g, 12.15 mmol) and the mixture heated to reflux. The homogeneous solution was allowed to slowly cool to room temperature with concomitant formation of salts. After a period of 1 h at room temperature, the solution was cooled to 0° C. for 30 minutes and the solution then filtered to afford 4.05 g of a chalky colorless solid. This recrystalliztion procedure was then carried out an addition four times utilizing ~20 mL CH3CN/g of salt. The diastereomeric salt isolated from the fifth crystallization (1.64 g) was suspended in EtOAc (100 mL) and treated with a 10% aqueous HCl solution (10 mL). The organic phase was then washed with water (2×15 mL) followed by brine 10 mL), dried over anhydrous MgSO4, and concentrated to afford product (0.75 g, 24%) as a colorless solid (91% ee by Chiralcel OD HPLC, 1:5:94 formic acid/i-PrOH/hexane, retention time 19.6 min for the R-enantiomer, and 22.1 min for the desired S-enantiomer): mp 84–85° C. (99.1% ee material); [a]22D +54.8 (c=1.07, MeOH, 30 min, 99.1% ee material); UV (MeOH) lmax 270 (e 895), 232 (e 7,440), 207 (e 40,994) nm; 1H NMR (DMSO-d6, 300 MHz) 6.34 (s, 2 H), 3.52 (s, 6 H), 3.40 (s, 3 H), 3.11 (t, J=7.6 Hz, 1 H) 1.76–1.36 (m, 1 H), 0.60 (t, J=7.3 Hz, 3 H); 1H NMR (CD3OD, 300 MHz) 6.78 (s, 2 H), 4.00 (s, 6 H), 3.90 (s, 3 H), 3.55 (t, J=7.7 Hz, 1 H) 2.24–2.12 (m, 1 H), 1.97–1.83 (m, 1 H), 1.07 (t, J=7.3 Hz, 3 H); 13C NMR (DMSO-d6, 75 MHz) 175.1, 153.1, 136.9, 135.8, 105.4, 60.3, 56.2, 53.1, 26.7, 12.4; 13C NMR (CD3OD, 75 MHz) 178.1, 154.9, 138.7, 137.4, 106.8, 61.5, 57.0, 55.3, 28.3, 12.9; HRMS (FAB): (M–H)– calcd: 253.1076, meas: 253.1063. Anal. Calcd for C13H18O5: C, 61.41; H, 7.13. Found: C, 61.47; H, 7.20.

[S-(R*,R*)]-1-[1-oxo-2-(3,4,5-trimethoxyphenyl)butyl]-2-piperdinecarboxylic acid (AP17362): A solution of 5 (0.75 g, 2.95 mmol, 91% ee) in CH2Cl2 (15 mL) was treated with methyl-L-pipecolate hydrochloride (0.539 g, 3.00 mmol) followed by 2-chloro-1-methylpyridinium iodide (0.958 g, 3.75 mmol) and triethylamine (1.25 mL, 8.95 mmol). The reaction mixture was allowed to stir for 3.5 h, after which time the solution was diluted with EtOAc (100 mL), washed with water (15 mL), a 5% aqueous citric acid solution (25 mL), a saturated Na2CO3 solution (10 mL), water (15 mL), and finally brine (15 mL). The organic phase was dried over MgSO4 and concentrated to a yellow oil which was then dissolved in MeOH (14 mL). The methanolic solution was treated with water (1 mL) followed by lithium hydroxide monohydrate (0.620 g, 14.78 mmol). After 4 h, the mixture was diluted with EtOAc (100 mL), washed with a saturated NaHCO3 solution (3×40 mL) followed by water (20 mL). The aqueous portions were combined and acidified to pH ~3 by careful addition of a 10% aqueous HCl solution. The resulting suspension was extracted with EtOAc (2×75 mL) which was then washed with water (2×25 mL), brine (20 mL), dried over MgSO4, and concentrated to a solid which was dissolved in a refluxing EtOAc (75 mL) solution and allowed to slowly cool to room temperature. The resulting crystalline material was filtered and air dried to afford product (0.508 g, 42%) as a colorless solid: (+99% de by Chiralpak AD HPLC with guard column, 0.2:5:95 formic acid/i-PrOH/hexane, retention time 40.0 min for the SR-diastereomer, 43.0 min for the desired SS-diastereomer, 46.5 min for the RR-diastereomer, and 67.5 min for the RS-diastereomer); mp 173.5–174° C.; [a]22D +10.9 (c=1.01, DMSO, 30 min); UV (MeOH) lmax 270 (e 990), 232 (e 11,161), 207 (e 49,079) nm; 1H NMR (DMSO-d6, 300 MHz) 6.55 (s, 2 H), 5.13 (d, J=4.4 Hz, 1 H), 3.85–3.64 (m, 11 H), 2.77–2.70 (m, 1 H), 2.12 (d, J=13.4 Hz, 1 H), 1.99–1.85 (m, 1 H), 1.65–1.55 (m, 4 H), 1.38–1.18 (m, 2 H), 0.84 (t, J=7.2 Hz, 3 H); 1H NMR (CD3OD, 300 MHz) 6.74 (s, 2 H), 5.43 (d, J=4.0 Hz, 1 H), 4.13–3.83 (m, 11 H), 3.03 (td, J=13.5, 3.0 Hz, 1 H), 2.44 (d, J=13.8 Hz, 1 H), 2.24–2.14 (m, 1 H), 1.90–1.40 (m, 6 H) 1.09 (t, J=7.3 Hz, 3 H); 13C NMR (DMSO-d6, 75 MHz) 172.9, 172.2, 153.0, 136.2, 105.4, 60.2, 56.2, 56.0, 51.8, 49.4, 43.1, 28.5, 26.8, 25.3, 21.0, 12.8; 13C NMR (CD3OD, 75 MHz) 175.4, 174.5, 154.9, 137.5, 106.8, 61.5, 57.1, 53.9, 52.1, 45.2, 29.9, 28.2, 26.8, 22.3, 13.2; HRMS (FAB): (M–H)– calcd: 364.1760, meas: 364.1774. Anal. Calcd for C19H2706: C, 62.45; H, 7.45; N, 3.83. Found: C, 62.32; H, 7.61; N, 3.88.

Example 3

The Conditional Retention Domain F(36M) FKBP; Studies with hGH

Figure 2A:
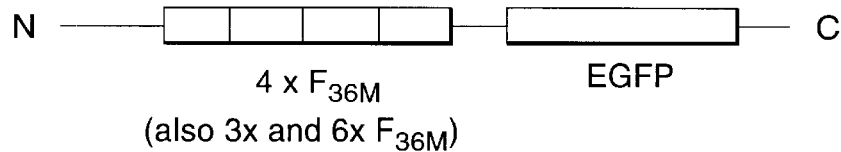
FIG. 2A: F36M-EGFP fusion proteins.
Figure 2B:
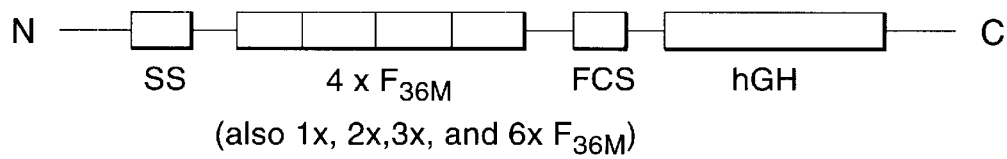
FIG. 2B: F36M- hGH fusion proteins.

To test whether F(36M) could function as a conditional retention domain to enable regulated secretion of a fused heterologous protein, a fusion protein of the design shown in FIG. 2B was constructed. This fusion protein contains a signal sequence from the human growth hormone (hGH) gene, 4 copies of the F(36M) domain, a furin cleavage sequence from human stromelysin 3 and coding sequence from the mature hGH protein. The resulting fusion protein, in essence, simply contains F(36M) domains and a furin cleavage signal inserted at the cleavage site between the signal sequence and the mature hGH peptide sequence. Since the furin recognition sequence is N-terminal to the cleavage site it can be situated so that appropriate cleavage will generate the same hGH amino acid sequence as that generated by natural cleavage of its own signal sequence.

Figure 3A:
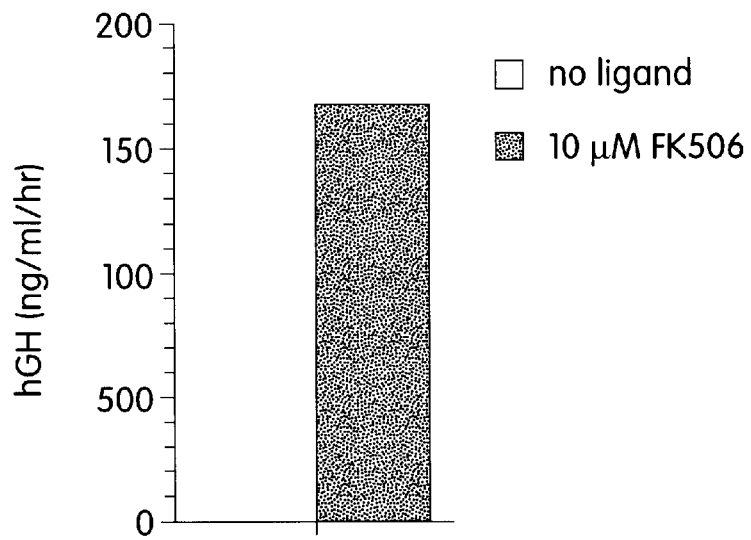
FIG. 3: Ligand dependent secretion of hGH. Levels of hGH secreted into the culture medium of transiently transfected (FIG. 3A) or stably transfected (FIG. 3B) HT1080 cells in the absence and presence of ligand.
FIG. 3E). Surface expression was assessed by FACS analysis using anti-LNGFR antibodies.
Figure 3B:
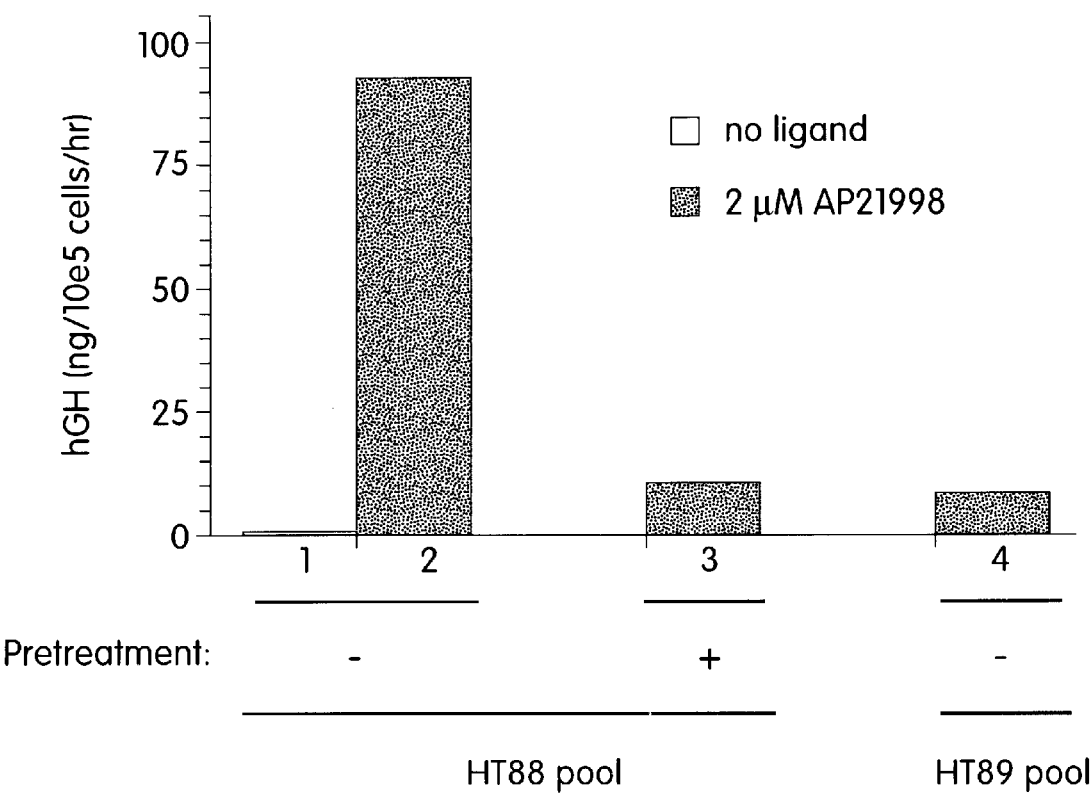

A vector driving the expression of this fusion protein, under control of the strong constitutive enhancer from CMV, was transiently transfected into HT1080 cells, a human fibrosarcoma cell line. Following overnight incubation of cells in the absence of ligand, the medium was washed away and fresh medium added, with or without ligand. Two hours later, the amount of hGH secreted into the medium was determined by radioimmunoassay. As shown in FIG. 3A, in the absence of ligand, the amount of hGH secreted was low. In contrast, in the presence of ligand, the amount of hGH secreted was several hundred-fold greater. This demonstrates that F(36M) can act as a conditional retention domain when fused to a heterologous protein.

Next, cell lines were generated by stably transfecting the F(36M)-hGH expression vector into HT1080 cells. For comparison, the native hGH gene driven by the same CMV enhancer was also stably transfected into cells. To allow an initial assessment of any potential toxic effects of the retained fusion protein, the selectable marker was expressed from the same transcript as the wt hGH or F(36M)-hGH fusion proteins through the use of an internal ribosome entry signal. Equivalent numbers of clones were obtained, suggesting the there was no toxic effect of the fusion protein.

Pools of clones stably transfected with the F(36M)-hGH fusion protein (HT88 pool) were analyzed as described for the transiently transfected cells. As shown in FIG. 3B, once again, hGH secretion, which is very low in the absence of ligand, is induced several hundred fold by incubation with ligand for two hours. To determine the constitutive rate of hGH secretion, the amount of hGH secreted in the presence of ligand was measured from cells that had already been exposed to ligand for 15 hours. As shown in lane 3, the constitutive rate of secretion from the HT88 cell line was very similar to the rate of secretion from the HT89 cell line which had been stably transfected with the wild type hGH protein (lane 4). Thus, in the presence of ligand the F(36M) domains have no detectable "retention" activity. Furthermore, this shows that in the absence of ligand,, the fusion protein accumulates to levels approximately 10-fold higher than that seen when secretion is not blocked. This steady state level of stored F(36M)-hGH fusion protein can persist for months in the cell line with no apparent toxic effect.

Example 4
Localization/Cleavage of Fusion Protein

Figure 2C:
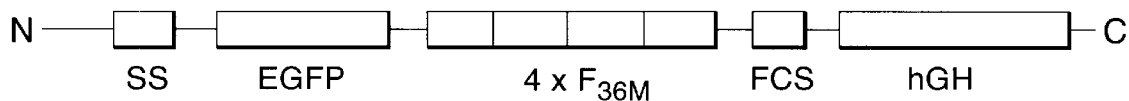
FIG. 2C: EGFP-F36M-hGH fusion proteins.
Figure 2D:
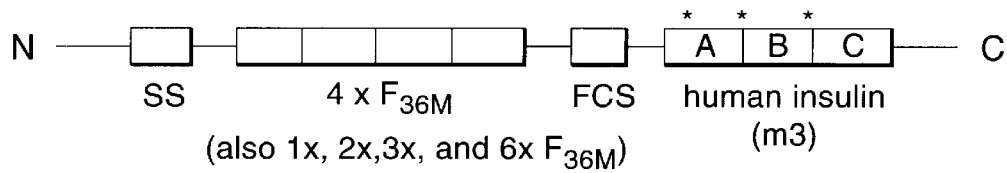
FIG. 2D: F36M-insulin fusion proteins.
Figure 2E:
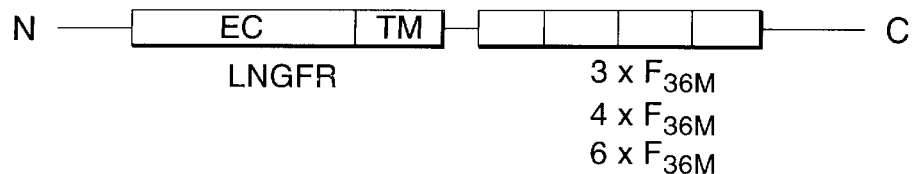
FIG. 2E: LNGFR-F36M fusion proteins.

To analyze the localization of the fusion protein, EGFP coding sequence was incorporated in the fusion protein as shown in FIG. 2C. In cells stably transfected with this fusion protein, in the absence of ligand, the fusion protein was visible as large green spots concentrated at multiple points in the perinuclear space. Co-localization experiments demonstrated that the fusion protein is aggregated and retained within the ER, as predicted (J. Rothman, data not shown). Upon addition of ligand, the aggregates disperse over the next 15 to 60 minutes. This disaggregation coincides with the appearance of hGH protein in the supernatant of the cells. As described for the HT88 cell line, ligand induces a several hundred fold increase in hGH (data not shown).

Figure 4:
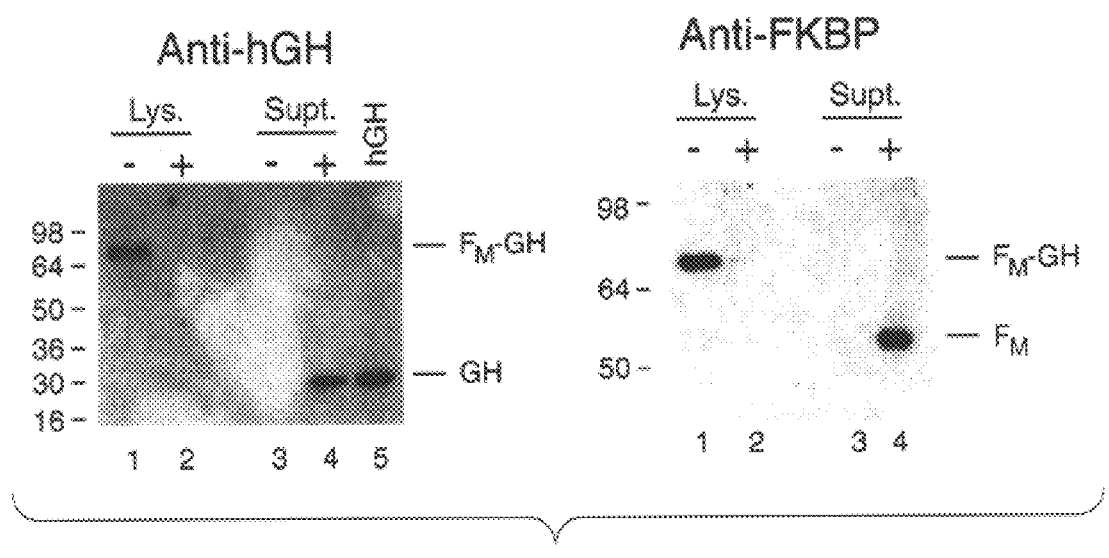
FIG. 4: Immunoblots of cell lysates and supernatants prepared from the HT88 cells incubated in the presence or absence of ligand for 2 hours. The samples were immunoblotted with anti-hGH and anti-FKBP antibodies.

To analyze further the state of the fusion protein, cell lysates and supernatants were prepared from the HT88 cells that had been incubated in the presence or absence of ligand for 2 hours. These samples were then immunoblotted with anti-hGH and anti-FKBP antibodies. As shown in FIG. 4, in the absence of ligand an approximately 75 kDa-sized band, which corresponds to the expected size of the F(36M)-hGH fusion protein, is detected in the lysate (lane 1) but not the supernatant (lane 3) of unstimulated cells with both the anti-hGH and anti-FKBP antibodies. In cells that had been stimulated with ligand for 2 hours, very little fusion protein is detected in the cell lysate, but instead, cleaved proteins are detected in the supernatant. The anti-hGH blot shows the presence of a 22 kDa sized protein (lane 6) that co-migrates with purified recombinant hGH (lane 7). The anti-FKBP blot shows the presence of a 53 kDa protein that is around the expected size of the remainder of the fusion protein (F(36M)-FCS). Together these results indicate that the F(36M)-hGH fusion protein is indeed retained within the ER in the absence of ligand, released upon interaction with ligand and subsequently cleaved at the appropriate position, resulting in the secretion of the F(36M)-FCS portion of the fusion protein and an intact hGH protein.

Example 5
Dose Response and Kinetics of hGH Secretion

Figure 5A:
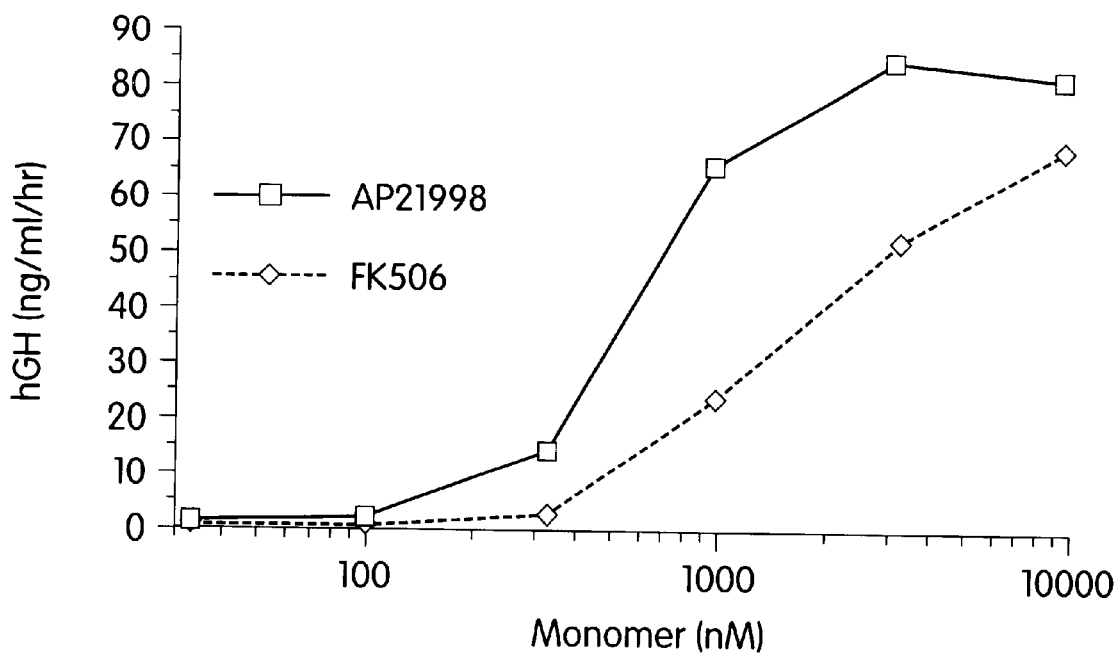
FIG. 5: Dose-dependence of hGH secretion from HT88 cells in response to ligand (FIG. 5A). Time course of accumulation of secreted hGH in the culture medium (FIG. 5B).

The amount of hGH secreted from HT88 cells in response to ligand is dose-dependent (FIG. 5A). Peak level of secretion occurs at approximately 2–3 uM AP21998 with half-maximal secretion occurring at 600 nM.

Figure 5B:
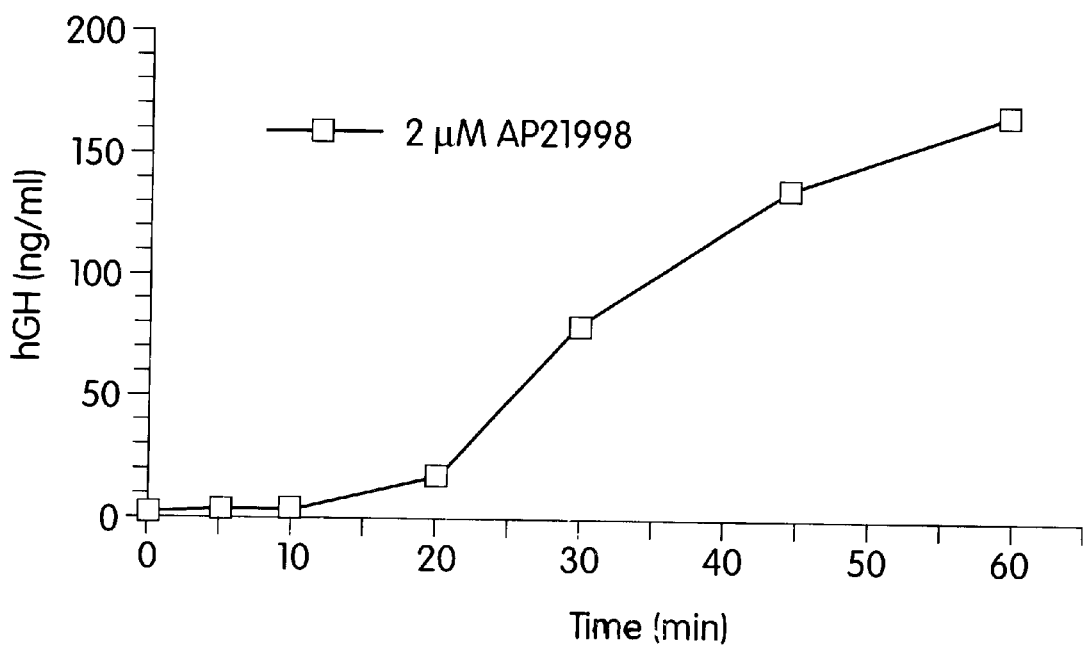

To determine the kinetics of secretion, cells were stimulated with ligand and an aliquot of medium collects at various time points to measure the accumulation of hGH in the supernatant. Following addition of saturating levels of ligand, low levels of hGH are detected in the supernatant within minutes with the peak rate of secretion occurring between 20–30 minutes (FIG. 5B). This corresponds to the amount of time it takes for a newly synthesized protein to be secreted. After the bolus release of stored fusion protein, the rate of secretion rapidly decreases.

Figure 6A:
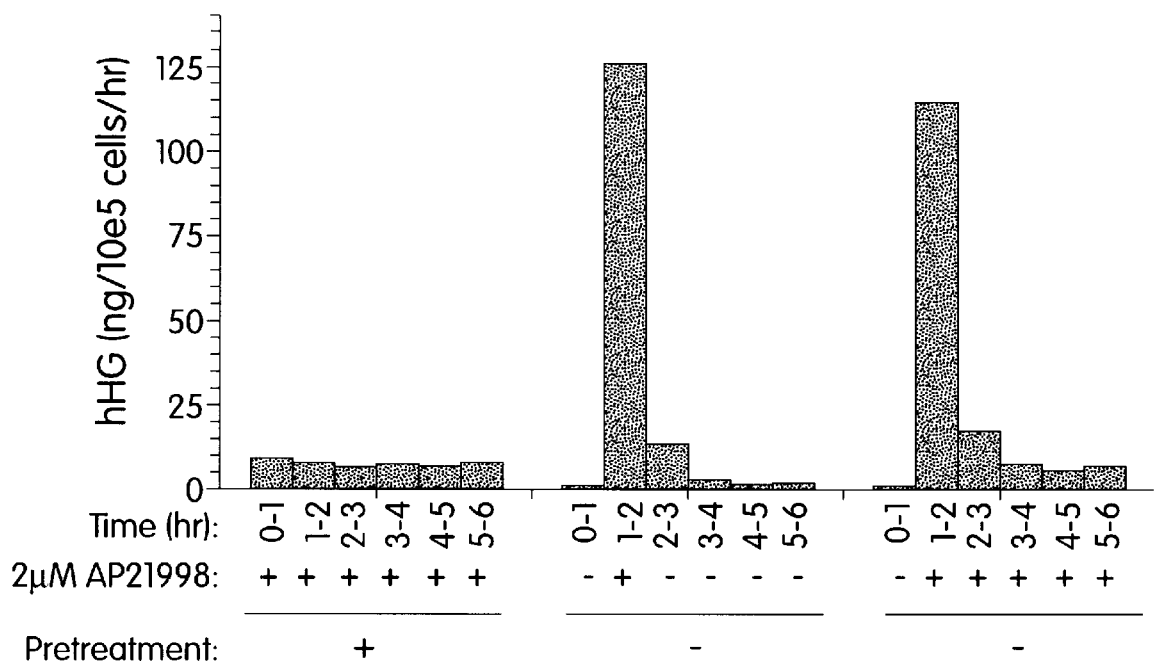
FIG. 6A Group A: the constitutive rate of secretion from the cells. Group B: secretion from cells not previously exposed to ligand. Group C: cells exposed to ligand following a large bolus release of hGH.

To further examine the kinetics of secretion in response to ligand, cells were incubated overnight in the presence or absence of ligand and then medium collected at 1 hour intervals. The cells were washed extensively between time points and the medium replaced with medium containing or lacking ligand as indicated. FIG. 6A (group A) shows the constitutive rate of secretion from the cells. In group B, a large bolus release is observed since the cells had not been exposed to ligand previously. Once ligand is washed away, however, the rate of hGH secretion quickly decreases, returning to the low basal rate within 2 hours. Group C shows that if the cells are exposed to ligand following the large bolus release, within 2 hours the rate of secretion matches that of the constitutively producing cells (group A).

Figure 6B:
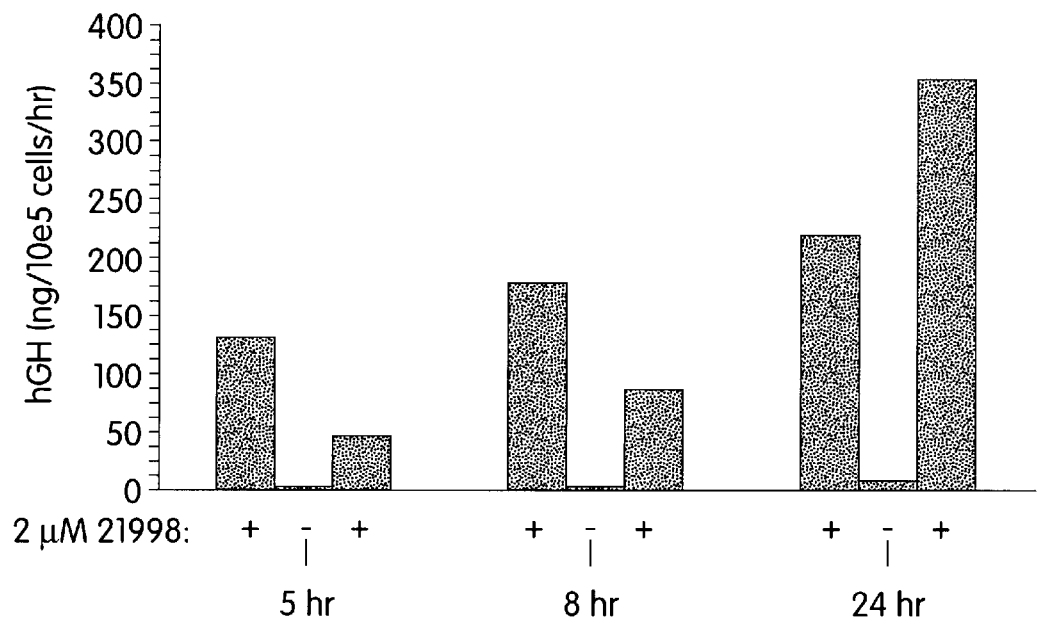
FIG. 6B shows the amount of hGH released by incubation with maximal concentration of ligand.
Figure 6C:
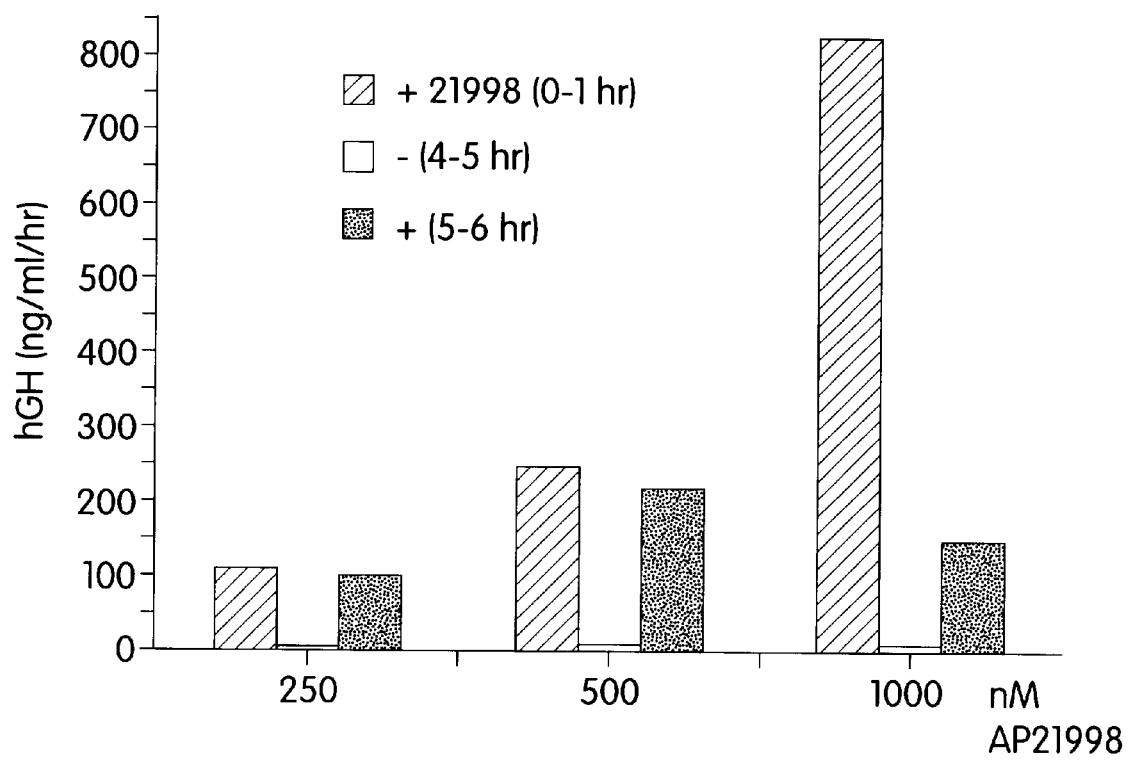
FIG. 6C shows the amount of hGH secreted following addition of sub-maximal concentrations of ligand.

Since the constitutive rate of hGH production is only about 75 ng/million cells/hr while 1250 ng/million cells is released in the first hour after the stores are emptied, it should take some time for the stores to be refilled. As shown in FIG. 6B, when the stored hGH is released by incubation with maximal concentration of ligand, it takes between 8–24 hours for the stores to be refilled so that the magnitude second bolus release matches that of the first (or exceeds it since the cell number has increased in the time). Therefore, in order to achieve consistent, rapid, pulsatile secretion the stores must not be emptied completely. As shown in FIG. 6c, if sub-maximal concentrations of ligand are added (e.g. 250 or 500 nM), an equivalent amount of hGH can be secreted 4 hours later.

Figure 7:
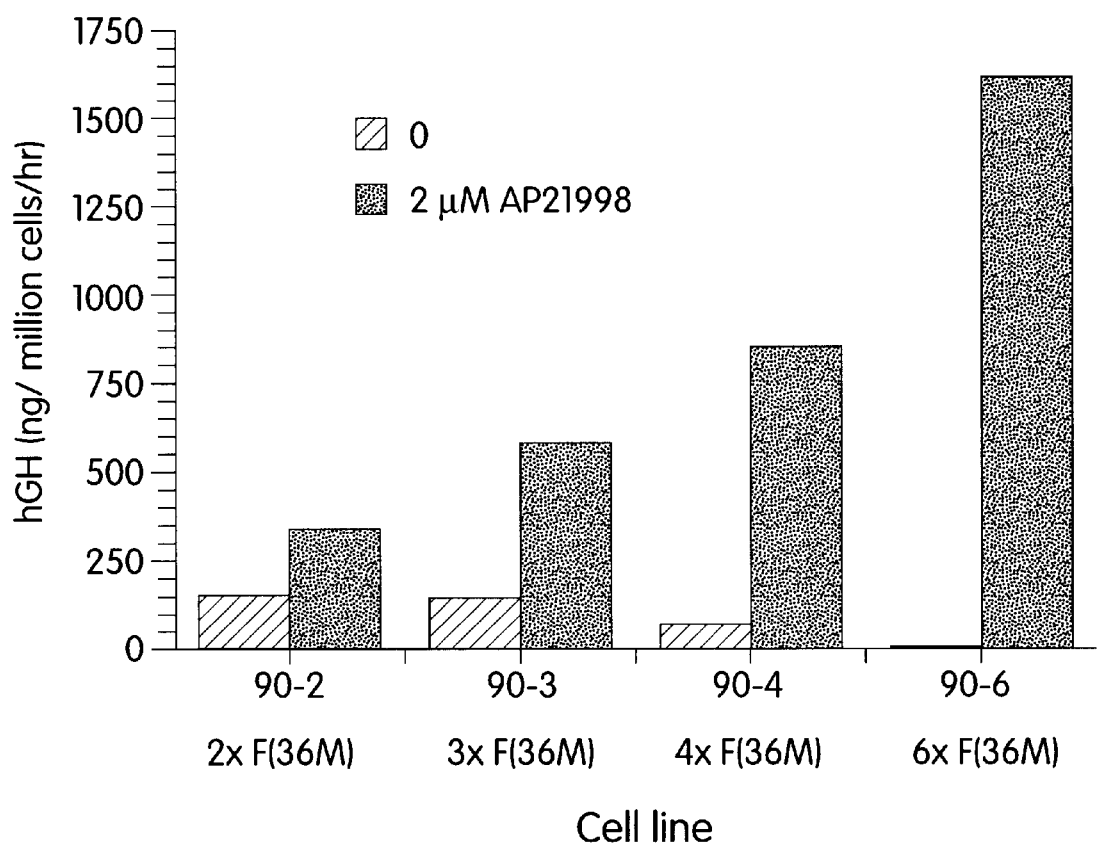
FIG. 7; Effect of varying the number of CRDs on hGH secretion. hGH secretion was measured following addition of ligand in cell lines expressing fusion proteins containing varying numbers of CRDs.

The degree of aggregation increases as the number of F(36M) domains increases. To test whether the degree of retention could be manipulated, constructs containing 2, 3 or 6 F(36M) domains were fused to hGH, stable cell lines generated and hGH secreted in the presence and absence of ligand assayed. As shown in FIG. 7, the basal secretion in the absence of ligand increases as the number of F(36M) domains decreases. This likely reflects a reduction in the size of aggregates which permits monomeric fusion proteins to escape retention. An increase in the "leakiness" of fusion protein secretion is also reflected as a decrease in the amount of stored fusion protein and, hence, the amount of protein released in bolus upon addition of ligand. It may be possible to exploit this to provide transient high level induced secretion against a back drop of relatively high constitutive basal secretion. Such a situation may be particularly desirable in the case of insulin production for the treatment of type 1 diabetes.

Example 6
Regulated Insulin Secretion

To test whether the conditional retention domain, F(36M), could also be used to enable regulated secretion of insulin, a fusion protein of the design shown in FIG. 3D was constructed. This fusion protein is analogous to the F(36M) 4-hGH fusion protein described in example X, except the mature hGH coding sequence has been replaced by coding sequence from the mature human insulin gene. Normally, in islet cells, proinsulin is processed into the mature, active, A and B chain complex by endopeptidases that are expressed exclusively in neuroendocrine cells. Therefore, to allow insulin to be processed properly in non-endocrine cells mutations were introduced at the B-C and C-A junctions that would allow processing by the ubiquitous protease furin (Groskreutz et al., J. Biol. Chem. 269:6241–6245, 1994). In addition, a third mutation, in which amino acid 10 of the B chain (histidine) was mutated to aspartic acid, was introduced to increase the stability of the protein (Groskreutz et al., J. Biol. Chem. 269:6241–6245 1994).

Figure 8:
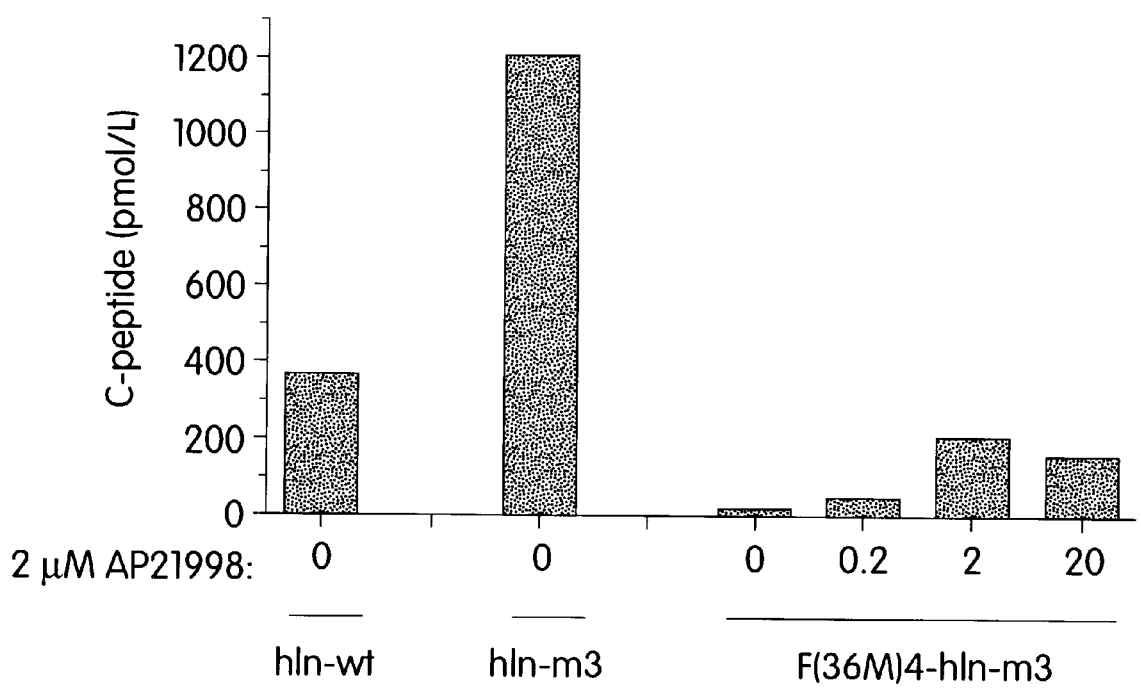
FIG. 8: Regulated secretion of insulin. Levels of insulin secretion were measured in transiently transfected HT1080 cells treated with varying concentrations of AP21998.

A vector driving expression of this F(36M)-insulin fusion protein (F(36M)4-hIn-m3) was transiently transfected into HT1080 cells. For comparison, vectors driving the expression of insulin protein alone, with (hIn-m3) or without (hIn-wt) the three mutations were also transfected. Following overnight incubation of cells in the absence of ligand, the medium was washed away and fresh medium added, without or with increasing concentrations of the monomeric ligand, AP21998. Three hours later, the amount of insulin secreted into the medium was determined by ELISA using an assay that recognizes an epitope within the C-peptide (ALPCO). As shown in FIG. 8, fusion of F(36M) domains to insulin results in a suppression of its secretion in the absence of monomeric ligand. Furthermore, secretion is induced in the presence of monomer in a dose-dependent manner.

Example 7
Regulated Expression of a Membrane Tethered Protein

Figure 9:
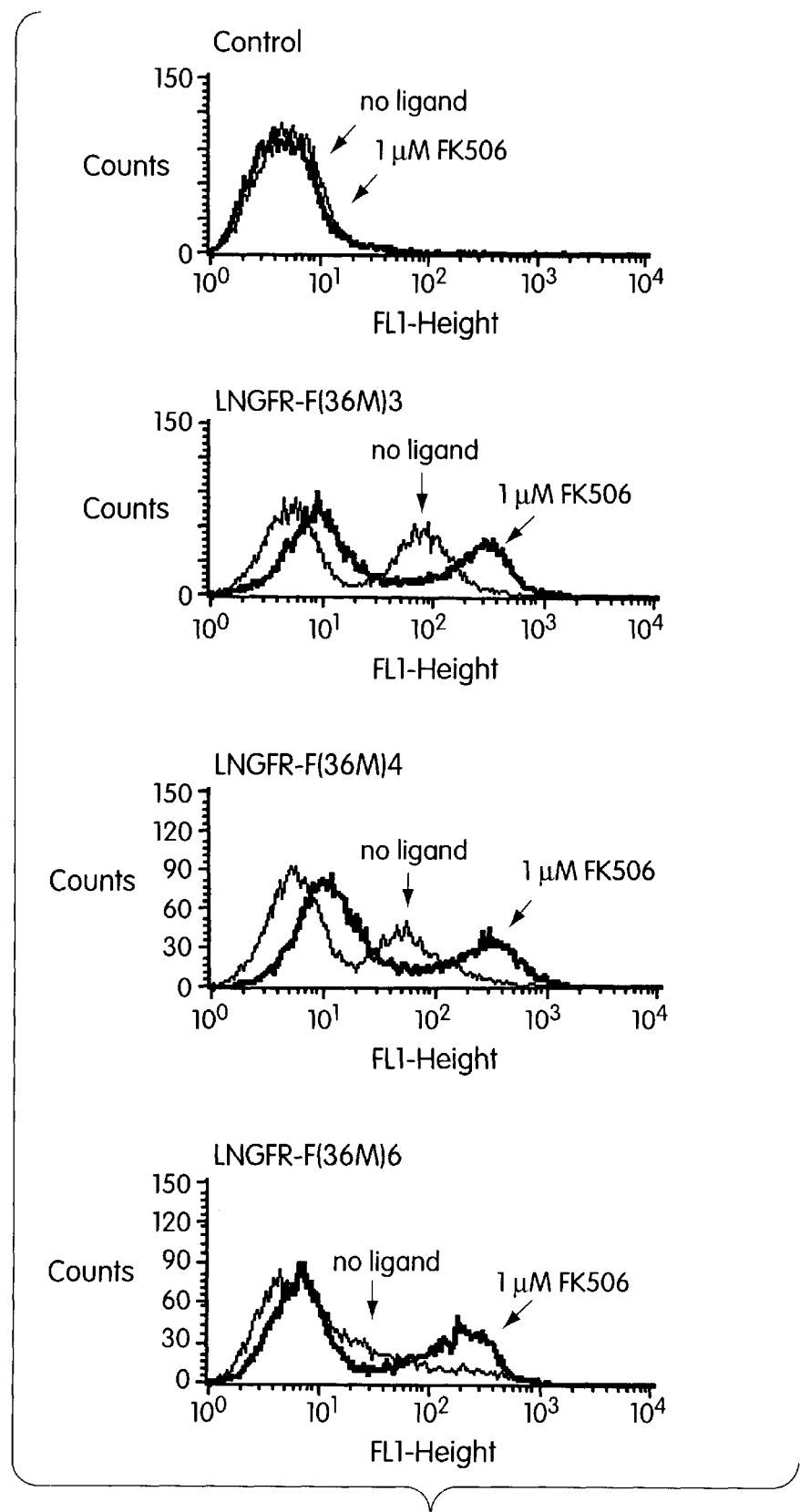
FIG. 9: Regulated expression of a membrane tethered protein. 3, 4, or 6 copies of F(36M) were fused to the extracellular and transmembrane portions of the low-affinity nerve growth factor receptor (LNGFR.

To determine whether the CRD, F(36M), could also be used to regulate surface expression of a membrane-tethered protein, 3, 4, or 6 copies of F(36M) were fused to the extracellular and transmembrane portions of the low-affinity nerve growth factor receptor (LNGFR; FIG. 3E). In these fusion proteins the F(36M) domains should be localized to the cytoplasm and tethered to the plasma membrane, in contrast to the hGH and insulin fusions described in examples 3 and 6, in which the F(36M) domains were expressed as part of a soluble protein that localized initially to the lumen of the ER. Surface expression was assessed by FACS analysis using anti-LNGFR antibodies (Chromaprobe, Mountain View, Calif.). As shown in FIG. 9, upon transfection into HT1080 cells two peaks, corresponding to low and high levels, of LNGFR surface expression are detected in the absence of monomer with each fusion protein. The relatively high level of surface expression in the absence of monomer suggests that the retention activity of the F(36M) domains is not as strong when the fusion protein is tethered to the membrane, compared to when it is in solution. This may reflect the presence of physical constraints that prevent formation of high order oligomers. However, these results show that the retention activity of the F(36M) domains clearly increases as the number of F(36M) domains increase. Furthermore, in the presence of monomeric ligand, surface expression increases significantly in all cases. Thus F(36M) domains can also be used to conditionally induce surface epxression of a membrane-tethered protein.

Example 8
Construction and Testing of a Construct for Conditional Secretion of hGH Using Rat Retinol Binding Protein as a CRD Rat retinol binding protein (rRBP) is conditionally retained in the ER of a variety of cell types unless retinol is added (Melhus et al., J Biol Chem 1992 vol 26712036–12041), and so is a suitable candidate for use as a CRD. We assembled a construct to test whether rRBP could be used to obtain conditional secretion of the target protein human growth hormone (hGH) in response to retinoid ligands. The general structure of the construct is shown below:

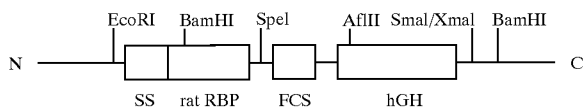

The construct comprises the rRBP cDNA, including the authentic signal sequence (SS), followed by sequence encoding the furin cleavage site (FCS) derived from stromelysin E (the amino acid sequence SARNRQKR), SEQ ID NO. 1), and then the mature 191 amino acid cDNA coding sequence of hGH (lacking the signal sequence) followed by an in-frame stop codon. The stromelysin E cleavage site was chosen because it is of human origin (and therefore expected to be minimally immunogenic in future human therapeutic applications), and because it is known to be recognised by furin in the context of fusion to proteins where the P1' residue—the residue following the cleavage site—is Phe, as in hGH (for a review see Denault and Leduc, FEBS Lett 1996 vol 379, 113–116). All junctions between the various sequence motifs and domains are direct and include no additional sequence, with the exception of an additional threonine codon between rRBP and FCS to accommodate the SpeI site. The expression cassette was cloned into the expression vector pC$_4$EN, placing expression under the control of the strong hCMV immediate early promoter and enhancer.

A DNA fragment encompassing the rRBP cDNA was obtained by RT-PCR from rat liver poly A+ RNA (obtained from Clontech, catalog # 6710-1) using the Clontech first strand kit with random primers, followed by PCR under conventional amplification conditions using primers RBP-5' (263) and RBP-3' (264). The PCR product was purified and digested with EcoRI and SpeI. A second DNA fragment encoding the FCS and mature hGH coding sequence was obtained by PCR amplification from the hGH cDNA expression vector Z12IHB. The PCR primers used were FCS-hGH-5' (265) and hGH-3' (266); primer FCS-hGH-5' (265) includes additional sequence that encodes the FCS. The PCR product was purified and digested with SpeI and BamHI. The two DNA fragments were then cloned into EcoRI-BamHI-opened pC$_4$EN in a three-way ligation to produce the final expression vector pC$_4$EN-rRBP-hGH. Positive clones were completely sequenced to check that no errors were incorporated during cloning.

The construct contains restriction sites that can be used to add additional modules to the expressed fusion protein. Thus the stromelysin E FCS can be replaced with alternative cleavage sites by excising the existing SpeI-AflII fragment and cloning in an appropriate SpeI-AflII compatible oligonucleotide pair. An epitope tag can be appended to the rRBP, upstream of the FCS, to allow immunochemical tracking of the rRBP module inside cells. Alternative target proteins can be cloned as SpeI-XmaI fragments (the use of the 3' BamHI site is precluded by the existence of another BamHI site in the rRBP coding sequence). Alternative CRDs can be cloned in place of rRBP as EcoRI-SpeI fragments.

Particularly important additional constructs are those that incorporate multiple reiterated copies of rRBP. These are obtained by reamplifying pC$_4$EN-rRBP-hGH using primers 5'-RBP-Xba and 3'-RBP-Spe, generating a fragment containing the mature rRBP sequence (no signal sequence) flanked by SpeI-compatible 5' XbaI and 3' SpeI sites. The PCR product is purified, digested with XbaI and SpeI, and cloned into SpeI-opened pC$_4$EN-rRBP-hGH to generate pC$_4$EN-(rRBPx2)-hGH. An analogous procedure can be used to prepare constructs encoding higher order concatenates of rRBP.

PCR Primers
RBP-5' (263) 5'CGTACgaattcCAGAAGCGCGTATG-GAGTGGGTGTGGGCGCTCGTGCTG (SEQ ID NO. 23)
RBP-3' (264) 5'GCATGactagtCAAACTGTTTCT-TGAGGGTCTGCTTTGACAG (SEQ ID NO. 24)
FCS-hGH-5' (265) (SEQ ID NO. 25)
5'GCAACactagtGCTAGAAACCGTCAGAA-GAGATTCCCAACCATTCCCTTAAGCAG-GCCTTTTGACAACGC (SEQ ID NO. 26)
hGH-3' (266) 5'GCTCAggatccCGGGCTAGAAGCCA-CAGCTGCCCTCCACAGAGCG (SEQ ID NO. 27)
5'-RBP-Xba 5'TCAGCtctagaGAGCGCGACTGCAGGGT-GAGC (SEQ ID NO. 28)
3'-RBP-Spe 5'GAAGCactagtCAAACTGTTTCT-TGAGGGTCTG (SEQ ID NO. 29)

The sequence of the expression cassette is as follows (key restriction sites underlined):

```
    EcoRI              rRBP signal sequence-->
   1 gaattccagaagcgcgt ATG GAG TGG GTG TGG GCG CTC GTG CTG CTG GCG GCT CTG GGA GGC    62
   1                    M   E   W   V   W   A   L   V   L   L   A   A   L   G   G    15 rRBP mature protein sequence-->
  63 GGC AGC GCC GAG CGC GAC TGC AGG GTG AGC AGC TTC AGA GTC AAG GAG AAC TTC GAC AAG  122
  16  G   S   A   E   R   D   C   R   V   S   S   F   R   V   K   E   N   F   D   K   35

BamHI
 123 GCT CGT TTC TCT GGG CTC TGG TAT GCC ATC GCC AAA AAG GAT CCC GAG GGT CTC TTT TTG  182
  36  A   R   F   S   G   L   W   Y   A   I   A   K   K   D   P   E   G   L   F   L   55

183 CAA GAC AAC ATC ATC GCT GAG TTT TCT GTC GAC GAG AAG GGT CAT ATG AGC GCT ACA GGC  242
  56  Q   D   N   I   I   A   E   F   S   V   D   E   K   G   H   M   S   A   T   A   75

243 AAG GGA CGA GTC CGT CTT CTG AGC AAC TGG GAA GTG TGT GCA GAC ATG GTG GGC ACT TTC  302
  76  K   G   R   V   R   L   L   S   N   W   E   V   C   A   D   M   V   G   T   F   95

303 ACA GAT ACA GAA GAT CCT GCC AAG TTC AAG ATG AAG TAC TGG GGT GTA GCC TCC TTT CTC  362
  96  T   D   T   E   D   P   A   K   F   K   M   K   Y   W   G   V   A   S   F   L  115

363 CAG CGA GGA AAC GAT GAC CAC TGG ATC ATC GAT ACG GAC TAC GAC ACC TTC GCT CTG CAG  422
 116  Q   R   G   N   D   D   H   W   I   I   D   T   D   Y   D   T   F   A   L   Q  135

423 TAT TCC TGC CGC CTG CAG AAT CTG GAT GGC ACC TGT GCA GAC AGC TAC TCC TTT GTG TTT  482
 136  Y   S   C   R   L   Q   N   L   D   G   T   C   A   D   S   Y   S   F   V   F  155

483 TCT CGT GAC CCC AAT GGC CTG ACC CCG GAG ACA CGG AGG CTG GTG AGG CAG CGA CAG GAG  542
 156  S   R   D   P   N   G   L   T   P   E   T   R   R   L   V   R   Q   R   Q   E  175

543 GAG CTG TGC CTA GAG AGG CAG TAC AGA TGG ATC GAG CAC AAT GGT TAC TGT CAA AGC AGA  602
 176  E   L   C   L   E   R   Q   Y   R   W   I   E   H   N   G   Y   C   Q   S   R  195

SpeI  FCS-->                                  mature hGH-->
 603 CCC TCA AGA AAC AGT TTG ACT AGT GCT AGA AAC CGT CAG AAG AGA TTC CCA ACC ATT CCC  662
 196  P   S   R   N   S   L   T   S   A   R   N   R   Q   K   R   F   P   T   I   P  215

AflII
 663 TTA AGC AGG CCT TTT GAC AAC GCT ATG CTC CGC GCC CAT CGT CTG CAC CAG CTG GCC TTT  722
 216  L   S   R   P   F   D   N   A   M   L   R   A   H   R   L   H   Q   L   A   F  235

723 GAC ACC TAC CAG GAG TTT GAA GAA GCC TAT ATC CCA AAG GAA CAG AAG TAT TCA TTC CTG  782
 236  D   T   Y   Q   E   F   E   E   A   Y   I   P   K   E   Q   K   Y   S   F   L  255

783 CAG AAC CCC CAG ACC TCC CTC TGT TTC TCA GAG TCT ATT CCG ACA CCC TCC AAC AGG GAG  842
 256  Q   N   P   Q   T   S   L   C   F   S   E   S   I   P   T   P   S   N   R   E  275

843 GAA ACA CAA CAG AAA TCC AAC CTA GAG CTG CTC CGC ATC TCC CTG CTG CTC ATC CAG TCG  902
 276  E   T   Q   Q   K   S   N   L   E   L   L   R   I   S   L   L   L   I   Q   S  295

903 TGG CTG GAG CCC GTG CAG TTC CTC AGG AGT GTC TTC GCC AAC AGC CTG GTG TAC GGC GCC  962
 296  W   L   E   P   V   Q   F   L   R   S   V   F   A   N   S   L   V   Y   G   A  315

963 TCT GAC AGC AAC GTC TAT GAC CTC CTA AAG GAC CTA GAG GAA GGC ATC CAA ACG CTG ATG 1022
 316  S   D   S   N   V   Y   D   L   L   K   D   L   E   E   G   I   Q   T   L   M  335

1023 GGG AGG CTG GAA GAT GGC AGC CCC CGG ACT GGG CAG ATC TTC AAG CAG ACC TAC AGC AAG 1082
 336  G   R   L   E   D   G   S   P   R   T   G   Q   I   F   K   Q   T   Y   S   K  355

1083 TTC GAC ACA AAC TCA CAC AAC GAT GAC GCA CTA CTC AAG AAC TAC GGG CTG CTC TAC TGC 1142
 356  F   D   T   N   S   H   N   D   D   A   L   L   K   N   Y   G   L   L   Y   C  375

1143 TTC AGG AAG GAC ATG GAC AAG GTC GAG ACA TTC CTG CGC ATC GTG CAG TGC CGC TCT GTG 1202
 376  F   R   K   D   M   D   K   V   E   T   F   L   R   I   V   Q   C   R   S   V  395

1203 GAG GGC AGC TGT GGC TTC TAG cccgggatcctgagaacttcagggtgagtttggggacccttgattgttcttt 1275
                                                                    (SEQ ID NO. 30)

396  E   G   S   C   G   F   *       BamHI                                       402
         (SEQ ID NO. 31)
```

The sequence of the encoded protein is as follows:
MEWVWHALVLLAALGGGSAERDCRVSS-
FRVKENFDKARFSGLWYAIAKKD-
PEGLFLQDNIIAEFSVDEKGHM-
SATAKGRVRLLSNWEVCADMVGTFTDTEDPAKF
KMKYWGVASFLQRGNDDHWIIDTDYDT-
FALQYSCRLQNLDGTCADSYSFVFSRDP-
NGLTPETRRLVRQRQEELCLERQYRWIE-
HNGYCQSRPSRNSLTSARNRQKRFPTIPLSRPFDN
AMLRAHRLHQLAFDTYQEFEEAYIP-
KEQKYSFLQNPQTSLCFSESIPTPSN-
REETQQKSNLELLRISLLLIQSWLEPVQ-
FLRSVFANSLVYGASDSNVYDLLKDLEEGIQTLM
GRLEDGSPRTGQIFKQTYSKFDTNSHND-
DALLKNYGLLYCFRKDMDKVEDFL-
RIVQCRSVEGSCGF (SEQ ID NO. 31)

The nucleotide sequence of the expression cassette is as follows:
ATGGAGDGGGTGTGGGCGCTCGTGCTGCTGGCGGCTCTGGGAGGCGGCAGCGCCGAGCGCGACTGCAGGGTGAGCAGCTTCAGAGTCAAGGAGAACTTCGACAAGGCTCGTTTCTCTGGGCTCTGGTATGCCATCGCCAAAAAGGATCCCGAGGGTCTCTTTTGCAAGACAACATCATCGCTGAGTTTCTGTCGACGAGAAGGGTCATATGAGCGCTACAGCCAAGGGACGAGTCCGTCTTCTGAGCAACTGGGAAGTGTGTGCAGACATGGTGGGCACTTTCACAGATACAGAAGATCCTGCCAAGTTCAAGATGAAGTACTGGGGTGTAGCCTCCTTTCTCCAGCGAGGAAACGATGACCACTGGATCATCGATACGGACTACGACACCTTCGCTCTGCAGTATTCCTGCCGCCTGCAGAATCTGGATGGCACCTGTGCAGACAGCTACDCCTTTGTGTTTTCTCGTGACCCCAATGGCCTGACCCCGGAGACACGGAGGCTGGTGAGGCAGCGACAGGAGGAGCTGTGCCTAGAGAGGCAGTACAGATGGATCGAGCACAATGGTTACTGTCAAAGCAGACCCTCAAGAAACAGTTTGACTAGTGCTAGAAACCGTCAGAAGAGATTCCCAACCATTCCCTTAAGCAGGCCTTTTGACAACGCTATGCTCCGCGCCCATCGTCTGCACCAGCTGGCCTTTGACACCTACCAGGATTTGAAGAAGCCTATATCCCAAAGGAACAGAAGTATTCATTCCTGCAGAACCCCCAGACCTCCCTCTGTTTCTCAGAGTCTATTCCGACACCCTCCAACAGGGAGGAAACACAACAGAAATCCAACCTAGAGCTGCTCCGCATCTCCCTGCTGCTCATCCAGTCGTGGCTGGAGCCCGTGCAGTTCCTCAGGAGTGTCTTCGCCAACAGCCTGGTGTACGGCGCCTCTGACAGCAACGTCTATGACCTCCTAAAGGACCTAGAGGAAGGCATCCAAACGCTGATGGGGAGGCTGGAAGATGGCAGCCCCCGGACTGGGCAGATCTTCAAGCAGACCTACAGCAAGTTCGACACAAACTCACACAACGATGACGCACTACTCAAGAACTACGGGCTGCTCTACTGCTTCAGGAAGGACATGGACAAGGTCGAGACATTCCTGCGCATCGTGCAGTGCCGCTCTGTGGAGGGCAGCTGTGGCTTCTAG (SEQ ID NO. 32)

To test whether fusion to rRBP can result in ligand-dependent prevention of secretion of hGH, pC₄EN-rRBP-hGH, pC₄EN-(rRBPx2)-hGH and their derivatives are transiently transfected into the human fibrosarcoma cell line HT1080 using standard methods (eg see Rivera et al., Nature Med 2: 1028–1032 1996; Amara et al., PNAS 94:10618–10623 1997). After overnight incubation, medium is removed and new medium added, containing either no drug or retinol at various concentrations. After a further incubation of 2–24 hours, the amount of hGH secreted into the medium is determined by radioimmunoassay (Rivera et al., Nature Med 2: 1028–1032 1996).

A critical feature for these experiments, as described by Melhus et al. (J Biol Chem 1992 vol 26712036–12041), is the use of delipidized serum in the culture medium, since untreated serum contains significant amounts of retinoids that might lead to secretion of rRBP in the absence of exogenously added retinol. Methods for preparing delipidized serum are known (Rothblat et al., In Vitro 1976 vol 12, 554–557).

Increased secretion of hGH upon addition of increasing concentrations of retinol would indicate that rRBP is acting as a CRD to retain hGH in secretory compartments until addition of retinol. Experiments to identify the best configuration of the system include engineering multimers of rRBP to attempt to enhance the retention effect, and testing of a variety of different retinol analogs for activity. Further experiments to confirm the subcellular location of rRBP fusions include immunocytochemical subcellular localization of components of the constructs before and after addition of retinoids using, for example, anti-hGH or anti-rRBP antibodies.

Example 9

Physiological Effects of Regulated Insulin Secretion in vivo

Figure 11A:
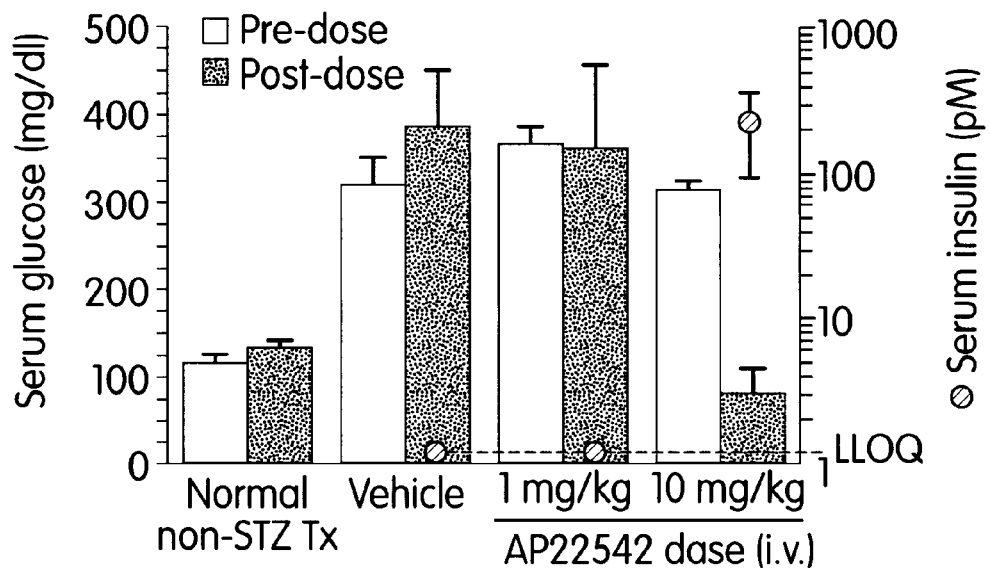
FIG. 11: Ligand-mediated regulation of insulin and glucose levels in vivo. (A) Insulin and glucose levels were measured in mice implanted with FKBP(F36M)-insulin-containing constructs before and after administration of AP22542. (B) Levels of serum glucose were measured in mice implanted with FKBP(F36M)-insulin-containing constructs at various time points following administration of AP22542.

To test whether this system could be used to regulate secretion of insulin in vivo and effect changes in serum glucose levels, 2×10e7 HT101-10p cells were implanted intramuscularly into male nu/nu mice. HT101-10p cells were generated by stably transfecting HT1080 cells with a vector that drives expression of the F(36M)4-hIn-m3 fusion protein. Mice were made hyperglycemic by treatment 2 days earlier with 300 mg/kg streptozotocin (STZ). As shown in FIG. 11a, STZ treatment elevates serum glucose levels to ~350 mg/dl from ~100 mg/dl seen in non-STZ treated mice. Approximately 1 hr after cells are implanted, animal received vehicle or the indicated dose of intravenous AP22542 (an analog of AP21998). Two hours later, serum samples were collected and assayed for insulin (Ultrasensitive human insulin-specific RIA, Linco) and glucose (Sigma) concentrations. As shown in FIG. 11a, treatment of hyperglycemic mice with vehicle or a low dose of AP22542 (1 mg/kg) fails to increase serum insulin levels above the lower limit of detection and there is no change in serum glucose. In contrast, in animals treated with 10 mg/kg AP22542, serum insulin levels increase to ~200 pM and serum glucose levels decline to ~75 mg/dl.

Figure 11B:
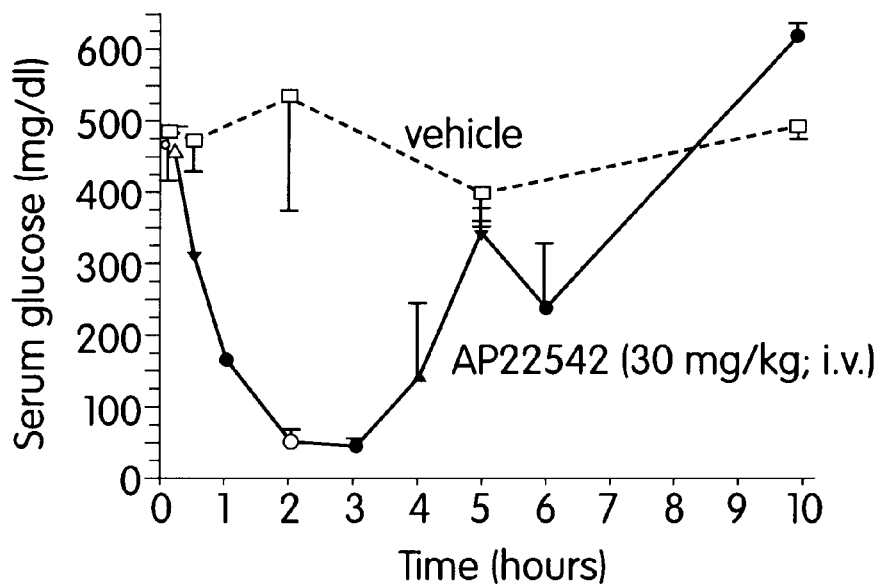

To examine the kinetics of this ligand-induced reduction in serum glucose, STZ-treated mice implanted with 2×10e7 HT101-10p cells were administered a single dose of 30 mg/kg AP22542 intravenously. Serum glucose levels were measured at various times between 5 minutes and 10 hours later. As shown in FIG. 11b, at 5 and 15 minutes after administration of AP22542, serum glucose levels are indistinguishable from animals treated with vehicle. However, within 30 minutes there is a significant reduction in serum glucose and by two hours serum glucose levels have declined to 50 mg/dl from initial levels of nearly 500 mg/dl. This effect is transient as serum glucose levels rise to 350 mg/dl within 5 hours and return to baseline between 6 and 10 hours later. Since insulin secretion is dependent on the presence of the drug, administration of lower doses of AP22542 or of a ligand with a shorter half life should result in an even more transient production of secreted protein and resulting physiological effect. Conversely, administration of higher doses of AP22542 or of a ligand with a longer half life should result in a more prolonged production of secreted protein.

What is claimed is:

1. A method for inducing cells to secrete a protein of interest, the method comprising treating a cell containing a fusion protein comprising at least one conditional retention domain ("CRD") and at least one additional domain that is heterologous thereto with a ligand which binds to the CRD, the treating being at a concentration of ligand sufficient to induce secretion of the fusion protein or a portion thereof.

2. A method of claim 1 wherein the fusion protein contains more than one CRD.

3. A method of claim 1 wherein the fusion protein molecules form aggregates with one another in the absence of a ligand which binds to the CRD.

4. A method of claim 1 wherein the CRD is derived from retinol binding protein, FKBP (FK506-binding protein) IgM or alpha1-antitrypsin.

5. A method of claim 1 wherein the CRD comprises an FKBP domain with an amino acid replacement at F36 or W59.

6. A method of claim 5 wherein the CRD comprises an FKBP domain containing the mutation F36M or W59V.

7. A method of claim 1 wherein the heterologous domain of the fusion protein comprises the polypeptide sequence of a protein of interest.

8. A method of claim 7 wherein the protein of interest is a hormone, an endorphin, an antibody or an immunogen.

9. A method of claim 8 wherein the protein of interest is selected from the group consisting of insulin, parathyroid hormone and beta-endorphin.

10. A method of claim 1 wherein the fusion protein comprises an enzymatic cleavage site.

11. A method of claim 10 wherein the cleavage site is a furin cleavage site.

12. A method of claim 11 wherein the furin cleavage site comprises the amino acid sequence SARNRQKR (SEQ ID NO. 1).

13. A method of claim 1 wherein the fusion protein further comprises a secretory signal sequence.

14. A method of claim 13 wherein the secretory signal sequence is the signal sequence from the human growth hormone gene.

15. A method of claim 1 wherein the fusion protein comprises a secretory signal sequence, at least one conditional retention domain, a furin cleavage site, and a polypeptide sequence of interest.

16. A method of claim 15 wherein the fusion protein comprises a secretory signal sequence from human growth hormone, three F36M FKBP domains, a human stromelysin-3 furin cleavage site, and a polypeptide sequence of interest.

17. A method of claim 1 wherein the fusion protein comprises a lysosomal targeting signal.

18. A method of claim 1 wherein the cells are mammalian cells.

19. A method of claim 1 wherein the cells are of human origin.

20. A method of claim 1 wherein the cells are primary cells.

21. A method of claim 1 wherein the cells are in an animal.

* * * * *

SEQUENCE LISTING

<160> NUMBER OF SEQ ID NOS: 38

<210> SEQ ID NO 1
<211> LENGTH: 7
<212> TYPE: PRT
<213> ORGANISM: Homo sapiens

<400> SEQUENCE: 1

Met Ser Met Arg Val Arg Arg
 1               5

<210> SEQ ID NO 2
<211> LENGTH: 7
<212> TYPE: PRT
<213> ORGANISM: Homo sapiens

<400> SEQUENCE: 2

Lys Pro Ala Lys Ser Ala Arg
 1               5

<210> SEQ ID NO 3
<211> LENGTH: 6
<212> TYPE: PRT
<213> ORGANISM: Homo sapiens

<400> SEQUENCE: 3

Lys Ser Val Lys Lys Arg
 1               5

<210> SEQ ID NO 4
<211> LENGTH: 7
<212> TYPE: PRT
<213> ORGANISM: Homo sapiens

<400> SEQUENCE: 4

Ala Arg Asn Arg Gln Lys Arg
 1               5

<210> SEQ ID NO 5
<211> LENGTH: 7
<212> TYPE: PRT
<213> ORGANISM: Homo sapiens

<400> SEQUENCE: 5

Arg Pro Ser Arg Lys Arg Arg
 1               5

<210> SEQ ID NO 6
<211> LENGTH: 7
<212> TYPE: PRT
<213> ORGANISM: Homo sapiens

<400> SEQUENCE: 6

Thr Glu Lys Arg Lys Lys Arg
 1               5

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:PCR primer

<400> SEQUENCE: 7
tcccgcacct cttcggccag cgaattccag aagcgcgtat                                        40

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 8
gactcactat aggacgcgtt cgagctcgcc cc                                                32

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 9
catcattttg gcaaaggatt cactcctcag g                                                 31

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 10
gatggaaaga aatggattc ctcccgg                                                       27

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 11
tctagagtga gcaagggcga ggag                                                         24

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence:PCR primer

<400> SEQUENCE: 12
ggatccttat taactagtct tgtacagctc gtccatg                                           37

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 13
aagcttacca ctcagggtcc tgtgg                                                        25

<210> SEQ ID NO 14
<211> LENGTH: 19
<212> TYPE: DNA

<210> SEQ ID NO 14
<211> LENGTH: 19 (shown at right as 19)
<213> ORGANISM: Artificial Sequence
<220> FEATURE:
<223> OTHER INFORMATION: Description of Artificial Sequence:PCR primer

<400> SEQUENCE: 14
gaattcgtgg caacttcca                                          19

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:PCR primer

<400> SEQUENCE: 15
cacaggaccc tgaattctaa gcttgtggc                               29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 16
ataagggaat ggttctagag gcactgccct                              30

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 17
atgccacccg ggactagtga agccacagct g                            31

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence:PCR primer

<400> SEQUENCE: 18
actagtgcta gaaaccgtca gaagagattc ccaaccattc ccttaagc          48

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 19
ggatcccggg ctagaagcca cagctgccct c                            31

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 20
cgaattcttc tgccatggcc ctgtggatgc gc                           32

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 21
cggatccgca ggctgcgtct agttgcagta g                          31

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence:PCR primer

<400> SEQUENCE: 22
cactagtgct agaaaccgtc agaagagatt tgtgaaccaa cacctgtgcg gc    52

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 23
cggatccgca ggctgcgtct agttgcagta g                          31

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 24
cctgtgcggc tcagacctgg tggaagc                               27

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence:PCR primer

<400> SEQUENCE: 25
cttctacaca cccaggacca agcgggaggc agagg                      35

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:PCR primer

<400> SEQUENCE: 26
ccctggaggg gtcccggcag aagcgtggc                             29

<210> SEQ ID NO 27
<211> LENGTH: 341
<212> TYPE: DNA
<213> ORGANISM: Homo sapiens -continued

```
<400> SEQUENCE: 27
ctgggggcct tgcttggcaa cagcacagac ccagctgtgt tcacagacct ggcatccgtc      60
gacaactccg agtttcagca gctgctgaac cagggcatac ctgtggcccc ccacacaact     120
gagcccatgc tgatggagta ccctgaggct ataactcgcc tagtgacagg ggcccagagg     180
ccccccgacc cagctcctgc tccactgggg gccccggggc tccccaatgg cctcctttca     240
ggagatgaag acttctcctc cattgcggac atggacttct cagccctgct gagtcagatc     300
agctcctaag ggggtgacgc ctgccctccc cagagcactg g                         341

<210> SEQ ID NO 28
<211> LENGTH: 8
<212> TYPE: PRT
<213> ORGANISM: Homo sapiens

<400> SEQUENCE: 28

Ser Ala Arg Asn Arg Gln Lys Arg
  1               5

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence:PCR primer

<400> SEQUENCE: 29
cgtacgaatt ccagaagcgc gtatggagtg ggtgtgggcg ctcgtgctg                  49

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence:PCR primer

<400> SEQUENCE: 30
gcatgactag tcaaactgtt tcttgagggt ctgctttgac ag                        42

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence:PCR primer

<400> SEQUENCE: 31
gcaacactag tgctagaaac cgtcagaaga gattcccaac cattcccttta agcaggcctt     60 ttgacaacgc                                                            70

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence:PCR primer

<400> SEQUENCE: 32
gctcaggatc ccgggctaga agccacagct gccctccaca gagcg                     45

<210> SEQ ID NO 33
<211> LENGTH: 32
<212> TYPE: DNA
```

<213> ORGANISM: Artificial Sequence
<220> FEATURE:
<223> OTHER INFORMATION: Description of Artificial Sequence:PCR primer

<400> SEQUENCE: 33
tcagctctag agagcgcgac tgcagggtga gc    32

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence:PCR primer

<400> SEQUENCE: 34
gaagcactag tcaaactgtt tcttgagggt ctg    33

<210> SEQ ID NO 35
<211> LENGTH: 1275
<212> TYPE: DNA
<213> ORGANISM: Homo sapiens

<400> SEQUENCE: 35

```
gaattccaga agcgcgtatg gagtgggtgt gggcgctcgt gctgctggcg gctctgggag      60
gcggcagcgc cgagcgcgac tgcagggtga gcagcttcag agtcaaggag aacttcgaca     120
aggctcgttt ctctgggctc tggtatgcca tcgccaaaaa ggatcccgag ggtctctttt     180
tgcaagacaa catcatcgct gagttttctg tcgacgagaa gggtcatatg agcgctacag     240
ccaagggacg agtccgtctt ctgagcaact gggaagtgtg tgcagacatg gtgggcactt     300
tcacagatac agaagatcct gccaagttca agatgaagta ctggggtgta gcctcctttc     360
tccagcgagg aaacgatgac cactggatca tcgatacgga ctacgacacc ttcgctctgc     420
agtattcctg ccgcctgcag aatctggatg cacctgtgc agacagctac tcctttgtgt     480
tttctcgtga ccccaatggc ctgaccccgg agacacggag gctggtgagg cagcgacagg     540
aggagctgtg cctagagagg cagtacagat ggatcgagca caatggttac tgtcaaagca     600
gaccctcaag aaacagtttg actagtgcta gaaaccgtca aagagattc ccaaccattc     660
ccttaagcag gcctttgac aacgctatgc tccgcgccca tcgtctgcac cagctggcct     720
ttgacaccta ccaggagttt aagaagcct atatcccaaa ggaacagaag tattcattcc     780
tgcagaaccc ccagacctcc ctctgttct cagagtctat tccgacaccc tccaacaggg     840
aggaaacaca acagaaatcc aacctagagc tgctccgcat ctccctgctg ctcatccagt     900
cgtggctgga gcccgtgcag ttcctcagga gtgtcttcgc caacagcctg gtgtacggcg     960
cctctgacag caacgtctat gacctcctaa aggacctaga ggaaggcatc caaacgctga    1020
tgggaggct ggaagatggc agcccccgga ctgggcagat cttcaagcag acctacagca    1080
agttcgacac aaactcacac aacgatgacg cactactcaa gaactacggg ctgctctact    1140
gcttcaggaa ggacatggac aaggtcgaga cattcctgcg catcgtgcag tgccgctctg    1200
tggagggcag ctgtggcttc tagcccggga tcctgagaac tcagggtga gtttgggac     1260
ccttgattgt tcttt                                                    1275
```

<210> SEQ ID NO 36
<211> LENGTH: 401
<212> TYPE: PRT
<213> ORGANISM: Homo sapiens

<400> SEQUENCE: 36

-continued

```
Met Glu Trp Val Trp Ala Leu Val Leu Leu Ala Ala Leu Gly Gly Gly
 1               5                  10                  15

Ser Ala Glu Arg Asp Cys Arg Val Ser Ser Phe Arg Val Lys Glu Asn
            20                  25                  30

Phe Asp Lys Ala Arg Phe Ser Gly Leu Trp Tyr Ala Ile Ala Lys Lys
        35                  40                  45

Asp Pro Glu Gly Leu Phe Leu Gln Asp Asn Ile Ile Ala Glu Phe Ser
    50                  55                  60

Val Asp Glu Lys Gly His Met Ser Ala Thr Ala Lys Gly Arg Val Arg
 65                  70                  75                  80

Leu Leu Ser Asn Trp Glu Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Arg Gly Asn Asp Asp His Trp Ile Ile Asp Thr Asp
        115                 120                 125

Tyr Asp Thr Phe Ala Leu Gln Tyr Ser Cys Arg Leu Gln Asn Leu Asp
    130                 135                 140

Gly Thr Cys Ala Asp Ser Tyr Ser Phe Val Phe Ser Arg Asp Pro Asn
145                 150                 155                 160

Gly Leu Thr Pro Glu Thr Arg Arg Leu Val Arg Gln Arg Gln Glu Glu
                165                 170                 175

Leu Cys Leu Glu Arg Gln Tyr Arg Trp Ile Glu His Asn Gly Tyr Cys
            180                 185                 190

Gln Ser Arg Pro Ser Arg Asn Ser Leu Thr Ser Ala Arg Asn Arg Gln
        195                 200                 205

Lys Arg Phe Pro Thr Ile Pro Leu Ser Arg Pro Phe Asp Asn Ala Met
    210                 215                 220

Leu Arg Ala His Arg Leu His Gln Leu Ala Phe Asp Thr Tyr Gln Glu
225                 230                 235                 240

Phe Glu Glu Ala Tyr Ile Pro Lys Glu Gln Lys Tyr Ser Phe Leu Gln
                245                 250                 255

Asn Pro Gln Thr Ser Leu Cys Phe Ser Glu Ser Ile Pro Thr Pro Ser
            260                 265                 270

Asn Arg Glu Glu Thr Gln Gln Lys Ser Asn Leu Glu Leu Leu Arg Ile
    275                 280                 285

Ser Leu Leu Leu Ile Gln Ser Trp Leu Glu Pro Val Gln Phe Leu Arg
    290                 295                 300

Ser Val Phe Ala Asn Ser Leu Val Tyr Gly Ala Ser Asp Ser Asn Val
305                 310                 315                 320

Tyr Asp Leu Leu Lys Asp Leu Glu Glu Gly Ile Gln Thr Leu Met Gly
                325                 330                 335

Arg Leu Glu Asp Gly Ser Pro Arg Thr Gly Gln Ile Phe Lys Gln Thr
            340                 345                 350

Tyr Ser Lys Phe Asp Thr Asn Ser His Asn Asp Asp Ala Leu Leu Lys
        355                 360                 365

Asn Tyr Gly Leu Leu Tyr Cys Phe Arg Lys Asp Met Asp Lys Val Glu
    370                 375                 380

Thr Phe Leu Arg Ile Val Gln Cys Arg Ser Val Glu Gly Ser Cys Gly
385                 390                 395                 400

Phe
```

```
<210> SEQ ID NO 37
<211> LENGTH: 400
<212> TYPE: PRT
<213> ORGANISM: Homo sapiens

<400> SEQUENCE: 37

Met Glu Trp Val Trp Ala Leu Val Leu Leu Ala Ala Leu Gly Gly Gly
  1               5                  10                  15

Ser Ala Glu Arg Asp Cys Arg Val Ser Ser Phe Arg Val Lys Glu Asn
             20                  25                  30

Phe Asp Lys Ala Arg Phe Ser Gly Leu Trp Tyr Ala Ile Ala Lys Lys
         35                  40                  45

Asp Pro Glu Gly Leu Phe Leu Gln Asp Asn Ile Ile Ala Glu Phe Ser
     50                  55                  60

Val Asp Glu Lys Gly His Met Ser Ala Thr Ala Lys Gly Arg Val Arg
 65                  70                  75                  80

Leu Leu Ser Asn Trp Glu Val Cys Ala Asp Met Val Gly Thr Phe Thr
                 85                  90                  95

Asp Thr Glu Asp Pro Ala Lys Phe Lys Met Lys Tyr Trp Gly Val Ala
            100                 105                 110

Ser Phe Leu Gln Arg Gly Asn Asp Asp His Trp Ile Ile Asp Thr Asp
        115                 120                 125

Tyr Asp Thr Phe Ala Leu Gln Tyr Ser Cys Arg Leu Gln Asn Leu Asp
    130                 135                 140

Gly Thr Cys Ala Asp Ser Tyr Ser Phe Val Phe Ser Arg Asp Pro Asn
145                 150                 155                 160

Gly Leu Thr Pro Glu Thr Arg Arg Leu Val Arg Gln Arg Gln Glu Glu
                165                 170                 175

Leu Cys Leu Glu Arg Gln Tyr Arg Trp Ile Glu His Asn Gly Tyr Cys
            180                 185                 190

Gln Ser Arg Pro Ser Arg Asn Ser Leu Thr Ser Ala Arg Asn Arg Gln
        195                 200                 205

Lys Arg Phe Pro Thr Ile Pro Leu Ser Arg Pro Phe Asp Asn Ala Met
    210                 215                 220

Leu Arg Ala His Arg Leu His Gln Leu Ala Phe Asp Thr Tyr Gln Glu
225                 230                 235                 240

Phe Glu Glu Ala Tyr Ile Pro Lys Glu Gln Lys Tyr Ser Phe Leu Gln
                245                 250                 255

Asn Pro Gln Thr Ser Leu Cys Phe Ser Glu Ser Ile Pro Thr Pro Ser
            260                 265                 270

Asn Arg Glu Glu Thr Gln Gln Lys Ser Asn Leu Glu Leu Leu Arg Ile
        275                 280                 285

Ser Leu Leu Leu Ile Gln Ser Trp Leu Glu Pro Val Gln Phe Leu Arg
    290                 295                 300

Ser Val Phe Ala Asn Ser Leu Val Tyr Gly Ala Ser Asp Ser Asn Val
305                 310                 315                 320

Tyr Asp Leu Leu Lys Asp Leu Glu Glu Gly Ile Gln Thr Leu Met Gly
                325                 330                 335

Arg Leu Glu Asp Gly Ser Pro Arg Thr Gly Gln Ile Phe Lys Gln Thr
            340                 345                 350

Tyr Ser Lys Phe Asp Thr Asn Ser His Asn Asp Asp Ala Leu Leu Lys
        355                 360                 365

Asn Tyr Gly Leu Leu Tyr Cys Phe Arg Lys Asp Met Asp Lys Val Glu
    370                 375                 380
```

-continued

```
Thr Phe Leu Arg Ile Val Gln Cys Arg Ser Val Glu Gly Ser Cys Gly
385                 390                 395                 400
```

<210> SEQ ID NO 38
<211> LENGTH: 1204
<212> TYPE: DNA
<213> ORGANISM: Homo sapiens

<400> SEQUENCE: 38

```
atggagtggg tgtgggcgct cgtgctgctg gcggctctgg gaggcggcag cgccgagcgc    60
gactgcaggg tgagcagctt cagagtcaag gagaacttcg acaaggctcg tttctctggg   120
ctctggtatg ccatcgccaa aaaggatccc gagggtctct ttttgcaaga caacatcatc   180
gctgagtttt ctgtcgacga gaagggtcat atgagcgcta cagccaaggg acgagtccgt   240
cttctgagca actgggaagt gtgtgcagac atggtgggca ctttcacaga tacagaagat   300
cctgccaagt tcaagatgaa gtactggggt gtagcctcct ttctccagcg aggaaacgat   360
gaccactgga tcatcgatac ggactacgac accttcgctc tgcagtattc ctgccgcctg   420
cagaatctgg atggcacctg tgcagacagc tactcctttg tgttttctcg tgacccaat    480 ggcctgaccc cggagacacg gaggctggtg aggcagcgac aggaggagct gtgcctagag   540
aggcagtaca gatggatcga gcacaatggt tactgtcaaa gcagaccctc aagaaacagt   600
ttgactagtg ctagaaaccg tcagaagaga ttcccaacca ttcccttaag caggcctttt   660
gacaacgcta tgctccgcgc ccatcgtctg caccagctgg cctttgacac ctaccaggag   720
tttgaagaag cctatatccc aaaggaacag aagtattcat tcctgcagaa cccccagacc   780
tccctctgtt tctcagagtc tattccgaca ccctccaaca gggaggaaac acaacagaaa   840
tccaacctag agctgctccg catctccctg ctgctcatcc agtcgtggct ggagcccgtg   900
cagttcctca ggagtgtctt cgccaacagc ctggtgtacg gcgcctctga cagcaacgtc   960
tatgacctcc taaaggacct agaggaaggc atccaaacgc tgatggggag gctggaagat  1020
ggcagccccc ggactgggca gatcttcaag cagacctaca gcaagttcga cacaaactca  1080
cacaacgatg acgcactact caagaactac gggctgctct actgcttcag gaaggacatg  1140
gacaaggtcg agacattcct gcgcatcgtg cagtgccgct ctgtggaggc agctgtggtt  1200
ctag                                                               1204
```